US006953788B1

(12) United States Patent
Warshawsky et al.

(10) Patent No.: US 6,953,788 B1
(45) Date of Patent: Oct. 11, 2005

(54) 3-MERCAPTOACETYLAMINO-1,5-SUBSTITUTED-2-OXO-AZEPAN DERIVATIVES USEFUL AS INHIBITORS OF MATRIX METALLOPROTEINASE

(75) Inventors: Alan M. Warshawsky, Cincinnati, OH (US); Joseph T. Tsay, Cincinnati, OH (US); Michael J. Janusz, Oregonia, OH (US); Jian Shen, Cincinnati, OH (US); Gary A. Flynn, Tucson, AZ (US); Ramalinga M. Dharanipragada, Tucson, AZ (US); Joseph P. Burkhart, Plainfield, IN (US); Douglas W. Beight, Indianapolis, IN (US); Meena V. Patel, Chicago, IL (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 08/893,080

(22) Filed: Dec. 19, 1997

Related U.S. Application Data

(60) Provisional application No. 60/052,527, filed on Sep. 19, 1996.

(51) Int. Cl.[7] .................... C07D 243/00; C07D 401/00; C07D 223/12; A61K 31/55; A61P 19/02
(52) U.S. Cl. .......................... 514/212.03; 514/212.08; 514/218; 540/492; 540/524; 540/527
(58) Field of Search ................. 540/492, 524, 540/527; 514/212.03, 212.08, 218

(56) References Cited

U.S. PATENT DOCUMENTS

| | | |
|---|---|---|
| 4,599,361 A | 7/1986 | Dickens et al. |
| 4,681,966 A | 7/1987 | Donald et al. |
| 4,771,038 A | 9/1988 | Wolanin et al. |
| 4,885,283 A | 12/1989 | Broadhurst et al. |
| 4,935,404 A | 6/1990 | Hunter et al. |
| 5,238,932 A | 8/1993 | Flynn et al. |
| 5,239,078 A | 8/1993 | Galardy et al. |
| 5,252,560 A | 10/1993 | Myers et al. |
| 5,300,501 A | 4/1994 | Porter et al. |
| 5,304,549 A | 4/1994 | Broadhurst et al. |
| 5,310,763 A | 5/1994 | Campion et al. |
| 5,362,750 A | 11/1994 | Rosini et al. |
| 5,366,973 A | 11/1994 | Flynn et al. |
| 5,389,628 A | 2/1995 | Flynn et al. |
| 5,420,271 A | 5/1995 | Warshawsky et al. |
| 5,424,425 A | 6/1995 | Flynn et al. |
| 5,428,158 A | 6/1995 | Warshawsky et al. |
| 5,430,145 A | 7/1995 | Flynn et al. |
| 5,455,242 A | 10/1995 | Warshawsky et al. |
| 5,457,196 A | 10/1995 | Warshawsky et al. |
| 5,504,212 A | 4/1996 | de Solmes et al. |

FOREIGN PATENT DOCUMENTS

| | | |
|---|---|---|
| EP | 0236872 | 9/1987 |
| EP | 0489579 | 6/1992 |
| EP | 0534363 | 3/1993 |
| EP | 0621270 | 10/1994 |
| WO | 9606890 | 9/1988 |
| WO | 9513289 | 5/1995 |
| WO | 9611209 | 4/1996 |
| WO | 9629313 | 9/1996 |
| WO | 9635687 | 11/1996 |
| WO | 9635711 | 11/1996 |
| WO | 9635714 | 11/1996 |
| WO | 9636227 | 11/1996 |
| WO | 9665712 | 11/1996 |
| WO | 9712861 | 4/1997 |
| WO | 9712902 | 4/1997 |
| WO | 9717088 | 5/1997 |
| WO | 9719075 | 5/1997 |

OTHER PUBLICATIONS

Greenwald, Annals of the New York Academy of Sciences 878:413–419 (1999).*
McCachren, S.S. *Arthritis Rheum.* 34, pp 1085–1093 (1991).
Emonard, H. et al, *Cell Molec. Biol.* 36, pp 131–153 (1990).
Birkedal–Hansen, H., *J. Oral Pathol.* 17, pp 445–451 (1988).
Matrisian, L.M., *Trends Genet.* 6, pp 121–125 (1990).
Murphy, G.J.P. et al, *FEBS Lett.* 289, pp 4–7 (1991).
Matrisian, L.M., *Bioessays* 14, pp 455–463 (1992).
Swhwartz, G.K. et al, *Cancer* 73, pp 22–27 (1994).
Bernhard, E.J. et al, *Proc. Natl. Acad. Sci.* 91, pp 4293–4597 (1994).
Zucker, S. et al, Cancer Res. 53, pp 140–146 (1993).
Chirivi, R.G.S. et al, *Int. J. Cancer* 58, pp 460–464 (1994).
Montgomery, A.M.P. et al, *Cancer Res.* 54, pp 5467–5473 (1994).
Hasty, K.A. et al, *Arthr. Rheum.* 33, pp 388–397 (1990).
Murphy, G. et al, *Biochem. J.* 248, pp 265–268 (1987).
Gearing, A.J.H. et al, *Nature* 370, pp 555–557 (1994).
Mohler, K.M. et al, *Nature* 370, pp 218–220 (1994).
McGreehan, G.M. et al, *Nature* 370, pp 558–561 (1994).
Wahl, R.C. et al, *Annual Reports in Medicinal Chemistry* 25, pp 177–184 (1990).
Hennney, A.m., et al, *Proc. Natl. Acad. Sci.* 88, pp 8154–8158 (1991).
Burns, F.R. et al, *Invest. Opthalmol. and Visual Sci.* 30, No. 7 pp 1569–1575 (1989).
Overall, C.M. et al, *J. Periodontal Res.* 22, pp 81–88 (1987).
Miyazaki, K. et al, *Nature* 362, pp 839–841 (1993).

(Continued)

*Primary Examiner*—Bruck Kifle
(74) *Attorney, Agent, or Firm*—Synnestvedt & Lechner LLP

(57) ABSTRACT

The present invention relates to certain novel 3-mercaptoacetylamino-1,5-substituted-2-oxo-azepan derivatives useful as inhibitors of matrix metalloproteinase. Pharmaceutical compositions containing said compounds as well as methods of treating various disease states responding to inhibition of matrix metalloproteinase are also claimed herein.

42 Claims, No Drawings

OTHER PUBLICATIONS

Beckett, R.P. et al, "Recent advances in matrix metalloproteinase inhibitor research" *DDT* vol. 1, No. 1, Jan., 1996, pp 16–26.

Blanchard et al, "Reevaluation of the Absorption of Carbenoxolone Using an In Situ Rat Intestinal Techinque", *Journ. Pharmaceutical Sci.*, vol. 79, No. 5, May, 1990 pp 411–414.

Davies, B. et al, "A Synthetic Matrix Metalloproteinase Inhibitor Decreases Tomor Burden . . . ", *Cancer Research* 53, May 1, 1993, pp 2087–2091.

Hodgson, John, "Remodeling MMPIs", *Bio/Technology* vol. 13, Jun. 1995 pp 554–557.

Chapman, K.T., "Inhibition of Matrix Metalloproteinases . . . ", J. Med. Chem. 1993, 36, pp 4293–4301.

Beeley N.R.A, "Inhibitors of Matrix Metalloproteinases (MMP's)", Curr. Opin, Ther. Patents (1994) 4(1), pp 7–16.

Baxter, Andrew D. et al, "A Novel Series of Matrix Metalloproteinase Inhibitors for the Treatment of Inflammatory Disorders", Bioorganic & Medicinal Chem. Letters, vol. 7, No. 7 pp 897–902, (1997).

CA, Issue 3, pp 16, 126:60361y (1997).

Derwent Abstract 96–035866, Week 9604, WPI Database XP 002046217.

Burkholder, E.A., Bioorg Med Chem Lett, vol. 3, No. 2, 1993, p 231–234, XP002046216.

* cited by examiner

3-MERCAPTOACETYLAMINO-1,5-SUBSTITUTED-2-OXO-AZEPAN DERIVATIVES USEFUL AS INHIBITORS OF MATRIX METALLOPROTEINASE

This application claims the benefit of Provisional Application No. 60/052,527, filed Sep. 19, 1996.

BACKGROUND OF THE INVENTION

The Matrix metalloproteinases (MMP's) are a family of zinc containing endopeptidases which are capable of cleaving large biomolecules such as the collagens, proteoglycans and gelatins. Expression is upregulated by pro-inflammatory cytokines and/or growth factors. The MMP's are secreted as inactive zymogens which, upon activation, are subject to control by endogenous inhibitors, for example, tissue inhibitor of metalloproteinases (TIMP) and $\alpha_2$-macroglobulin. Chapman, K. T. et al., *J. Med. Chem.* 36, 4293–4301 (1993); Beckett, R. P. et al., *DDT* 1, 16–26 (1996). The characterizing feature of diseases involving the enzymes appears to be a stoichiometric imbalance between active enzymes and endogenous inhibitors, leading to excessive tissue disruption, and often degradation. McCachren, S. S., *Arthritis Rheum.* 34, 1085–1093 (1991).

The discovery of different families of matrix metalloproteinase, their relationships, and their individual characteristics have been categorized in several reports. Emonard, H. et al., *Cell Molec. Biol.* 36, 131–153 (1990); Birkedal-Hansen, H., *J. Oral Pathol.* 17, 445–451 (1988); Matrisian, L. M., *Trends Genet.* 6, 121–125 (1990); Murphy, G. J. P. et al., *FEBS Lett.* 289, 4–7 (1991); Matrisian, L. M., *Bioessays* 14, 455–463 (1992). Three groups of secreted MMPs have been delineated: the collagenases which have triple helical interstitial collagen as a substrate, the gelatinases which are proteinases of denatured collagen and Type IV collagen, and the stromelysins which were originally characterized as proteoglycanases but have now been identified to have a broader proteolytic spectrum. Examples of specific collagenases include fibroblast collagenase (MMP-1), neutrophil collagenase (MMP-8), and collagenase 3 (MMP-13). Examples of gelatinases include 72 kDa gelatinase (gelatinase A; MMP-2) and 92 kDa gelatinase (gelatinase B; MMP-9). Examples of stromelysins include stromelysin 1 (MMP-3), stromelysin 2 (MMP-10) and matrilysin (MMP-7). Other MMPs which do not fit neatly into the above groups include metalloelastase (MMP-12), membrane-type MMP (MT-MMP or MMP-14) and stromelysin 3 (MMP-11). Beckett, R. P. et al., *supra*.

Over-expression and activation of MMPs have been linked with a wide range of diseases such as cancer; rheumatoid arthritis; osteoarthritis; chronic inflammatory disorders, such as emphysema; cardiovascular disorders, such as atherosclerosis; corneal ulceration; dental diseases such as gingivitis and periodontal disease; and neurological disorders such as multiple sclerosis. For example, in adenocarcinoma, invasive proximal gastric cells express the 72 kDa form of collagenase Type IV, whereas the noninvasive cells do not. Schwartz, G. K. et al., *Cancer* 73, 22–27 (1994). Rat embryo cells transformed by the Ha-ras and v-myc oncogenes or by Ha-ras alone are metastatic in nude mice and release the 92 kDa gelatinase/collagenase (MMP-9). Bernhard, E. J. et al., *Proc. Natl. Acad. Sci.* 91, 4293–4597 (1994). The plasma concentration of MMP-9 was significantly increased (P<0.01) in 122 patients with gastrointestinal tract cancer and breast cancer. Zucker, S. et al., *Cancer Res.* 53, 140–146 (1993). Moreover, intraperitoneal administration of batimastat, a synthetic MMP inhibitor, gave significant inhibition in the growth and metastatic spread and number of lung colonies which were produced by intravenous injection of the B16-BL6 murine melanoma in C57BL/6N mice. Chirivi, R. G. S. et al., *Int. J. Cancer* 58, 460–464 (1994). Over-expression of TIMP-2, the endogenous tissue inhibitor of MMP-2, markedly reduced melanoma growth in the skin of immunodeficient mice. Montgomery, A. M. P. et al., *Cancer Res.* 54, 5467–5473 (1994).

Accelerated breakdown of the extracellular matrix of articular cartilage is a key feature in the pathology of both rheumatoid arthritis and osteoarthritis. Current evidence suggests that the inappropriate synthesis of MMPs is the key event. Beeley, N. R. A. et al., *Curr. Opin. Ther. Patents*, 4(1), 7–16 (1994). The advent of reliable diagnostic tools have allowed a number of research groups to recognize that stromelysin is a key enzyme in both arthritis and joint trauma. Beeley, N. R. A. et al., *Id.*; Hasty, K. A. et al., *Arthr. Rheum.* 33, 388–397 (1990). It has also been shown that stromelysin is important for the conversion of procollagenase to active collagenase. Murphy, G. et al., *Biochem. J.* 248, 265–268 (1987).

Furthermore, a range of MMPs can hydrolyse the membrane-bound precursor of the pro-inflammatory cytokine tumor necrosis factor $\alpha$ (TNF-$\alpha$). Gearing, A. J. H. et al., *Nature* 370, 555–557 (1994). This cleavage yields mature soluble TNF-$\alpha$ and the inhibitors of MMPs can block production of TNF-$\alpha$ both in vitro and in vivo. Gearing, A. J. H. et al., *Id.*; Mohler, K. M. et al., *Nature* 370, 218–220 (1994); McGeehan, G. M. et al., *Nature* 370, 558–561 (1994). This pharmacological action is a probable contributor to the antiarthritic action of this class of compounds seen in animal models. Beckett, R. P. et al., *supra*.

Stromelysin has been observed to degrade the $\alpha_1$-proteinase inhibitor which regulates the activity of enzymes such as elastase, excesses of which have been linked to chronic inflammatory disorders such as emphysema and chronic bronchitis. Inhibition of the appropriate MMP may thus potentiate the inhibitory activity of endogenous inhibitors of this type. Beeley, N. R. A. et al., *supra*.; Wahl, R. C. et al., *Annual Reports in Medicinal Chemistry* 25, 177–184 (1990).

High levels of mRNA corresponding to stromelysin have been observed in atherosclerotic plaques removed from heart transplant patients. Henney, A. M., et al., *Proc. Natl. Acad. Sci.* 88, 8154–8158 (1991). It is submitted that the role of stromelysin in such plaques is to encourage rupture of the connective tissue matrix which encloses the plaque. This rupture is in turn thought to be a key event in the cascade which leads to clot formation of the type seen in coronary thrombosis. MMP inhibition is thus a preventive measure for such thromboses.

Collagenase, stromelysin and gelatinase have been implicated in the destruction of the extracellular matrix of the cornea. This is thought to be an important mechanism of morbidity and visual loss in a number of ulcerative ocular diseases, particularly those following infection or chemical damage. Burns, F. R. et al., *Invest. Opthalmol. and Visual Sci.* 32, 1569–1575 (1989). The MMPs present in the eye during ulceration are derived either endogenously from infiltrating leucocytes or fibroblasts, or exogenously from microbes.

Collagenase and stromelysin activities have been identified in fibroblasts isolated from inflamed gingiva and the levels of enzyme have been correlated with the severity of the gingivitis observed. Beeley, N. R. A. et al., *supra*.; Overall, C. M. et al., *J. Periodontal Res.* 22, 81–88 (1987).

Excessive levels of gelatinase-B in cerebrospinal fluid has been linked with incidence of multiple sclerosis and other neurological disorders. Beeley, N. R. A. et al., *supra*.; Miyazaki, K. et al., *Nature* 362, 839–841 (1993). The enzyme may play a key role in the demyelination of neurones and the breakdown of the blood brain barrier which occurs in such disorders.

Existing MMP inhibitors already in development include pseudo-peptide derivatives developed by substrate-based design and other compounds identified from random screening of compound libraries and natural products. In the substrate-based design, a key to obtaining potent enzyme inhibition has been the incorporation of a zinc binding group (ZBG) to chelate the active site zinc(II) ion, into peptide analogs of the sequence on either the left-hand side (LHS) or the right-hand side (RHS), or both sides of the cleavage site. Several different ZBGs have been identified, namely, hydroxamate, carboxylate, aminocarboxylate, suphydryl and derivatives of phosphorous acids. While hydroxamate compounds, such as Batimastat, are currently undergoing clinical testing and have proven to be some of the most active compounds in vitro, they possess bioavailability problems and may also degrade into carcinogenic analogs, such as hydroxylamine.

It would thus be advantageous to provide additional matrix metalloproteinase inhibitors. It would also be advantageous to control the imbalance of matrix metalloproteinase without producing carcinogenic side-products.

SUMMARY OF THE INVENTION

The present invention provides novel compounds of the formula

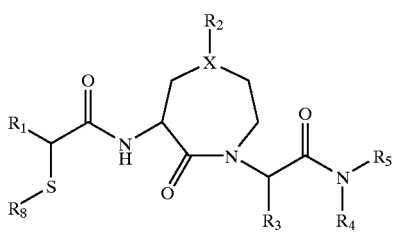

(1)

wherein $R_1$ is $C_1$–$C_6$ alkyl, a W—$(CH_2)_m$— group, or a Q—Z—$(CH_2)_m$— group wherein W is phthalimido; Z is a bond or is oxy, $NR_6$, $C(O)NR_6$, $NR_6C(O)$, $NHC(O)NR_6$, $OC(O)NR_6$, $HNC(O)O$, or $SO_2NR_6$; Q is hydrogen, or a Y—$(CH_2)_n$— group wherein Y is hydrogen, $C_6$–$C_{10}$ aryl, $C_3$–$C_9$ heteroaryl, —$C(O)OR_6$, —$N(R_6)_2$, morpholino, piperidino, pyrrolidino, or isoindolyl;

$R_2$ is $C_1$–$C_4$ alkyl, a —$(CH_2)_p$—$(C_3$–$C_9)$heteroaryl group, or a —$(CH_2)_p$—$Ar_1$ group wherein $Ar_1$ is phenyl or naphthyl optionally substituted with a substituent selected from the group consisting of halogen, $C_1$–$C_4$ alkyl, —$OR_7$, —$N(R_6)_2$, $SO_2N(R_6)_2$ or —$NO_2$;

$R_3$ is hydrogen, $C_1$–$C_6$ alkyl, —$CH_2SCH_2NHCOCH_3$, a —$(CH_2)_p$—A group, a —$(CH_2)_m$—B group or a —$CH_2$—D—$R_7$ group wherein A is $C_6$–$C_{10}$ aryl, $C_3$–$C_9$ heteroaryl, or cyclohexyl; B is —$N(R_7)_2$, guanidino, nitroguanidino, —$C(O)OR_6$ or —$C(O)NR_6$; and D is oxy or thio;

$R_4$ is hydrogen or a —$(CH_2)_m$—$S(O)_pX'(R_6)_2$ group;

$R_5$ is hydrogen, $C_1$–$C_6$ alkyl or $R_4$ and $R_5$ taken together with the nitrogen atom to which they are attached form piperidino, pyrrolidino, or isoindolyl;

$R_6$ is hydrogen or $C_1$–$C_6$ alkyl;

$R_7$ is hydrogen, $C_1$–$C_4$ alkyl, or a —$(CH_2)_p$—$Ar_2$ group wherein $Ar_2$ is phenyl or naphthyl optionally substituted with a substituent selected from the group consisting of halogen, $C_1$–$C_4$ alkyl, —$OR_7$, —$N(R_6)_2$, $SO_2N(R_6)_2$ or —$NO_2$;

$R_8$ is hydrogen, —$C(O)R_7$, a —$C(O)$—$(CH_2)_q$—K group or a —S—G group, wherein K is selected from the group consisting of

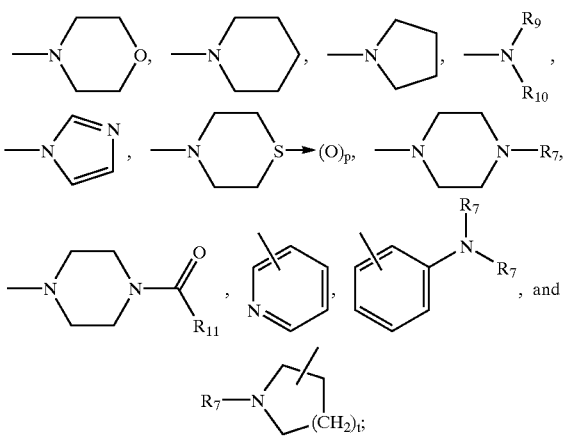

G is selected from the group consisting of

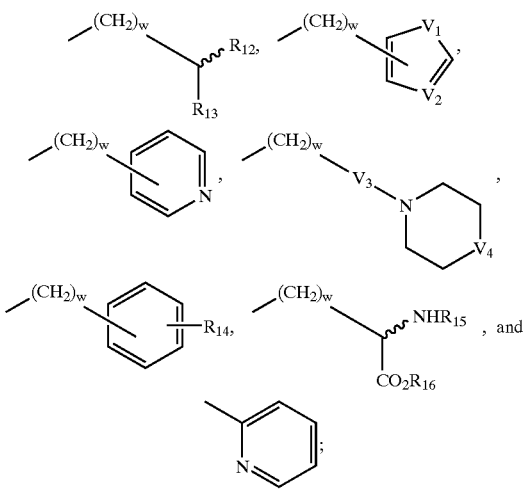

$R_9$ and $R_{10}$ are each independently $C_1$–$C_4$ alkyl or a —$(CH_2)_p$—$Ar_2$ group;

$R_{11}$ is —$CF_3$, $C_1$–$C_{10}$ alkyl or a —$(CH_2)_p$—$Ar_2$ group;

$R_{12}$ is hydrogen, $C_1$–$C_6$ alkyl, —$CH_2CH_2S(O)_pCH_3$, or arylalkyl;

$R_{13}$ is hydrogen, hydroxy, amino, $C_1$–$C_6$ alkyl, N-methylamino, N,N-dimethylamino, —$CO_2R_{17}$ or —$OC(O)R_{18}$ wherein $R_{17}$ is hydrogen, —$CH_2O$—$C(O)$$C(CH_3)_3$, $C_1$–$C_4$ alkyl, a —$(CH_2)_p$—$Ar_2$ group or diphenylmethyl and $R_{18}$ is hydrogen, $C_1$–$C_6$ alkyl or phenyl;

$R_{14}$ is 1 or 2 substituents independently chosen from the group consisting of hydrogen, $C_1$–$C_4$ alkyl, $C_1$–$C_4$ alkoxy, or halogen;

$R_{15}$ is hydrogen, $C_1$–$C_6$ alkyl or a —$(CH_2)_p$—$Ar_2$ group;

$R_{16}$ is hydrogen or $C_1$–$C_4$ alkyl;

$V_1$ is O, S, or NH;

$V_2$ is N or CH;

$V_3$ is a bond or —$C(O)$—;

$V_4$ is —(CH$_2$)$_{w'}$$^{O, S, NR}$$_7$, or NC(O)R$_{11}$;

X and X' are each independently CH or N;

m is an integer 2–4;

n is zero or an integer 1–4;

p is zero or an integer 1–2;

q is zero or an integer 1–5;

t is an integer 1–2;

w is an integer 1–3; and w' is zero or an integer 1; or a pharmaceutically acceptable salt, stereoisomer or hydrate thereof.

The present invention further provides a method of inhibiting matrix metallo-proteinases (MMPs) in a patient in need thereof comprising administering to the patient an effective matrix metalloproteinase inhibiting amount of a compound of formula (1).

In addition, the present invention provides a composition comprising an assayable amount of a compound of formula (1) in admixture or otherwise in association with an inert carrier. The present invention also provides a pharmaceutical composition comprising an effective MMP inhibitory amount of a compound of formula (1) in admixture or otherwise in association with one or more pharmaceutically acceptable carriers or excipients.

DETAILED DESCRIPTION OF THE PREFERRED EMBODIMENTS

As used in this application:

a) the designation "〰〰" refers to a bond for which the stereochemistry is not designated.

b) the designation "━━▬" refers to a bond that protrudes forward out of the plane of the page.

c) the designation "·····ııı" refers to a bond that protrudes backward out of the plane of the page.

The expression "pharmaceutically acceptable salt" is intended to apply to any non-toxic organic or inorganic salt of a compound of formula (1). Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Such salts can exist in either the hydrated or substantially anhydrous form.

As used herein, the term "C$_1$–C$_4$ alkyl" refers to a saturated straight or branched chain hydrocarbyl radical of one to four carbon atoms and includes methyl, ethyl, propyl, isopropyl, n-butyl, isobutyl, tertiary butyl and the like. The term "C$_1$–C$_6$ alkyl" refers to a saturated straight or branched chain hydrocarbyl radical of one to six carbon atoms and includes methyl, ethyl, propyl, isopropyl, n-butyl, isobutyl, tertiary butyl, n-pentyl, sec-pentyl, isopentyl, n-hexyl and the like. The term "C$_1$–C$_{10}$ alkyl" refers to a saturated straight or branched chain hydrocarbyl radical of one to ten carbon atoms and includes methyl, ethyl, propyl, isopropyl, n-butyl, isobutyl, tertiary butyl, n-pentyl, sec-pentyl, isopentyl, n-hexyl, 2,3-dimethyl-2-butyl, heptyl, 2,2-dimethyl-3-pentyl, 2-methyl-2-hexyl, octyl, 4-methyl-3-heptyl, nonyl, decyl and the like.

The term "C$_1$–C$_4$ alkoxy" refers to a straight or branched alkoxy group containing from 1 to 4 carbon atoms, such as methoxy, ethoxy, n-propoxy, isopropoxy, n-butoxy, isobutoxy, t-butoxy, and the like.

The designation "—C(O)—" refers to a carbonyl group of the formula

The term "C$_6$–C$_{10}$ aryl" refers to a cyclic aromatic assemblage of conjugated carbon atoms, optionally substituted with one to three substituents selected from the group consisting of F, Cl, C$_1$–C$_4$ alkyl, —OR$_7$, —N(R$_6$)$_2$, or —NO$_2$, including phenyl, 1-naphthyl, 2-naphthyl, 2-hydroxyphenyl, 3-hydroxyphenyl, 4-hyroxyphenyl, 2,3-dihydroxyphenyl, 2,4-dihydroxyphenyl, 3,4-dihydroxyphenyl, 2,3,4-trihydroxyphenyl, 4-methoxyphenyl, 4-ethoxyphenyl, 2-chlorophenyl, 3-chlorophenyl, 4-chlorophenyl, 3,4-dichlorophenyl, 2,3,4-trichlorophenyl, 4-bromophenyl, 3,4-dibromophenyl, 4-fluorophenyl, 3,4-difluorophenyl, 3-tolyl, 4-tolyl, 4-ethylphenyl, 4-isopropylphenyl, 3-aminophenyl, 4-aminophenyl, 3,4-diaminophenyl, N-methyl-4-aminophenyl, 2-nitrophenyl, 4-nitrophenyl, 3-bromo-4-tolyl, and the like.

The term "C$_3$–C$_9$ heteroaryl" means a cyclic or bicyclic, aromatic assemblage of conjugated carbon atoms and from 1 to 3 nitrogen, oxygen and sulfur atoms, for example, pyridinyl, 2-quinoxalinyl, quinolinyl, pyridazine, pyrimidyl, pyrazolyl, pyrazyl, thiophyl, furyl, imidazolyl, oxazolyl, thiazolyl and the like.

The terms "PhtN" or "phthalimido" refer to a phthalimido functionality of the formula:

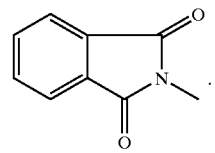

The terms "Boc", "t-butyloxycarbonyl", or "tert-butoxycarbonyl" refer to a t-butyloxycarbonyl functionality of the formula;

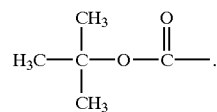

The terms "CBz" or "carbobenzyloxy" refer to a carbobenzyloxy functionality of the formula;

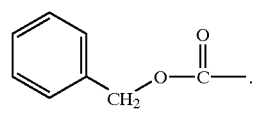

The designations "C(O)NR$_6$", "NR$_6$C(O)", "N HC(O) NR$_6$", "OC(O)NR$_6$", "R$_6$NC(O)O" or "SO$_2$NR$_6$" refer to amide bond or modified amide bond functionalities and are represented, respectively, by the following formulae:

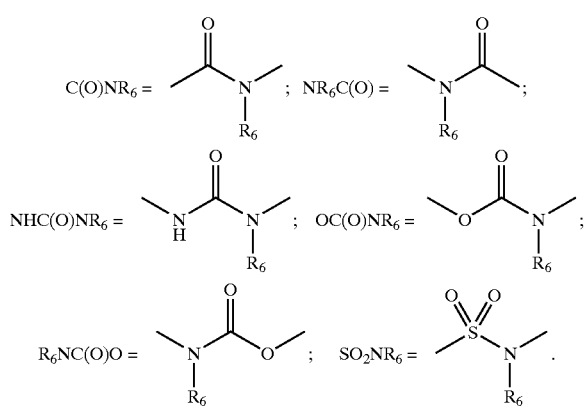

The terms "$Ar_1$", "$Ar_2$" or "aryl" refers to a phenyl or naphthyl group unsubstituted or substituted with from one to three substituents selected from the group consisting of F, Cl, $C_1$–$C_4$ alkyl, —$OR_7$, —$N(R_6)_2$, $SO_2N(R_6)_2$ or —$NO_2$,; specifically included within the scope of the term "aralkyl" are phenyl, naphthyl, naphthylmethyl, phenylmethyl or benzyl, phenylethyl, p-methoxybenzyl, 3,4-methylenedioxybenzyl, p-fluorobenzyl and p-chlorobenzyl.

For the purposes of this invention, when "$Ar_1$" is phenyl, the substituent or substituents may only be attached at the 3, 4 or 5 positions of the phenyl moiety. When "$Ar_1$" is naphthyl, the radical can be attached at the 2-position, and the substituent or substituents may only be attached at the 5, 6, 7 or 8 positions, as illustrated by the following designations:

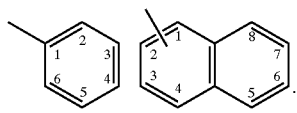

For the purposes of this invention, when "$Ar_2$" is phenyl, the substituent or substituents can be attached at the 2, 3, 4, 5 or 6 positions of the phenyl moiety. When "$Ar_2$" is naphthyl, it is understood that the radical can be attached at the either the I-position or the 2-position, it is further understood that when the radical is attached at the 1-position the substituent or substituents can be attached in any of the 2, 3, 4, 5, 6, 7, or 8 positions and that when the radical is attached at the 2-position the substituent or substituents can be attached in any of the 1, 3, 4, 5, 6, 7, or 8 positions.

The term "halogen" refers to fluorine, chlorine, bromine or iodine.

The term "stereoisomers" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereomers). Any reference in this application to one of the compounds of formula (1) is meant to encompass either specific stereoisomers or a mixture of stereoisomers. The specific stereoisomers can be prepared by stereospecific synthesis or can be separated and recovered by techniques known in the art, such as chromatography, chromatography on chiral stationary phases, fractional recrystallization of addition salts formed by reagents used for that purpose, as described in *Enantiomers, Racemates, and Resolutions*, J. Jacques, A. Collet, and S. H. Wilen, Wiley (1981).

One embodiment of the novel compounds is that of formula (1) wherein X is CH and $R_8$ is hydrogen.

In a class of this embodiment, $R_1$ is $C_1$–$C_6$ alkyl, preferably methyl, ethyl, propyl, isopropyl, butyl or isobutyl; $R_2$ is $C_1$–$C_4$ alkyl, a —$(CH_2)_p$—$Ar_1$ group wherein Ar is phenyl optionally substituted with F, Cl, $C_1$–$C_4$ alkyl, or —$OR_7$ or is a —$(CH_2)_p$—$(C_3$–$C_9)$heteroaryl group wherein the $(C_3$–$C_9)$heteroaryl group is thienyl, 2-pyridyl or thiazolyl; $R_4$ is hydrogen; $R_5$ is hydrogen, methyl, ethyl, propyl, isopropyl, butyl or isobutyl.

In another class of this embodiment, $R_1$ is a W—$(CH_2)_m$— group; $R_2$ is $C_1$–$C_4$ alkyl, a —$(CH_2)_p$—$Ar_1$ group wherein $Ar_1$ is phenyl optionally substituted with F, Cl, $C_1$–$C_4$ alkyl, or —$OR_7$ or is a —$(CH_2)_p$—$(C_3$–$C_9)$ heteroaryl group wherein the $(C_3$–$C_9)$heteroaryl group is thienyl, 2-pyridyl or thiazolyl; $R_4$ is hydrogen; $R_5$ is hydrogen, methyl, ethyl, propyl, isopropyl, butyl or isobutyl.

In another class of this embodiment, $R_1$ is a Q—Z—$(H_2)_m$— group; $R_2$ is $C_1$–$C_4$ alkyl, a —$(CH_2)_p$—$Ar_1$ group wherein $Ar_1$ is phenyl optionally substituted with F, Cl, $C_1$–$C_4$ alkyl, or —$OR_7$ or is a —$(CH_2)_p$—$(C_3$–$C_9)$ heteroaryl group wherein the $(C_3$–$C_9)$heteroaryl group is thienyl, 2-pyridyl or thiazolyl; $R_4$ is hydrogen; $R_5$ is hydrogen, methyl, ethyl, propyl, isopropyl, butyl or isobutyl.

Exemplifying this embodiment are the following compounds of the Formulae II and III shown in Tables 1 and 2:

TABLE 1

Formula II

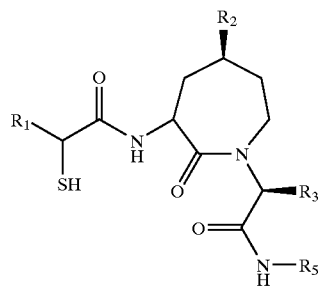

| Compd. No. | $R_1$ | $R_2$ | $R_3$ | $R_5$ |
|---|---|---|---|---|
| II-1 | PhtN—$(CH_2)_4$— | phenyl | benzyl | —$CH_3$ |
| II-2 | PhtN—$(CH_2)_4$— | phenyl | benzyl | —$CH_2CH_3$ |
| II-3 | PhtN—$(CH_2)_4$— | phenyl | benzyl | —$CH_2CH_2CH_3$ |

TABLE 1-continued

Formula II

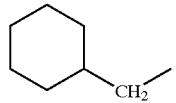

| Compd. No. | R₁ | R₂ | R₃ | R₅ |
|---|---|---|---|---|
| II-4 | PhtN—(CH₂)₄— | phenyl | benzyl | —CH(CH₃)₂ |
| II-5 | PhtN—(CH₂)₄— | phenyl | H | —CH₃ |
| II-6 | PhtN—(CH₂)₄— | phenyl | —CH₃ | —CH₃ |
| II-7 | PhtN—(CH₂)₄— | phenyl | —CH₂CH₃ | —CH₃ |
| II-8 | PhtN—(CH₂)₄— | phenyl | —CH₂CH₂CH₃ | —CH₃ |
| II-9 | PhtN—(CH₂)₄— | phenyl | —CH(CH₃)₂ | —CH₃ |
| II-10 | PhtN—(CH₂)₄— | phenyl | —CH₂CH(CH₃)₂ | —CH₃ |
| II-11 | PhtN—(CH₂)₄— | phenyl | —(CH₂)₃CH₃ | —CH₃ |
| II-12 | PhtN—(CH₂)₄— | phenyl | —CH(CH₃)CH₂CH₃ | —CH₃ |
| II-13 | PhtN—(CH₂)₄— | phenyl | phenyl | —CH₃ |
| II-14 | PhtN—(CH₂)₄— | phenyl | 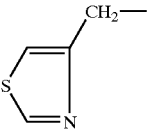 | —CH₃ |
| II-15 | PhtN—(CH₂)₄— | phenyl | 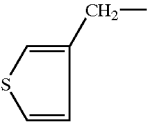 | —CH₃ |
| II-16 | PhtN—(CH₂)₄— | phenyl | 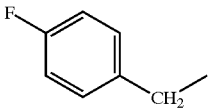 | —CH₃ |
| II-17 | PhtN—(CH₂)₄— | phenyl | 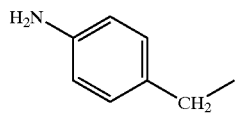 | —CH₃ |
| II-18 | PhtN—(CH₂)₄— | phenyl | 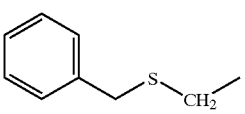 | —CH₃ |
| II-19 | PhtN—(CH₂)₄— | phenyl | 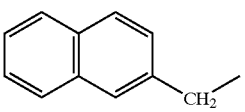 | —CH₃ |
| II-20 | PhtN—(CH₂)₄— | phenyl | | —CH₃ |

TABLE 1-continued
Formula II
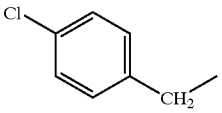
| Compd. No. | R₁ | R₂ | R₃ | R₅ |
|---|---|---|---|---|
| II-21 | PhtN—(CH₂)₄— | phenyl | 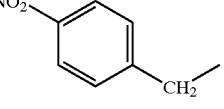 | —CH₃ |
| II-22 | PhtN—(CH₂)₄— | phenyl | 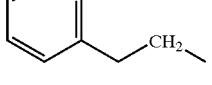 | —CH₃ |
| II-23 | PhtN—(CH₂)₄— | phenyl | 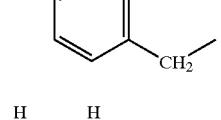 | —CH₃ |
| II-24 | PhtN—(CH₂)₄— | phenyl | 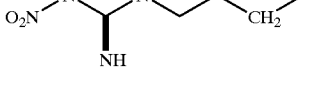 | —CH₃ |
| II-25 | PhtN—(CH₂)₄— | phenyl | 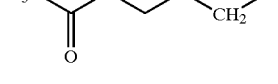 | —CH₃ |
| II-26 | PhtN—(CH₂)₄— | phenyl | 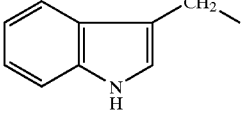 | —CH₃ |
| II-27 | PhtN—(CH₂)₄— | phenyl | 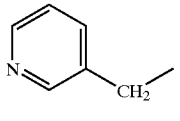 | —CH₃ |
| II-28 | PhtN—(CH₂)₄— | phenyl | 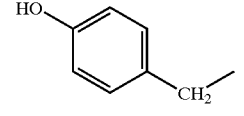 | —CH₃ |
| II-29 | PhtN—(CH₂)₄— | 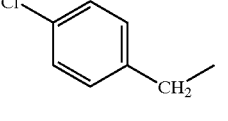 | benzyl | —CH₃ |
| II-30 | PhtN—(CH₂)₄— |  | benzyl | —CH₃ |

TABLE 1-continued

Formula II

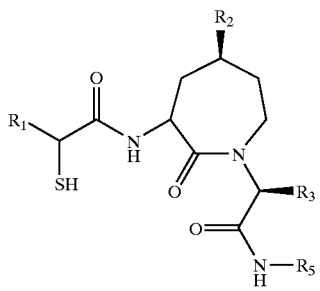

| Compd. No. | R₁ | R₂ | R₃ | R₅ |
|---|---|---|---|---|
| II-31 | PhtN—(CH₂)₄— | 4-NO₂-C₆H₄-CH₂— | benzyl | —CH₃ |
| II-32 | PhtN—(CH₂)₄— | 4-H₂N-C₆H₄-CH₂— | benzyl | —CH₃ |
| II-33 | PhtN—(CH₂)₄— | 4-I-C₆H₄-CH₂— | benzyl | —CH₃ |
| II-34 | PhtN—(CH₂)₄— | cyclohexyl-CH₂— | benzyl | —CH₃ |
| II-35 | PhtN—(CH₂)₄— | 4-F-C₆H₄-CH₂— | benzyl | —CH₃ |
| II-36 | PhtN—(CH₂)₄— | (thiophen-3-yl)-CH₂— | benzyl | —CH₃ |
| II-37 | PhtN—(CH₂)₄— | —CH₃ | benzyl | —CH₃ |
| II-38 | PhtN—(CH₂)₄— | —(CH₂)₃CH₃ | benzyl | —CH₃ |
| II-39 | PhtN—(CH₂)₄— | C₆H₅-CH₂CH₂— | benzyl | —CH₃ |
| II-40 | PhC(O)NH—(CH₂)₃— | C₆H₅-CH₂CH₂— | benzyl | —CH₃ |

TABLE 1-continued

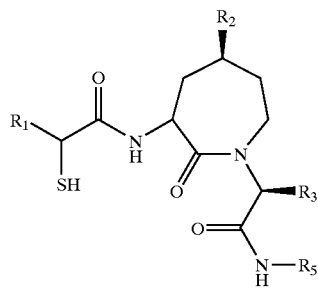

Formula II

| Compd. No. | R₁ | R₂ | R₃ | R₅ |
|---|---|---|---|---|
| II-41 | morpholine-N-C(O)-NH-(CH₂)₃- | phenyl-CH₂CH₂- | benzyl | —CH₃ |
| II-42 | —CH₂CH₂CH₃ | phenyl-CH₂CH₂- | benzyl | —CH₃ |
| II-43 | —CH₂CH₂CH₃ | phenyl-CH₂CH₂- | 3-pyridyl-CH₂- | —CH₃ |
| II-44 | —CH₂CH₂CH₃ | 4-HO-phenyl-CH₂- | benzyl | —CH₃ |
| II-45 | —CH₂CH₂CH₃ | phenyl | benzyl | —CH₃ |
| II-46 | —CH₂CH₂CH₃ | benzyl | benzyl | —CH₃ |
| II-47 | —CH₂CH₂CH₃ | phenyl | benzyl | —CH₂CH₃ |
| II-48 | —CH₂CH₂CH₃ | phenyl | benzyl | —CH₂CH₂CH₃ |
| II-49 | —CH₂CH₂CH₃ | phenyl | benzyl | —(CH₂)₃CH₃ |
| II-50 | —CH₂CH₂CH₃ | phenyl | benzyl | —(CH₂)₄CH₃ |
| II-51 | —CH(CH₃)₂ | phenyl | benzyl | —CH₃ |
| II-52 | —CH(CH₃)₂ | phenyl | benzyl | —CH₂CH₃ |
| II-53 | —CH(CH₃)₂ | phenyl | benzyl | —CH₂CH₂CH₃ |
| II-54 | —CH(CH₃)₂ | phenyl | benzyl | —(CH₂)₃CH₃ |
| II-55 | —CH(CH₃)₂ | phenyl | benzyl | —(CH₂)₄CH₃ |
| II-56 | H₃C—NH—(CH₂)₄— | phenyl | benzyl | —CH₃ |
| II-57 | H₃C—NH—(CH₂)₄— | phenyl | benzyl | —CH₂CH₃ |
| II-58 | (H₃C)₂N—(CH₂)₄— | phenyl | benzyl | —CH₃ |

TABLE 1-continued

Formula II

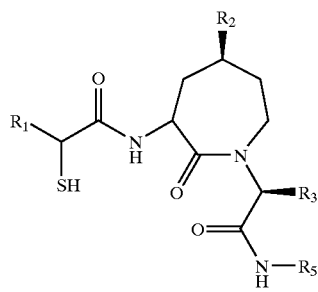

| Compd. No. | R₁ | R₂ | R₃ | R₅ |
|---|---|---|---|---|
| II-59 | 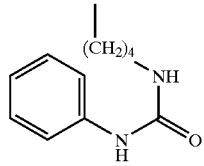 | phenyl | benzyl | —CH₃ |
| II-60 | 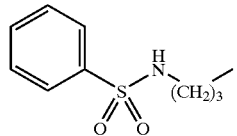 | phenyl | benzyl | —CH₃ |

TABLE 2

Formula III

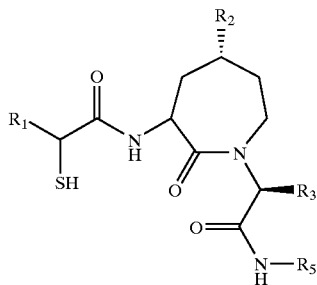

| Compd. No. | R₁ | R₂ | R₃ | R₅ |
|---|---|---|---|---|
| III-1 | PhtN—(CH₂)₄— | phenyl | benzyl | —CH₃ |
| III-2 | PhtN—(CH₂)₄— | phenyl | benzyl | —CH₂CH₃ |
| III-3 | PhtN—(CH₂)₄— | phenyl | benzyl | —CH₂CH₂CH₃ |
| III-4 | PhtN—(CH₂)₄— | phenyl | benzyl | —CH(CH₃)₂ |
| III-5 | PhtN—(CH₂)₄— | phenyl | H | —CH₃ |
| III-6 | PhtN—(CH₂)₄— | phenyl | —CH₃ | —CH₃ |
| III-7 | PhtN—(CH₂)₄— | phenyl | —CH₂CH₃ | —CH₃ |
| III-8 | PhtN—(CH₂)₄— | phenyl | —CH₂CH₂CH₃ | —CH₃ |
| III-9 | PhtN—(CH₂)₄— | phenyl | —CH(CH₃)₂ | —CH₃ |
| III-10 | PhtN—(CH₂)₄— | phenyl | —CH₂CH(CH₃)₂ | —CH₃ |
| III-11 | PhtN—(CH₂)₄— | phenyl | —(CH₂)₃CH₃ | —CH₃ |
| III-12 | PhtN—(CH₂)₄— | phenyl | —CH(CH₃)CH₂CH₃ | —CH₃ |
| III-13 | PhtN—(CH₂)₄— | phenyl | phenyl | —CH₃ |
| III-14 | PhtN—(CH₂)₄— | phenyl | 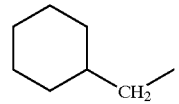 | —CH₃ |

TABLE 2-continued
Formula III
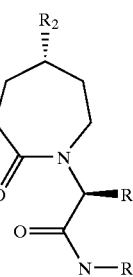
| Compd. No. | R₁ | R₂ | R₃ | R₅ |
|---|---|---|---|---|
| III-15 | PhtN—(CH₂)₄— | phenyl |  | —CH₃ |
| III-16 | PhtN—(CH₂)₄— | phenyl | 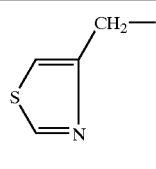 | —CH₃ |
| III-17 | PhtN—(CH₂)₄— | phenyl |  | —CH₃ |
| III-18 | PhtN—(CH₂)₄— | phenyl | 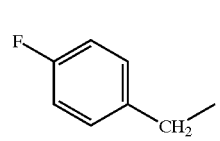 | —CH₃ |
| III-19 | PhtN—(CH₂)₄— | phenyl |  | —CH₃ |
| III-20 | PhtN—(CH₂)₄— | phenyl | 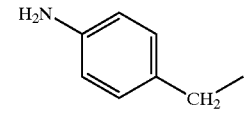 | —CH₃ |
| III-21 | PhtN—(CH₂)₄— | phenyl |  | —CH₃ |
| III-22 | PhtN—(CH₂)₄— | phenyl | 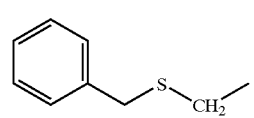 | —CH₃ |
| III-23 | PhtN—(CH₂)₄— | phenyl |  | —CH₃ |

TABLE 2-continued
Formula III
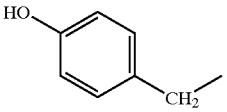
| Compd. No. | R₁ | R₂ | R₃ | R₅ |
|---|---|---|---|---|
| III-24 | PhtN—(CH₂)₄— | phenyl |  | —CH₃ |
| III-25 | PhtN—(CH₂)₄— | phenyl | 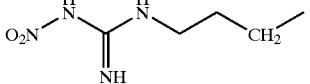 | —CH₃ |
| III-26 | PhtN—(CH₂)₄— | phenyl |  | —CH₃ |
| III-27 | PhtN—(CH₂)₄— | phenyl | 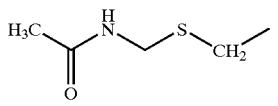 | —CH₃ |
| III-28 | PhtN—(CH₂)₄— | phenyl |  | —CH₃ |
| III-29 | PhtN—(CH₂)₄— | 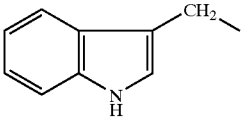 | benzyl | —CH₃ |
| III-30 | PhtN—(CH₂)₄— |  | benzyl | —CH₃ |
| III-31 | PhtN—(CH₂)₄— | 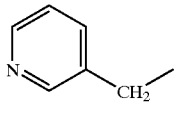 | benzyl | —CH₃ |
| III-32 | PhtN—(CH₂)₄— |  | benzyl | —CH₃ |
| III-33 | PhtN—(CH₂)₄— | 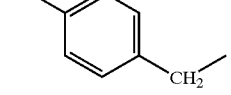 | benzyl | —CH₃ |

TABLE 2-continued
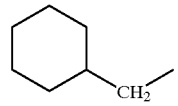
Formula III
| Compd. No. | R₁ | R₂ | R₃ | R₅ |
|---|---|---|---|---|
| III-34 | PhtN—(CH$_2$)$_4$— | 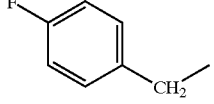 | benzyl | —CH$_3$ |
| III-35 | PhtN—(CH$_2$)$_4$— | 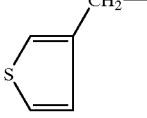 | benzyl | —CH$_3$ |
| III-36 | PhtN—(CH$_2$)$_4$— | 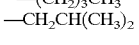 | benzyl | —CH$_3$ |
| III-37 | PhtN—(CH$_2$)$_4$— | —(CH$_2$)$_3$CH$_3$ | benzyl | —CH$_3$ |
| III-38 | PhtN—(CH$_2$)$_4$— | —CH$_2$CH(CH$_3$)$_2$ | benzyl | —CH$_3$ |
| III-39 | PhtN—(CH$_2$)$_4$— |  | benzyl | —CH$_3$ |
| III-40 | 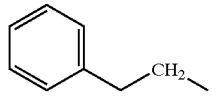 | 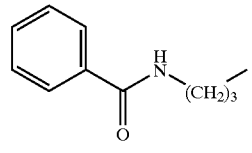 | benzyl | —CH$_3$ |
| III-41 | 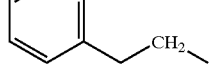 | 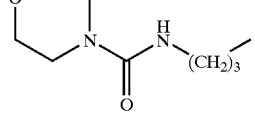 | benzyl | —CH$_3$ |
| III-42 | —CH$_2$CH$_2$CH$_3$ | 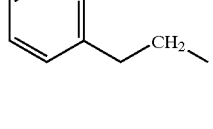 | benzyl | —CH$_3$ |
| III-43 | —CH$_2$CH$_2$CH$_3$ | 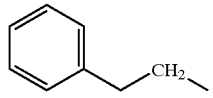 | 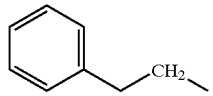 | —CH$_3$ |
| III-44 | —CH$_2$CH$_2$CH$_3$ | 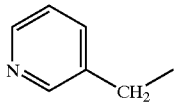 | benzyl | —CH$_3$ |

TABLE 2-continued

Formula III

| Compd. No. | R₁ | R₂ | R₃ | R₅ |
|---|---|---|---|---|
| III-45 | —CH₂CH₂CH₃ | phenyl | benzyl | —CH₃ |
| III-46 | —CH₂CH₂CH₃ | benzyl | benzyl | —CH₃ |
| III-47 | —CH₂CH₂CH₃ | phenyl | benzyl | —CH₂CH₃ |
| III-48 | —CH₂CH₂CH₃ | phenyl | benzyl | —CH₂CH₂CH₃ |
| III-49 | —CH₂CH₂CH₃ | phenyl | benzyl | —(CH₂)₃CH₃ |
| III-50 | —CH₂CH₂CH₃ | phenyl | benzyl | —(CH₂)₄CH₃ |
| III-51 | —CH(CH₃)₂ | phenyl | benzyl | —CH₃ |
| III-52 | —CH(CH₃)₂ | phenyl | benzyl | —CH₂CH₃ |
| III-53 | —CH(CH₃)₂ | phenyl | benzyl | —CH₂CH₂CH₃ |
| III-54 | —CH(CH₃)₂ | phenyl | benzyl | —(CH₂)₃CH₃ |
| III-55 | —CH(CH₃)₂ | phenyl | benzyl | —(CH₂)₄CH₃ |
| III-56 | H₃C—NH—(CH₂)₄— | phenyl | benzyl | —CH₃ |
| III-57 | H₃C—NH—(CH₂)₄— | phenyl | benzyl | —CH₂CH₃ |
| III-58 | (H₃C)₂N—(CH₂)₄— | phenyl | benzyl | —CH₃ |
| III-59 | phenyl-NH-C(O)-NH-(CH₂)₄— | phenyl | benzyl | —CH₃ |
| III-60 | phenyl-SO₂-NH-(CH₂)₃— | phenyl | benzyl | —CH₃ |

Another embodiment of the novel compounds is that of formula (1) wherein X is N and $R_8$ is hydrogen.

In a class of this embodiment, $R_1$ is $C_1$–$C_6$ alkyl, preferably methyl, ethyl, propyl, isopropyl, butyl or isobutyl; $R_2$ is $C_1$–$C_4$ alkyl, a —(CH₂)$_p$—Ar₁ group wherein Ar₁ is phenyl optionally substituted with F, Cl, $C_1$–$C_4$ alkyl, or W—OR₇ or is a —(CH₂)$_p$—($C_3$–$C_9$)heteroaryl group wherein the ($C_3$–$C_9$)heteroaryl group is thienyl, 2-pyridyl or thiazolyl; $R_4$ is hydrogen; $R_5$ is hydrogen, methyl, ethyl, propyl, isopropyl, butyl or isobutyl.

In another class of this embodiment, $R_1$ is a W—(CH₂)— group; $R_2$ is $C_1$–$C_4$ alkyl, a —(CH₂)$_p$—Ar₁ group wherein Ar₁ is phenyl optionally substituted with F, Cl, $C_1$–$C_4$ alkyl, or —OR₇ or is a —(CH₂)$_p$—($C_3$–$C_9$)heteroaryl group wherein the ($C_3$–$C_9$)heteroaryl group is thienyl, 2-pyridyl or thiazolyl; $R_4$ is hydrogen; $R_5$ is hydrogen, methyl, ethyl, propyl, isopropyl, butyl or isobutyl.

In another class of this embodiment, $R_1$ is a Q—Z—(H₂)$_m$— group; $R_2$ is $C_1$–$C_4$ alkyl, a —(CH₂)$_p$—Ar₁ group wherein Ar is phenyl optionally substituted with F, Cl, $C_1$–$C_4$ alkyl, or —OR₇ or is a —(CH₂)$_p$—($C_3$–$C_9$)heteroaryl group wherein the ($C_3$–$C_9$)heteroaryl group is thienyl, 2-pyridyl or thiazolyl; $R_4$ is hydrogen; $R_5$ is hydrogen, methyl, ethyl, propyl, isopropyl, butyl or isobutyl.

Exemplifying this embodiment are the following compounds of the Formula IV shown in Table 3:

TABLE 3

Formula IV

| Compd. No. | $R_1$ | $R_2$ | $R_3$ | $R_5$ |
|---|---|---|---|---|
| IV-1 | PhtN—(CH$_2$)$_4$— | benzyl | benzyl | —CH$_3$ |
| IV-2 | PhtN—(CH$_2$)$_4$— | benzyl | benzyl | —CH$_2$CH$_3$ |
| IV-3 | PhtN—(CH$_2$)$_4$— | benzyl | benzyl | —CH(CH$_3$)$_2$ |
| IV-4 | PhtN—(CH$_2$)$_4$— | benzyl | H | —CH$_3$ |
| IV-5 | PhtN—(CH$_2$)$_4$— | benzyl | —CH$_3$ | —CH$_3$ |
| IV-6 | PhtN—(CH$_2$)$_4$— | benzyl | —CH(CH$_3$)$_2$ | —CH$_3$ |
| IV-7 | PhtN—(CH$_2$)$_4$— | benzyl | —CH$_2$CH(CH$_3$)$_2$ | —CH$_3$ |
| IV-8 | PhtN—(CH$_2$)$_4$— | benzyl | phenyl | —CH$_3$ |
| IV-9 | PhtN—(CH$_2$)$_4$— | benzyl | cyclohexyl-CH$_2$— | —CH$_3$ |
| IV-10 | PhtN—(CH$_2$)$_4$— | benzyl | (thiophen-3-yl)-CH$_2$— | —CH$_3$ |
| IV-11 | PhtN—(CH$_2$)$_4$— | benzyl | (4-aminophenyl)-CH$_2$— | —CH$_3$ |
| IV-12 | PhtN—(CH$_2$)$_4$— | benzyl | PhCH$_2$—S—CH$_2$— | —CH$_3$ |
| IV-13 | PhtN—(CH$_2$)$_4$— | benzyl | (4-chlorophenyl)-CH$_2$— | —CH$_3$ |
| IV-14 | PhtN—(CH$_2$)$_4$— | benzyl | Ph-CH$_2$CH$_2$— | —CH$_3$ |
| IV-15 | PhtN—(CH$_2$)$_4$— | benzyl | (4-hydroxyphenyl)-CH$_2$— | —CH$_3$ |
| IV-16 | PhtN—(CH$_2$)$_4$— | benzyl | O$_2$N—NH—C(=NH)—NH—CH$_2$CH$_2$CH$_2$— | —CH$_3$ |

TABLE 3-continued
Formula IV
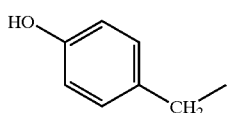
| Compd. No. | R₁ | R₂ | R₃ | R₅ |
|---|---|---|---|---|
| IV-17 | PhtN—(CH₂)₄— | benzyl | 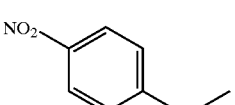 | —CH₃ |
| IV-18 | PhtN—(CH₂)₄— | 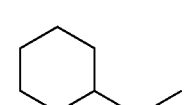 | benzyl | —CH₃ |
| IV-19 | PhtN—(CH₂)₄— | 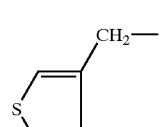 | benzyl | —CH₃ |
| IV-20 | PhtN—(CH₂)₄— | 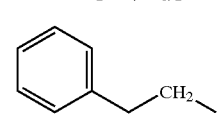 | benzyl | —CH₃ |
| IV-21 | PhtN—(CH₂)₄— | 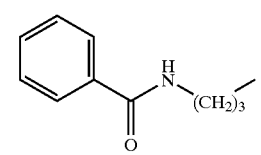 | benzyl | —CH₃ |
| IV-22 | PhtN—(CH₂)₄— | —(CH₂)₃CH₃ | benzyl | —CH₃ |
| IV-23 | PhtN—(CH₂)₄— | —CH₂CH(CH₃)₂ | benzyl | —CH₃ |
| IV-24 | PhtN—(CH₂)₄— | 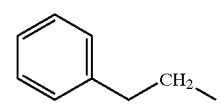 | benzyl | —CH₃ |
| IV-25 | 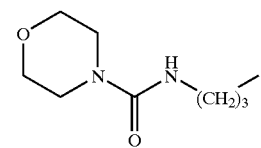 | 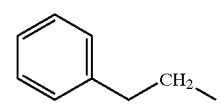 | benzyl | —CH₃ |
| IV-26 | 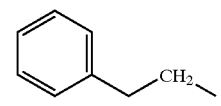 | 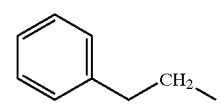 | benzyl | —CH₃ |
| IV-27 | —CH₂CH₂CH₃ | 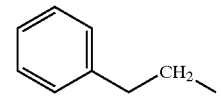 | benzyl | —CH₃ |

TABLE 3-continued

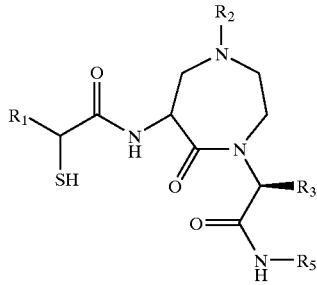

Formula IV

| Compd. No. | R₁ | R₂ | R₃ | R₅ |
|---|---|---|---|---|
| IV-28 | —CH₂CH₂CH₃ | benzyl | benzyl | —CH₃ |
| IV-29 | —CH₂CH₂CH₃ | HO-C₆H₄-CH₂— (4-hydroxybenzyl) | benzyl | —CH₃ |
| IV-30 | —CH₂CH₂CH₃ | benzyl | benzyl | —CH₂CH₃ |
| IV-31 | —CH(CH₃)₂ | benzyl | benzyl | —CH₃ |
| IV-32 | —CH(CH₃)₂ | benzyl | benzyl | —CH₂CH₃ |
| IV-33 | —CH(CH₃)₂ | benzyl | benzyl | —CH₂CH₂CH₃ |
| IV-34 | H₃C—NH—(CH₂)₄— | benzyl | benzyl | —CH₃ |
| IV-35 | H₃C—NH—(CH₂)₄— | benzyl | benzyl | —CH₂CH₃ |
| IV-36 | (H₃C)₂N—(CH₂)₄— | benzyl | benzyl | —CH₃ |
| IV-37 | Ph-NH-C(O)-NH-(CH₂)₄— | benzyl | benzyl | —CH₃ |
| IV-38 | Ph-SO₂-NH-(CH₂)₃— | benzyl | benzyl | —CH₃ |

Another embodiment of the novel compounds is that of formula (1) wherein $R_8$ is $R_8'$ and is defined as —C(O)R₇, a —(O)—(CH₂)$_q$—K group or a —S—G group.

In a class of this embodiment, $R_1$ is $C_1$–$C_6$ alkyl, preferably methyl, ethyl, propyl, isopropyl, butyl or isobutyl; $R_2$ is $C_1$–$C_4$ alkyl, a —(CH₂)$_p$—Ar₁ group wherein Ar₁ is phenyl optionally substituted with F, Cl, $C_1$–$C_4$ alkyl, or —OR₇ or is a —(CH₂)$_p$—($C_3$–$C_9$)heteroaryl group wherein the ($C_3$–$C_9$)heteroaryl group is thienyl, 2-pyridyl or thiazolyl; $R_4$ is hydrogen; $R_5$ is hydrogen, methyl, ethyl, propyl, isopropyl, butyl or isobutyl.

In another class of this embodiment, $R_1$ is a W—(CH₂)— group; $R_2$ is $C_1$–$C_4$ alkyl, a —(CH₂)$_p$—Ar₁ group wherein Ar₁ is phenyl optionally substituted with F, Cl, $C_1$–$C_4$ alkyl, or —OR₇ or is a —(CH₂)$_p$—($C_3$–$C_9$)heteroaryl group wherein the ($C_3$–$C_9$)heteroaryl group is thienyl, 2-pyridyl or thiazolyl; $R_4$ is hydrogen; $R_5$ is hydrogen, methyl, ethyl, propyl, isopropyl, butyl or isobutyl.

In another class of this embodiment, $R_1$ is a Q—Z—(H₂)$_m$— group; $R_2$ is $C_1$–$C_4$ alkyl, a —(CH₂)$_p$—Ar₁ group wherein Ar is phenyl optionally substituted with F, Cl, $C_1$–$C_4$ alkyl, or —$OR_7$ or is a —$(CH_2)_p$—$(C_3$–$C_9)$heteroaryl group wherein the $(C_3$–$C_9)$heteroaryl group is thienyl, 2-pyridyl or thiazolyl; $R_4$ is hydrogen; $R_5$ is hydrogen, methyl, ethyl, propyl, isopropyl, butyl or isobutyl.

In another class of this embodiment, K is

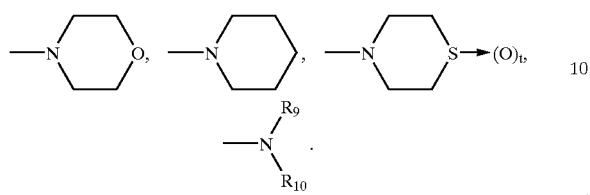

In another class of this embodiment, G is

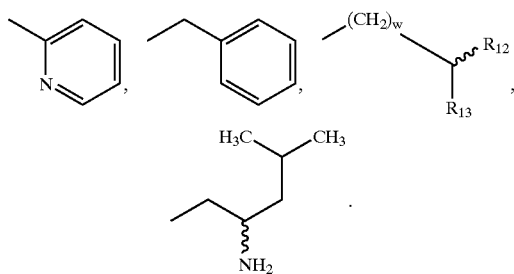

Exemplifying this embodiment are the following compounds disclosed below:

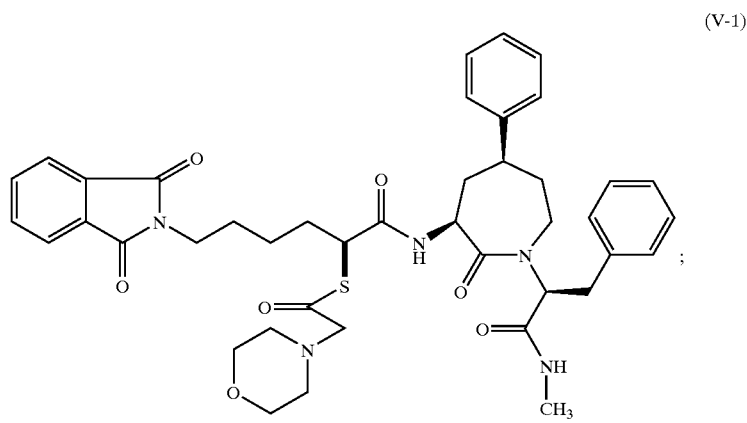

(V-1)

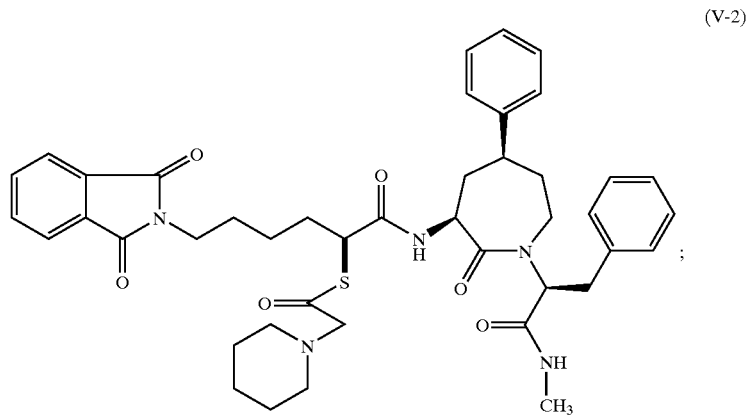

(V-2)

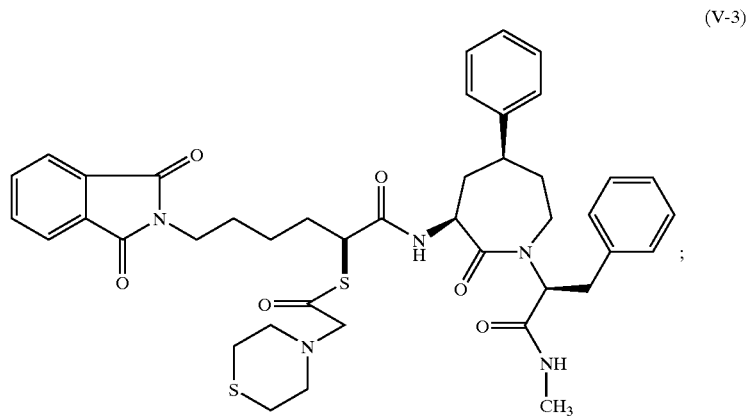

(V-3)

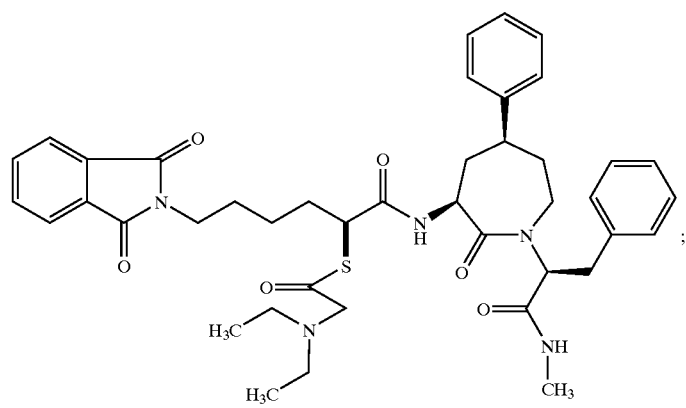
(V-4)
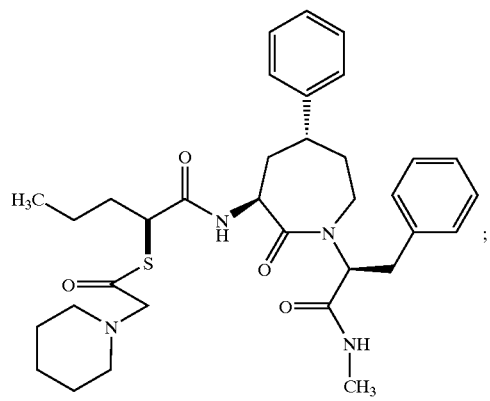
(V-5)
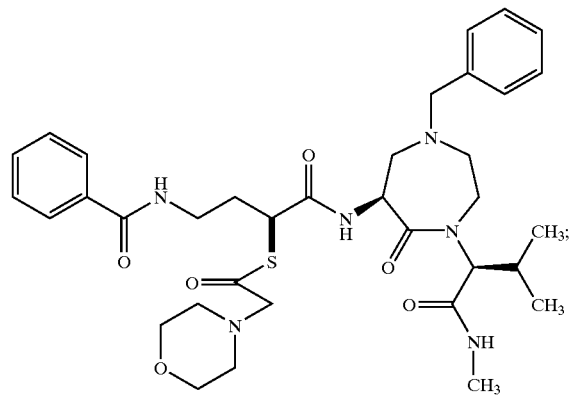
(V-6)
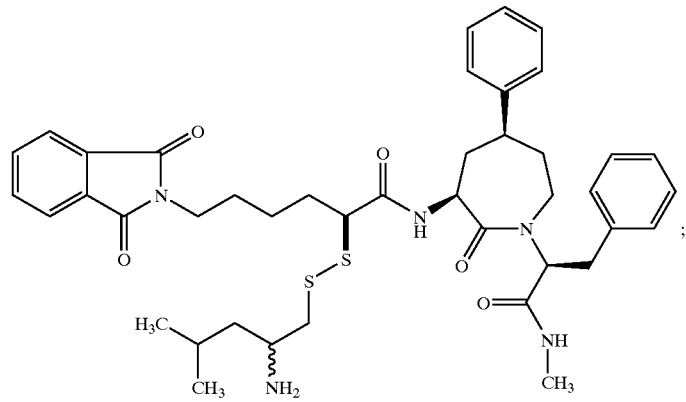
(V-7)

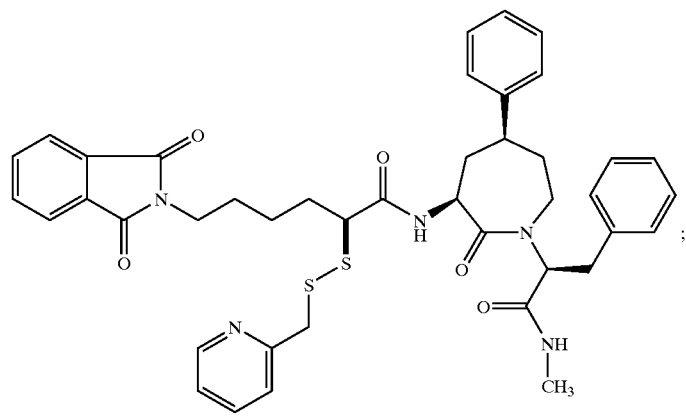
(V-8)
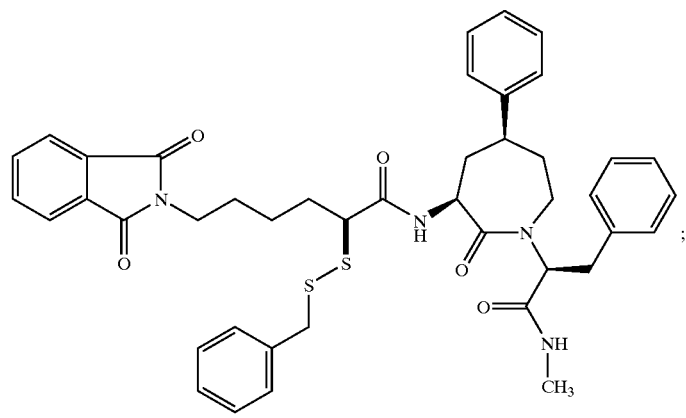
(V-9)
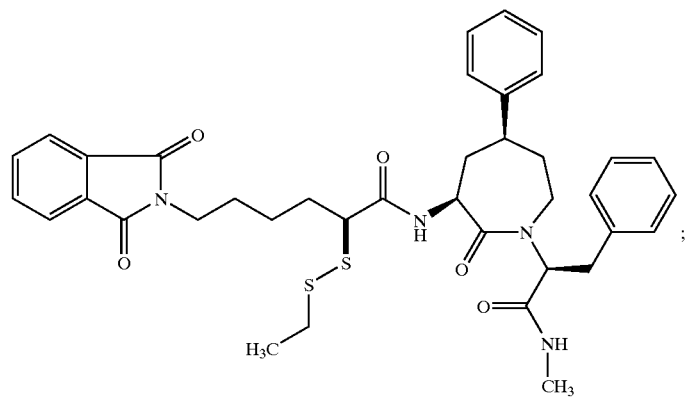
(V-10)
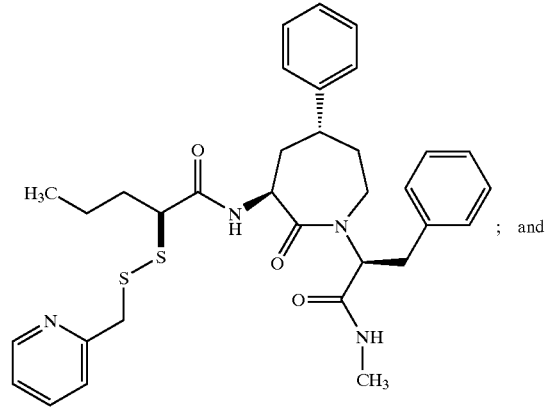
; and
(V-11)

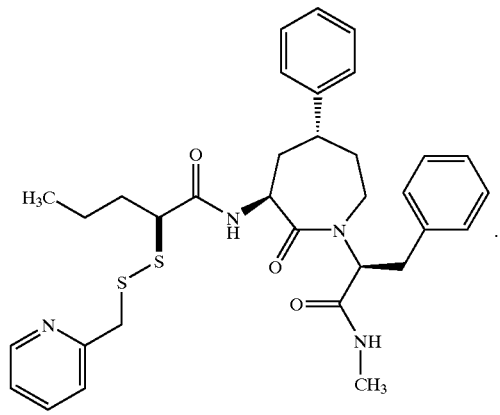
(V-12)
The compounds of formula (1) wherein X is CH can be prepared by utilizing techniques and procedures well known and appreciated by one of ordinary skill in the art. A general synthetic scheme for preparing these compounds is set forth in Scheme A wherein all substituents are as previously defined unless otherwise indicated.
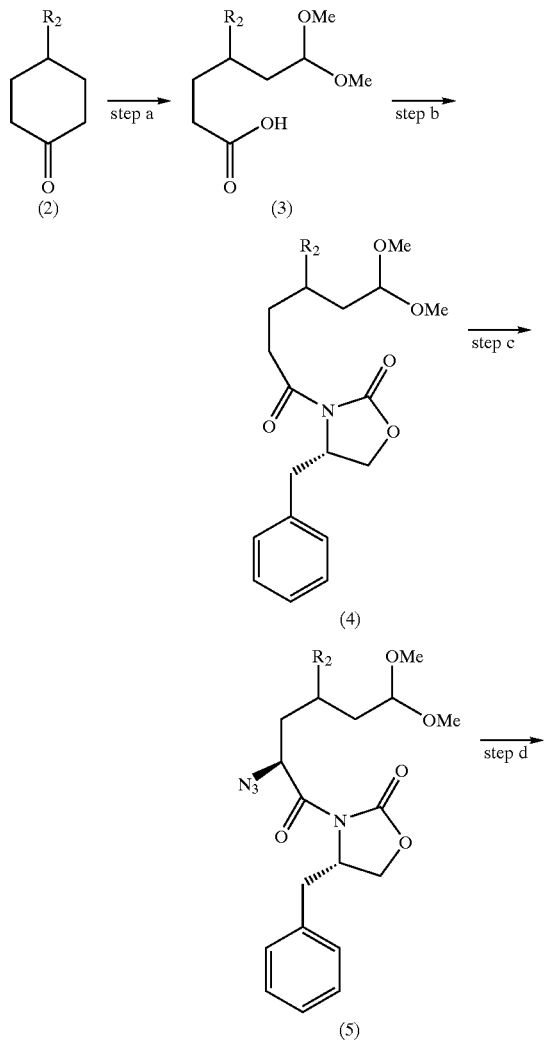

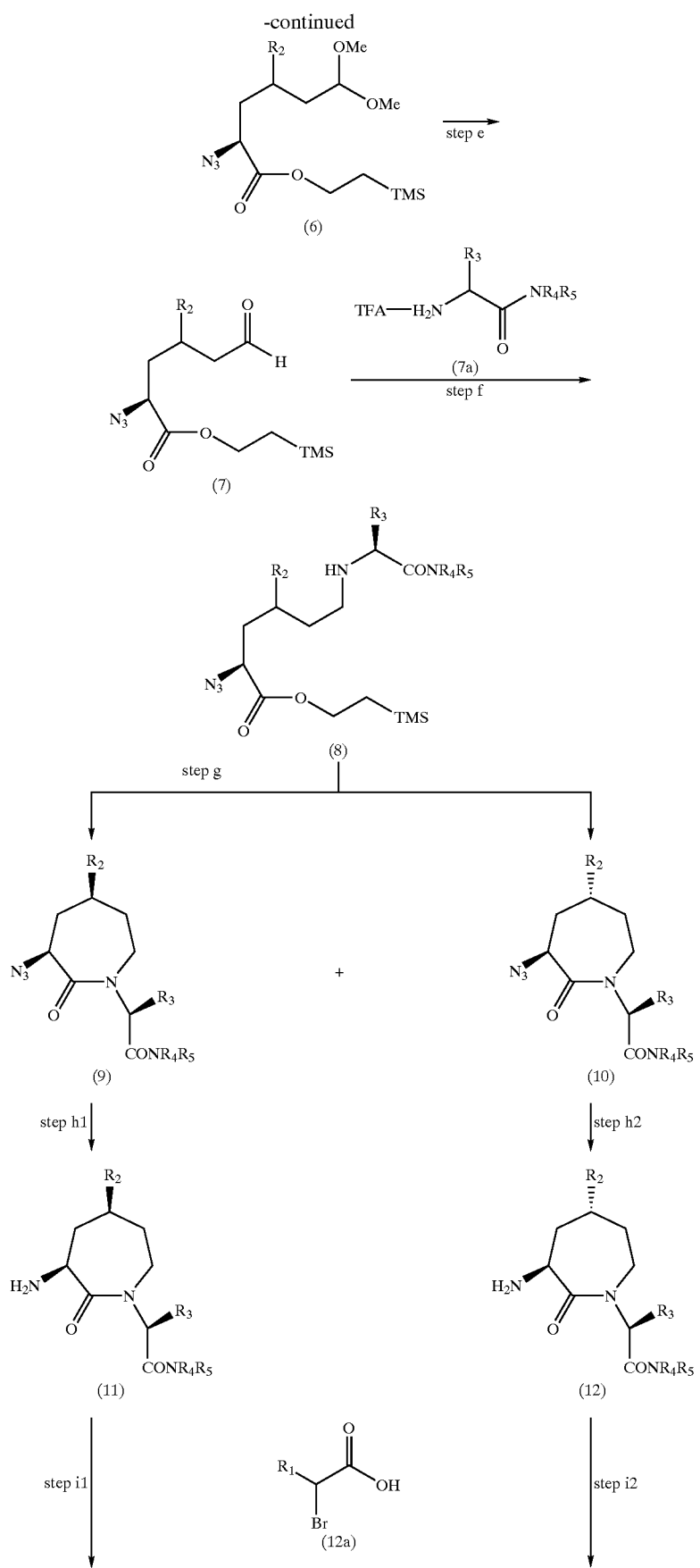

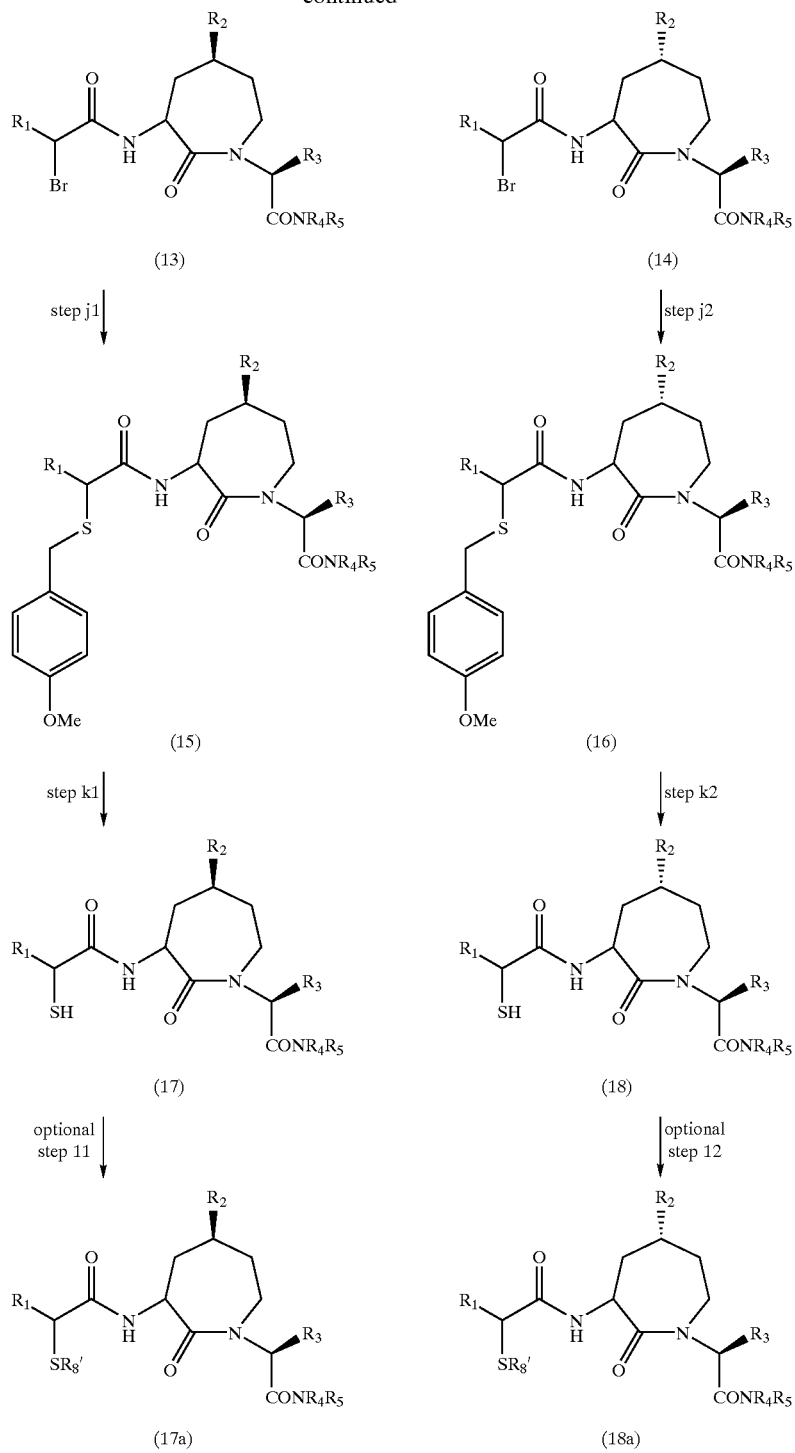

Scheme A provides a general synthetic procedure for preparing compounds of formula (1) wherein X is CH, that is, compounds of structures (17), (17a), (18) and (18a). The substituents $R_1$, $R_2$, $R_3$, $R_4$ and $R_5$ are defined as above, while the substituent $R_8'$ is defined as —C(O)$R_7$. The term "Me" stands for methyl, the term "PhtN" stands for phthalimido, "TMS" stands for trimethylsilyl and the term ""TFA" signifies a trifluoroacetic acid salt.

In Scheme A, step a, the appropriate $R_2$-substituted cyclohexanone of structure (2) is enolized with a non-nucleophilic base and quenched with a suitable electrophile, such as chlorotrimethylsilane, to form the corresponding $R_2$-substituted enol ether, followed by treatment with ozone, dimethylsulfide, trimethylortho-formate and a suitable base to provide the appropriate $R_2$-substituted acid of structure (3).

For example, lithium diisopropylamide (LDA) is generated by the addition of n-butyllithium to di-isopropylamine in the presence of a suitable organic solvent such as tetrahydrofuran (THF). A solution of $R_2$-substituted cyclohexanone of structure (2) in a suitable organic solvent, such as THF, is then added at −78° C. After a period of time ranging from about 1 to 3 hours, the reaction is quenched with chloromethylsilane and the mixture is stirred followed by extraction and concentration of the organic layer to yield the silyl enol ether intermediate.

The silyl enol ether intermediate is then dissolved in a suitable organic solvent or solvent mixture, such as a methylene chloride/methanol mixture, cooled to −78° C. and treated with ozone. Dimethyl sulfide is added and the reaction mixture is allowed to warm gradually to ambient temperature over a period of time ranging from 10 to 20 hours. The solution is then concentrated and treated with an orthoformate reagent such as trimethylorthoformate and an acid source such as acetyl chloride and heated to reflux. After a period of time ranging from 4 to 6 hours, the mixture is cooled to ambient temperature and treated with a suitable base, such as potassium hydroxide. The appropriate $R_2$-substituted acid of structure (3) can be isolated by methods well known and appreciated in the art, such as extraction and evaporation.

In Scheme A, step b, the appropriate $R_2$-substituted acid of structure (3) is reacted with lithiated (S)-4-benzyl-2-oxazolidinone to provide the appropriate acyloxazolidinone of structure (4).

For example, the appropriate $R_2$-substituted acid of structure (3) in a suitable organic solvent, such as tetrahydrofuran, is treated with a suitable tertiary organic amine such as triethylamine or N-methylmorpholine and cooled to −78° C. A suitable acid halide such as trimethylacetyl chloride is added and the mixture is transferred to an ice bath for 0.5 to 1.0 hours, then recooled to −78° C. The resulting slurry is treated with lithiated (S)-4-benzyl-2-oxazolidinone, prepared by adding n-butyllithium to (S)-4-benzyl-2-oxazolidinone in tetrahydrofuran, and allowed to warm gradually to ambient temperature over a period of time ranging from about 10 to 20 hours. The appropriate acyloxazolidinone of structure (4) can be isolated by methods well known and appreciated in the art, such as extraction and evaporation. The product can be purified by methods well known and appreciated in the art, such as flash chromatography.

In Scheme A, step c, the appropriate acyloxazolidinone of structure (4) undergoes an azide alkylation reaction with a suitable azide transfer agent to provide the appropriate α-azidoacyloxazolidinone of structure (5).

For example, a solution of a suitable amide such as potassium bis(trimethylsilyl)amide in a suitable organic solvent, such as tetrahydrofuran, is cooled to −78° C. and treated with a solution of the appropriate acyloxazolidinone of structure (4) in tetrahydrofuran, precooled to −78° C. A solution of a suitable azide transfer agent, such as triisopropylbenzenesulfonyl azide, in a suitable organic solvent, such as THF, precooled to −78° C. is then added. The solution is stirred, quenched with acetic acid and transferred to an oil bath having a temperature of from about 2540° C. After a period of time ranging from about 1 to 2 hours, the suspension is cooled to ambient temperature and water is added to obtain a solution. The appropriate α-azidoacyloxazolidinone of structure (5) can be isolated by methods well known and appreciated in the art, such as extraction and evaporation. The product can be purified by methods well known in the art, such as flash chromatography.

In Scheme A, step d, the appropriate α-azidoacyloxazolidinone of structure (5) is converted to the corresponding α-azidoacid and then reacted with 2-trimethylsilylethanol to give the corresponding α-azidoester of structure (6).

For example, the appropriate α-azidoacyloxazolidinone of structure (5) in a suitable solvent such as tetrahydrofuran or tetrahydrofuran/water mixtures, is cooled and treated with hydrogen peroxide and a suitable base, such as lithium hydroxide. The mixture is stirred for about 1 to 2 hours and allowed to warm to ambient temperature and treated with $Na_2SO_3$. The corresponding α-azidoacid is isolated by methods well known and appreciated in the art, such as extraction and evaporation.

The corresponding α-azidoacid in a suitable organic solvent, such as tetrahydrofuran, is then treated sequentially at ambient temperature with 2-trimethylsilylethanol an organic amine, such as pyridine, and a condensing such as 1-(3-dimethylaminopropyl)-3-ethylcarbodiimide hydrochloride (EDC). The mixture is then stirred for about 1 to 3 days and then concentrated. The corresponding α-azidoester of structure (6) can be isolated by methods well known and appreciated in the art, such as extraction and evaporation. The product can be purified by methods well known and appreciated in the art, such as flash chromatography.

In Scheme A, step e, the α-azidoester of structure (6) is contacted with a suitable organic acid to provide the corresponding aldehyde-ester of structure (7).

For example, a solution of α-azidoester of structure (6) in the presence of an suitable organic acid, such as acetic acid, and a suitable organic solvent, such as a tetrahydrofuran/water mixture, is heated at a temperature ranging from about 55° C. to about 70° C. for about 3 to 5 hours. The solution is then cooled and the corresponding aldehyde-ester of structure (7) is isolated by methods well known and appreciated in the art, such as extraction and evaporation. The product can be purified by methods well known and appreciated in the art, such as flash chromatography.

In Scheme A, step f, the aldehyde-ester of structure (7) is coupled with the $R_3$-substituted amine salt of structure (7a) to provide the corresponding amino-ester of structure (8).

For example, a solution of the aldehyde ester of structure (7) and $R_3$-substituted amine salt of structure (7a) in a hydroxylic solvent, such as methanol or ethanol, is treated with powdered activated 3A sieves. After about 30 minutes to 1 hour, the solution is reacted with a suitable reducing agent such as sodium cyanoborohydride, lithium cyanoborohydride, and the like. The amino-ester of structure (8) is isolated by methods well known and appreciated in the art, such as extraction and evaporation. The product can be purified by methods well known and appreciated in the art, such as flash chromatography.

In Scheme A, step g, the amino-ester of structure (8) is cyclized to give a mixture of the cis α-azidolactam of structure (9) and the trans α-azidolactam of structure (10).

For example, a solution of the amino-ester of structure (8) in a suitable organic solvent, such as tetrahydrofuran, is treated at ambient temperature with a fluoride ion source, such as tetra-n-butylammonium fluoride, and stirred. After about 2 to 4 hours, the solution is concentrated. The residue is then dissolved in a suitable organic solvent, such as ethyl acetate, washed with a suitable acid, such as 10% aqueous hydrochloric acid, and brine. The organic layer is then dried and concentrated to yield the corresponding crude amino acid.

The crude amino acid is then dissolved in a suitable organic solvent, such as tetrahydrofuran, cooled in an ice bath and treated sequentially with a suitable tertiary amine, such as N-methylmorpholine, and isobutyl chloroformate. The suspension is stirred for about 2 to 3 hours and filtered. The salts are washed with dry tetrahydrofuran and the filtrate is concentrated. The residue may be purified by methods well known and appreciated in the art, such as radial chromatography, to afford separately, the cis α-azidolactam of structure (9) and the trans α-azidolactam of structure (10).

In Scheme A, steps h1 and h2, the cis α-azidolactam of structure (9) and the trans α-azidolactam of structure (10), respectively, are converted to the corresponding cis α-aminolactam of structure (11) and the trans α-aminolactam of structure (12), respectively.

For example, a solution of cis α-azidolactam of structure (9) or trans α-azidolactam of structure (10) in a protic solvent, such as methanol or ethanol, is degassed and treated with an alkyl dithiol, such as 1,3-propanedithiol and a tertiary amine, such as triethylamine. The solution is stirred from 60 to 72 hours and then concentrated. The residue may be purified by methods well known and appreciated in the art, such as flash chromatography, to afford the corresponding cis α-aminolactam of structure (11) or the trans α-aminolactam of structure (12), respectively.

In Scheme A, steps i1 and i2, the cis α-aminolactam of structure (11) and the trans α-aminolactam of structure (12), respectively, are coupled with the bromoacid of structure (12a) to provide the bromoamides of structures (13) and (14), respectively.

For example, a mixture of cis α-aminolactam of structure (11) or trans α-aminolactam of structure (12), a bromoacid of structure (12a), a carbodiimide, such as as 1-(3-dimethylaminopropyl)-3-ethylcarbodiimide hydrochloride (EDC), and 1-hydroxybenzotriazole (HOBt) in a suitable organic solvent such as methylene chloride was stirred at ambient temperature for 15 to 25 hours. The cis bromoamide of structure (13) or the trans bromoamide of structure (14) may be isolated by methods well known and appreciated in the such, as extraction and evaporation. The product can be purified by methods well known and appreciated in the art, such as flash chromatography.

In Scheme A, steps j1 and j2, the cis bromoamide of structure (13) and the trans bromoamide of structure (14), respectively, are converted to the cis α-thioamide of structure (15) and the trans α-thioamide of structure (16), respectively.

For example, a solution of p-methoxybenzylmercaptan in a suitable organic solvent such as dimethylformamide is degassed and treated with a suitable base such as sodium hydride. After about 1 to 2 hours, a solution of bromoamide of structure (13) or structure (14) in a suitable organic solvent, such as dimethylformamide is added to the mercaptide formed immediately above, as well as a suitable phase transfer catalyst, such as tetra-n-butylammonium iodide. The reaction mixture is stirred for 15 to 25 hours and saturated aqueous ammonium chloride solution and water are added. The cis α-thioamide of structure (15) or the trans α-thioamide of structure (16), respectively, may be isolated by methods well known and appreciated in the art, such as extraction and evaporation. The product can be purified by methods well known and appreciated in the art, such as flash chromatography.

In Scheme A, steps k1 and k2, cis α-thioamide of structure (15) and the trans α-thioamide of structure (16), respectively, are cleaved to provide the compounds of structures (17) and (18), respectively, which represent the compounds of formula (1) where X is CH.

For example, a mixture of cis α-thioamide of structure (15) or the trans α-thioamide of structure (16), mercuric acetate and anisole in a suitable organic solvent, such as methylene chloride is cooled in an ice bath, degassed, and treated with a suitable acid, such as trifluoroacetic acid. After a time period of about 3–6 hours, hydrogen sulfide gas is bubbled in the reaction mixture for about 10 to 20 minutes. The compounds of structures (17) and (18), which represent the compounds of formula (1) where X is CH, may be isolated by methods well known and appreciated in the art, such as extraction and evaporation. The product can be purified by methods well known and appreciated in the art, such as flash chromatography.

In Scheme A, optional steps 11 and 12, the thiol functionality of compounds (17) and (18) are acylated with an $R_8'$-acylating agent, wherein $R_8'$ is defined as above, to provide the compounds (17a) and (18a).

For example, the appropriate compound of structures (17) or (18) can be contacted with a molar equivalent of an appropriate $R_8'$-acylating agent such as acetic anhydride and a catalytic amount of an acid such as sulfuric acid. The reactants are typically stirred together for a period of time ranging from 10 minutes to 10 hours. The compounds of structures (17a) and (18a) may be isolated by methods well known and appreciated in the art, such as extraction and evaporation. The products can be purified by methods well known and appreciated in the art, such as flash chromatography.

The $R_2$-substituted cyclohexanones of structure (2) can be prepared by utilizing techniques and procedures well known and appreciated by one of ordinary skill in the art. A general synthetic scheme for preparing these compounds is set forth in Scheme A1 wherein all substituents are as previously defined unless otherwise indicated.

SCHEME A1

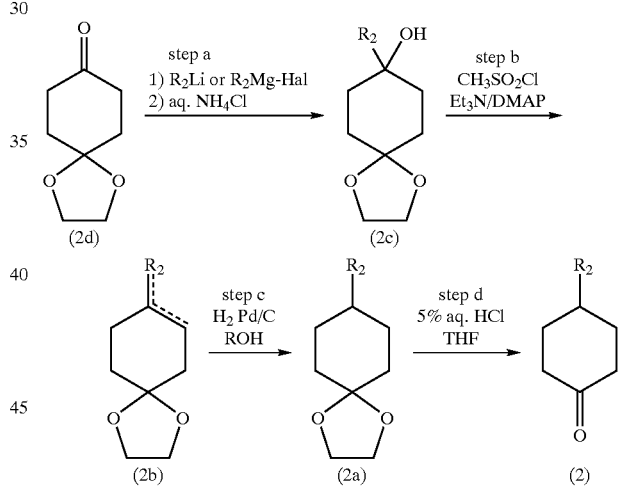

Scheme A1 provides a general synthetic procedure for preparing compounds of formula (2) wherein the substituents are defined as above, unless otherwise indicated.

In Scheme A1, step a, the ketone of structure (2d) is reacted with an organolithium compound of the formula $R_2Li$ or a Grignard reagent of the formula $R_2Mg$—Hal, where "Hal" is halogen, according to techniques well known in the art to provide the tertiary alcohol of structure (2c).

For example, an appropriate Grignard reagent of structure $R_2MgBr$ in a suitable organic solvent, such as ethyl ether is added to a solution of the ketone of structure (2d) in a suitable organic solvent, such as anhydrous ethyl ether. The reaction mixture is stirred and then cooled to about 0° C. Saturated ammonium chloride solution is then added. The ethereal layer is separated, washed with water and dried ($MgSO_4$). The solvent is evaporated in vacuo and purified by silica gel chromatography to give the tertiary alcohol of structure (2c).

49

An appropriate Grignard reagent of structure $R_2Mg$—Hal can be prepared by techniques well known in the art. For example, magnesium turnings and anhydrous ethyl ether are mixed under an inert atmosphere. A solution of a compound of the formula $R_2$-Hal, where Hal is halogen, in ethyl ether is then added to the magnesium mixture. The mixture is then stirred until the magnesium metal dissolves to give the Grignard reagent of structure $R_2Mg$—Hal.

In Scheme A1, step b, the tertiary alcohol of structure (2c) is dehydrated according to techniques well known in the art to give the intermediate of structure (2b).

For example, the tertiary alcohol of structure (2c) may be dehydrated according to the procedure disclosed by Yadav, J. S. and Mysorekar, S. V., *Synth. Comm.* 19, 1057–1060 (1989). For example, to a stirred solution of the tertiary alcohol of structure (2c) in methylene chloride is added triethylamine and DMAP. The mixture is then cooled to about 0° C. and methanesulfonyl chloride is added dropwise to the mixture. The resulting reaction mixture is stirred for about 1 hour at room temperature. Crushed ice is added and the mixture stirred for about 1 hour. Afterwards, the reaction mixture is extracted with methylene chloride. The organic extracts are combined, washed with water and dried ($Na_2SO_4$). The solvent is then evaporated and the products are purified by methods well known and appreciated in the art, such as silica gel chromatography to provide the intermediate of structure (2b).

In Scheme A1, step c, the intermediate of structure (2b) is reduced to provide the ketal of structure (2a).

For example, a solution of the intermediate of structure (2b) in a suitable organic solvent, such as methanol, may be treated with 10% palladium/carbon catalyst (Pd—C) and stirred under a hydrogen atmosphere for a period of from 10–20 hours. Additional catalyst may then be added, the mixture may be stirred for an additional 5–10 hours, degassed and filtered. The filtrate is then concentrated to yield the ketal of structure (2a).

In Scheme A1, step d, the ketal of structure (2a) is hydrolyzed according to procedures well known in the art to provide the $R_2$-substituted cyclohexanone of structure (2). For example, the blocked ketone functionality of the compound of structure (2a) may be hydrolyzed according to the procedure disclosed by Honan, M. C., *Tetrahedron Lett.* 26, 6393–6396 (1985) or Greico, P. A. et al., *J. Amer. Chem. Soc.* 99, 5773–5780 (1977). For example, the ketal of structure (2a) is dissolved in a solution of a tetrahydrofuran/5% hydrochloric acid mixture (2:1) and allowed to react for a period of time ranging from about 15 to 25 hours at room temperature. The solvent is then removed under reduced pressure to afford the $R_2$-substituted cyclohexanone of structure (2).

The compounds of formula (1) wherein X is N can be prepared by utilizing techniques and procedures well known and appreciated by one of ordinary skill in the art. A general synthetic scheme for preparing these compounds is set forth in Scheme B wherein all substituents are as previously defined unless otherwise indicated.

50

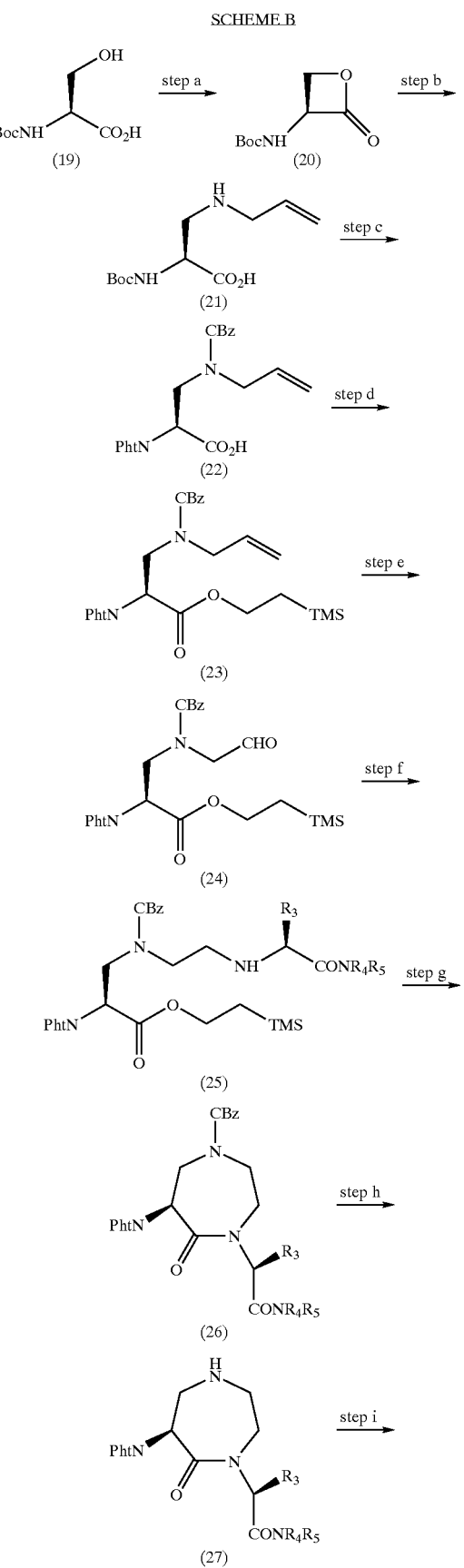

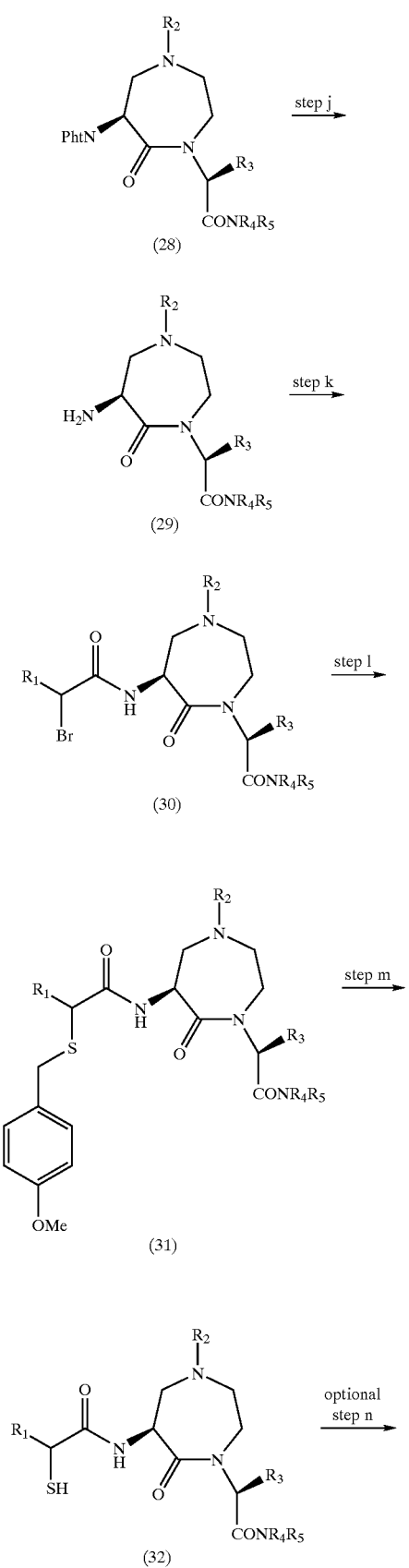

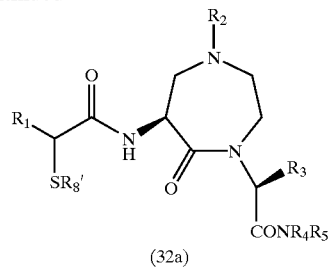

(32a)

Scheme B provides a general synthetic procedure for preparing compounds of formula (1) wherein X is N, that is, compounds of structures (32) and (32a). The substituents $R_1$, $R_2$, $R_3$, $R_4$, $R_5$, $R_8'$, Me, Phth, Boc and TFA are defined as above. The term "TMS" represents trimethylsilyl.

In Scheme B, step a, N-tert-butoxycarbonyl-L-serine (19) is converted to N-tert-butoxycarbonyl-L-serine β-lactone (20).

For example, N-tert-butoxycarbonyl-L-serine (19) is converted to N-tert-butoxycarbonyl-L-serine β-lactone (20) using techniques and procedures well known in the art. For example, N-tert-butoxycarbonyl-L-serine (19) may be reacted with diethyl azodicarboxylate (DEAD) and triphenylphosphine ($Ph_3P$) under Mitsunobu conditions or as described in Pansare, S. V. et al., Org. Synth. 70, 10 (1991) to provide N-tert-butoxycarbonyl-L-serine β-lactone (20). The product may be isolated by well known techniques such as extraction and evaporation and may be purified by well known methods such as chromatography.

In Scheme B, step b, N-tert-butoxycarbonyl-L-serine β-lactone (20) is reacted with allyl amine to provide the amino acid of structure (21).

For example, a solution of N-tert-butoxycarbonyl-L-serine β-lactone (20) in a suitable organic solvent, such as acetonitrile ($CH_3CN$) is added to a solution of allyl amine in a suitable organic solvent, such as acetonitrile. The amino acid of structure (21) may be isolated using well known techniques such as evaporation. A hydroxamide byproduct may be recovered by concentration of the filtrate.

In Scheme B, step c, the amino acid of structure (21) is Z-protected at the secondary amine and the Boc-protecting group at the primary amine is replaced with a phthalimido group to provide the desired phthalimido acid of structure (22).

For example, a solution of amino acid of structure (21) in saturated aqueous $NaHCO_3$ and water is reacted with a solution of benzyl chloroformate in a suitable organic solvent, such as acetone. The reactants are typically stirred together at ambient temperature for a period of time ranging from about 2–10 hours. The CBz-amino acid intermediate can be recovered from the reaction zone by extractive techniques known in the art. It may be used without further purification.

A solution of the CBz-amino acid intermediate in a suitable organic solvent such as methylene chloride is then treated with trifluoroacetic acid. The reactants are typically stirred at ambient temperature for 1–4 hours and concentrated. The trifluoroacetic acid salt intermediate is recovered from the reaction zone by extractive techniques and may be used without further purification.

A solution of the trifluoroacetic acid salt intermediate in a water:ethereal solvent mixture, such as water:dioxane, and solid $Na_2CO_3$ is treated with N-carbethoxyphthalimide (NCEP). The reactants are typically stirred for 3–10 hours at a temperature ranging from about 30° C. to about 50° C. After stirring, additional $Na_2CO_3$ is added to bring the pH of the reaction mixture to approximately pH 8–10. N-carbethoxyphthalimide (NCEP) is re-added and the reaction is stirred an additional 12 to 24 hours. The phthalimido acid of structure (22) may be recovered from the reaction zone by extractive methods as are known in the art. It may be purified by known purification techniques such as flash chromatography.

In Scheme B, step d, the acid functionality of the phthalimido acid of structure (22) is converted to a trimethylsilyl ester functionality to provide the ester of structure (23).

For example, a solution of the phthalimido acid of structure (22) in a suitable organic solvent or solvent mixture, such as tetrahydrofuran and methylene chloride is treated with 2-trimethylsilylethanol; a suitable organic amine, such as pyridine, triethylamine, N-methylmorpholine, and the like; and 1-(3-dimethylaminopropyl)-3-ethylcarbodiimide hydrochloride. The reactants are typically stirred for 12–24 hours at ambient temperature. The desired ester of structure (23) may be isolated from the reaction zone by extraction and evaporation and may be purified by flash chromatography.

In Scheme B, step e, the ester of structure (23) is oxidized to afford the aldehyde of structure (24).

For example, a solution of the ester of structure (23) in a suitable organic solvent or solvent mixture, such as methylene chloride and methanol, is cooled to approximately −78° C., under an inert atmosphere, such as argon. Ozone is then passed through the solution for a sufficient time, typically until a blue color persists. Excess ozone may be purged from the solution by bubbling argon through the solution for a period of time ranging from 10–20 minutes. A suitable reducing agent such as dimethyl sulfide may then be added and the solution is allowed to warm gradually to ambient temperature for a period of from about 6–20 hours. The aldehyde of structure (24) may be obtained from the reaction zone by extraction and evaporation and may be purified by flash chromatography.

In Scheme B, step f, the aldehyde of structure (24) is coupled with the $R_3$-substituted amine salt of structure (7a) to provide the corresponding amino-ester of structure (25).

For example, a solution of the aldehyde of structure (24) and $R_3$-substituted amine salt of structure (7a) in a protic solvent, such as methanol or ethanol, is typically stirred for 10–20 minutes, treated with sodium cyanoborohydride, and then stirred for approximately 3–6 hours. The amino-ester of structure (25) is recovered from the reaction zone by extraction and evaporation and is purified by flash chromatography.

In Scheme B, step g, the amino-ester of structure (25) is cyclized in a manner analogous to the procedures described in Scheme A, step g, to give the CBz-lactam of structure (26).

In Scheme B, step h, the CBz-protected amine functionality of the Z-lactam of structure (26) is deprotected to afford the lactam of structure (27).

For example, a solution of the Z-lactam in a suitable organic solvent, such as methanol, may be treated with 10% palladium/carbon catalyst (Pd—C) and stirred under a hydrogen atmosphere for a period of from 10–20 hours. Additional catalyst may then be added, the mixture may be stirred for an additional 5–10 hours, degassed and filtered. The filtrate is then concentrated to yield the lactam of structure (27).

In Scheme B, step i, the lactam of structure (27) is reacted with an $R_2$-substituted halide of the formula $R_2$-Hal, wherein "Hal" is Cl, Br or I, to provide the $R_2$-substituted lactam of structure (28).

For example, a solution of the lactam of structure (27), in a suitable organic solvent or solvent mixture, such as acetonitrile and dimethylforamide, is treated with an appropriate $R_2$-substituted halide and solid $K_2CO_3$. After a period of time ranging from about 12–24 hours, the desired lactam of structure (28) is isolated from the reaction zone by extraction and evaporation and is purified by flash chromatography.

In Scheme B, step j, the phthalimido-protected amine functionality of the lactam of structure (28) is deprotected to provide the amine of structure (29).

For example, a solution of the lactam of structure (28) in a suitable organic solvent such as methanol, is contacted with two molar equivalents of hydrazine hydrate in a suitable organic solvent such as methanol. The reaction is typically carried out at ambient temperature. The reaction mixture is then stirred for a period of time ranging from about 60–90 hours and is then filtered. The filtrate is concentrated to afford the amine of structure (29).

In Scheme B, step k, the amine of structure (29) is coupled with the bromoacid of structure (12a) in a manner analogous to the procedures described in Scheme A, steps i1 and i2, to give the bromoamide of structure (30).

In Scheme B, step 1, the bromoamide of structure (30) is converted to the α-thioamide of structure (31).

For example, a solution of bromoamide (30) and p-methoxybenzylmercaptan in a suitable organic solvent, such as dimethylformamide, is degassed and treated at ambient temperature with cesium carbonate. After a period of time ranging from 12–24 hours, the α-thioamide of structure (31) is isolated from the reaction zone by extraction and evaporation and is purified by flash chromatography.

Alternatively, the bromoamide of structure (30) may be converted to the α-thioamide of structure (31) in a manner analogous to the procedures of Scheme A, steps j1 and j2.

In Scheme B, step m, the α-thioamide of structure (31) is cleaved in a manner analogous to the procedures of Scheme A, steps k1 and k2 to provide the compound of structure (32), which corresponds to a compound of formula (I) wherein X is N and $R_8$ is H.

In Scheme B, optional step n, the thiol functionality of the compound structure (32) is acylated in a manner analogous to the procedures of Scheme A, steps 11 and 12 to provide a compound of structure (32).

Starting materials for use in Schemes A and B are readily available to one of ordinary skill in the art. For example, certain $R_2$-substituted cyclohexanones of structure (2) are commercially available, such as 4-phenylcyclohexanone, 4-methylcyclohexanone, 4-ethylcyclohexanone, 4-t-butylcyclohexanone are available from Aldrich Chemical Co., Inc., Milwaukee, Wis. 53233.

The $R_3$-substituted amine salt of structure (7a) can be prepared by utilizing techniques and procedures well known and appreciated by one of ordinary skill in the art. A general synthetic scheme is set forth in Scheme C wherein all the substituents are as previously defined unless otherwise indicated.

55

SCHEME C

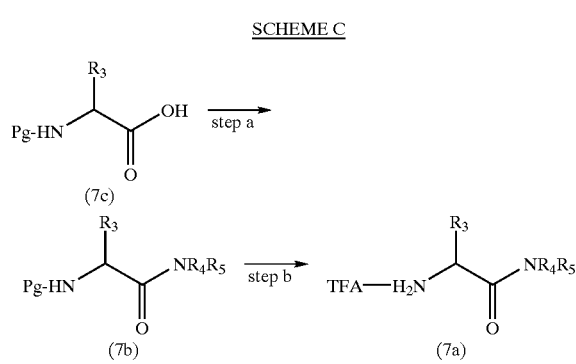

In step a, the protected amino acid of structure (7c) is amidated to provide the amino amide of structure (7b).

For example, a solution of the protected amino acid of structure (7c) in a suitable organic solvent such as tetrahydrofuran is cooled from about −25° C. to about 40° C. and treated sequentially with a slight molar excess of tertiary amine, such as N-methylmorpholine, and a slight molar excess of isobutylchloroformate. After a period of time ranging from about 10 to 20 minutes, the reaction mixture is treated with a molar excess of an amine of the formula $H_2NR_4R_5$, wherein $R_4$ and $R_5$ are as defined above, stirred for about 14 hours and concentrated. The residue is dissolved in a suitable organic solvent, such as methylene chloride, washed with an appropriate acid, such as hydrochloric acid and sodium carbonate ($NaHCO_3$). The organic layer is dried with a suitable drying agent, such as sodium sulfate and concentrated to provide crude amino amide of structure (7b).

In Scheme C, step b, the amino amide of structure (7b) is deprotected to provide the $R_3$-substituted amine salt of structure (7a).

For example, a solution of crude amino amide of structure (7b) in a suitable organic solvent, such as methylene chloride and trifluoroacetic acid is stirred at ambient temperature from about 2 to about 4 hours and concentrated. Residual trifluoroacetic acid may be removed by coevaporation with a suitable solvent mixture, such as carbon tetrachloride and toluene using a rotary evaporator. The $R_3$-substituted amine salt of structure (7a) is then isolated and purified by techniques well known and appreciated by one of ordinary skill in the art.

Starting materials for use in Scheme C are readily available to one of ordinary skill in the art. For example, N-protected amino acids of structure (7c) are commercially available or are easily made by one of ordinary skill in the art. Furthermore, amines of the formula $H_2NR_4R_5$, wherein $R_4$ and $R_5$ are defined as above, are commercially available or are easily made by one of ordinary skill in the art. Examples of amines of formula $H_2NR_4R_5$, which are commercially available from Aldrich Chemical Co., Inc. include methylamine, ethylamine, propylamine, isopropylamine, butylamine, R-(−)-sec-butylamine, (±)-sec-butylamine, S-(+)-sec-butylamine, tert-butylamine, hexylamine, morpholine, piperidine and pyrrolidine.

The bromoacids of structure (12a) are commercially available or can be prepared utilizing materials, techniques and procedures well known and appreciated by one of ordinary skill in the art. Examples of bromoacids of structure (12a) which are commercially available include 2-bromopropionic acid, 2-bromobutyric acid, 2-bromovaleric acid, 2-bromohexanoic acid, 6-(benzoylamino)-2-bromohexanoic acid,

56

α-bromoheptanoic acid, 2-bromooctanoic acid, 2-bromo-3-methylbutyric acid, α-bromoisocaproic acid, α-bromo-β-(5-imidazoyl)proionic acid, (R)-(+)-2-bromopropionic acid, (S)-(−)-2-bromopropionic acid.

The bromoacids of structure (12a) wherein $R_1$ is a W—$(CH_2)_m$— group are synthesized according to Scheme D. The bromoacid of structure (35) corresponds to the bromoacid of structure (12a) when $R_1$ is a W—$(CH_2)_n$— group.

SCHEME D

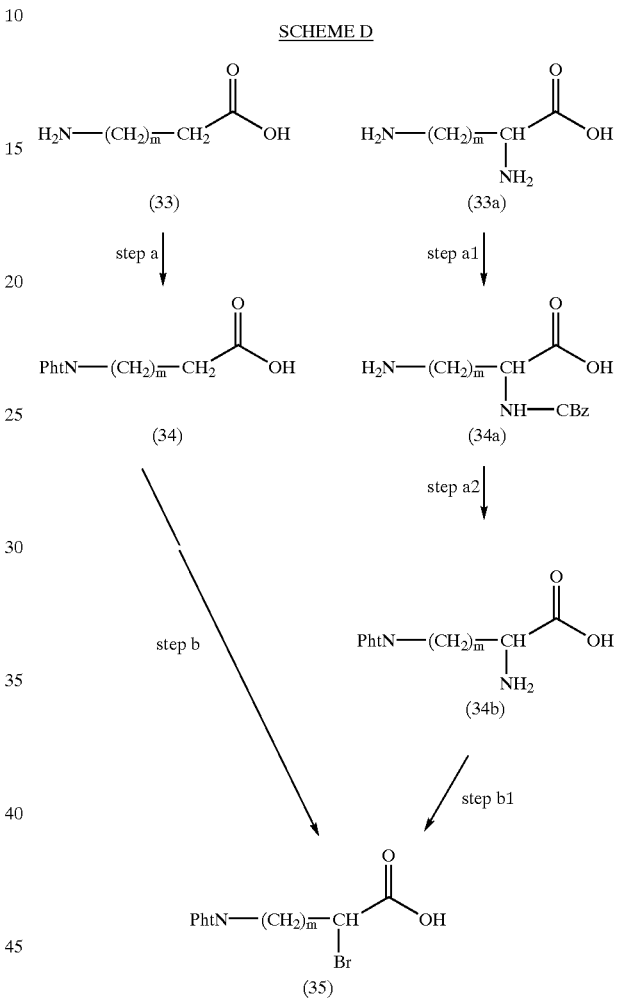

In Scheme D, step a, the amino carboxylic acid of structure (33) in a suitable polar solvent, such as water or a water:ethereal solvent mixture, is treated with $Na_2CO_3$ and N-carbethoxy phthalimide (NCEP). The reaction mixture is typically stirred at ambient temperature for 1–5 hours and extracted by extractive methods well known in the art. The to aqueous layer is then cooled and acidified to about pH 1 using an acid, such as concentrated hydrochloric acid. The precipitate is then collected by filtration, washed with water and then dried to give the phthalimido carboxylic acid of structure (34).

In Scheme D, step b, the phthalimido carboxylic acid of structure (34) is brominated to give the 2-bromo-phthalimido carboxylic acid of structure (35). For example, a mixture of the phthalimido carboxylic acid of structure (34) and dry red phosphorous is treated dropwise with bromine at temperature ranging from about −20° to about 10° C. The reaction mixture is then warmed to room temperature and then heated to about 80° C. for about 2–5 hours. The reaction mixture is then cooled to room temperature, poured into water containing NaHSO₃, and neutralized using solid NaHCO₃. The aqueous layer is washed with an ethereal solvent, such as diethyl ether, and acidified with a suitable acid, such as concentrated hydrochloric acid. The precipitate is collected by filtration and dried to yield the bromoacid of structure (35).

Alternatively, the bromoacid of structure (35) can be prepared following the procedure described in Scheme D, steps a1, a2 and b1, as described analogously by Baldwin, J. E. et al., *Tetrahedron* 44, 2633–2636 (1988) and Bezas, B. and Zervas, L., *J. Am. Chem. Soc.* 83, 719–722 (1961).

For example, in Scheme D, step a1, selective N-α-protection of a suitable α-amino acid, such as L-lysine, is accomplished by masking the ε-amino group by formation of a benzylidene imine. The benzylidene imine is formed by dissolving L-lysine monohydrochloride in lithium hydroxide and cooling the solution to a temperature ranging from about 0° to 10° C. Freshly distilled benzaldehyde is then added and the solution is shaken. N-ε-benzylidene-L-lysine is recovered by filtration and evaporation.

The α-amino group of the N-ε-benzylidene-L-lysine then undergoes urethane protection, followed by hydrolytic cleavage of the imine in situ to give N-α-benzyloxycarbonyl-L-lysine. For example, N-ε-benzylidene-L-lysine is added to a mixture of sodium hydroxide and ethanol, cooled to a temperature of from about −5° to about −25° C. Then, precooled solutions of benzyloxycarbonyl chloride in an alkaline solvent, such as sodium hydroxide and ethanol, are added to the reaction mixture. The temperature is maintained at a temperature ranging from about −10° to about −25° C. during the course of addition, and then allowed to rise slightly (approx. −5° C.) with stirring. The reaction mixture is then acidified using a suitable acid, such as precooled hydrochloric acid, and N-α-benzyloxycarbonyl-L-lysine, which corresponds to structure (34a) where m is 4, is recovered by filtration and recrystallization.

In Scheme D, step a2, N-α-benzyloxycarbonyl-L-lysine or other compounds of structure (34a) are reacted with N-carboethoxyphthalimide in aqueous sodium carbonate solution to yield optically pure phthaloyl derivatives of the compounds of structure (34a).

The phthaloyl derivatives of the compounds of structure (34a) are then reduced concurrently with carbobenzoxy hydrogenolysis to give the N-ε-phthaloyl amino acids of structure (34b). For example, the individual phthaloyl derivative of structure (34a) is contacted with a catalytic amount of a hydrogenation catalyst, such as 10% palladium/carbon. The reactants are typically contacted in a suitable solvent mixture such as tetrahydrofuran/water. The reactants are typically shaken under a hydrogen atmosphere of 35–45 psi at room temperature for a period of time ranging from 5–24 hours. The individual N-ε-phthaloyl amino acid of structure (34b) is recovered from the reaction zone by evaporation of the solvent.

In Scheme D, step b1, the individual N-ε-phthaloyl amino acid of structure (34b) is deaminobrominated to yield the bromoacid of structure (35). This reaction can be performed utilizing a reaction of the type described in Compagnone, R. S. and Rapoport, H., *J. Org. Chem.*, 51, 1713–1719 (1986); U.S. Pat. No. 5,322,942, issued Jun. 21, 1994; Overberger, C. G. and Cho, I., *J. Org. Chem.*, 33, 3321–3322 (1968); or Pfister, K. et al., *J. Am. Chem. Soc.*, 71, 1096–1100 (1949).

For example, a mixture of N-ε-phthaloyl amino acid of structure (34b) and a suitable hydrogen bromide, such as hydrogen bromide or potassium bromide, in acidic solution, such as sulfuric acid, is treated with sodium nitrite. If avoidance of racemization caused by excess bromide ion is desired, the reaction temperature can be kept between −5° C. and 0° C. during addition and stirring. After the reaction mixture is stirred for a period of time ranging from 1.5 to 5 hours, the bromoacid of structure (35) may be recovered by extraction and evaporation.

The bromoacids of structure (12a) wherein $R_1$ is $C_1$-$C_6$ alkyl or a Q'—Z'—(CH$_2$)$_m$— group, wherein m is as defined above and Q' is hydrogen or a Y'—(CH$_2$)$_n$— group, wherein Y' is —C(O)OR$_6$; Z' is a bond, oxy or amino, are synthesized according to Scheme E. The bromoacid of structure (37) corresponds to the bromoacid of structure (12a) when $R_1$ is $C_1$-$C_6$ alkyl, or a Q'—Z'—(CH$_2$)$_m$— group.

SCHEME E

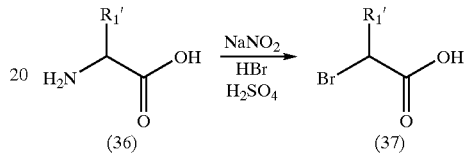

Scheme E provides a general synthetic procedure for preparing the bromoacids of structure (12a) when $R_1$ is $C_1$-$C_6$ alkyl or a Q'—Z'—(CH$_2$)$_m$— group, signified as structure (37). The substituent $R_1'$ is defined as $C_1$-$C_6$ alkyl, or a Q'—Z'—(CH$_2$)$_m$— group.

In Scheme E, an appropriate amino acid of structure (36) is deaminobrominated to yield the $R_1'$-substituted bromoacid of structure (37) as described previously in Scheme D, step b1.

The amino acids of structure (36), and N-protected forms thereof, are commercially available or may be readily prepared by techniques and procedures well known and appreciated by one of ordinary skill in the art. For example, L-alanine, D-alanine, L-valine, D-valine, D-norvaline, L-leucine, D-leucine, D-isoleucine, D-tert-leucine, glycine, L-glutamic acid, D-glutamic acid, L-glutamine, D-glutamine, L-lysine, D-lysine, L-ornithine, D-ornithine, (D)-(−)-2-aminobutyric acid, D-threonine, D-homoserine, D-allothreonine, D-serine, D-2-aminoadipic acid, D-aspartic acid, D-glutamic acid, D-lysine hydrate, 2,3-diaminopropionic acid monohydrobromide, D-ornithine hydrochloride, D,L-2,4-diaminobutyric acid dihydrochloride, L-meta-tyrosine, D-4-hydroxyphenylglycine, D-tyrosine, D-phenylalanine, D,L-2-fluorophenylalanine, beta-methyl-DL-phenylalanine hydrochloride, D,L-3-fluorophenylalanine, 4-bromo-DL-phenylalanine, D-2-phenylglycine, D,L-4-fluorophenylalanine, 4-iodo-D-phenylalanine, D-homophenylalanine, D,L-2-fluorophenylglycine, D,L-4-chlorophenylalanine, and the like, are all commercially available from Sigma Chemical Co., St. Louis, Mo. or Aldrich Chemical Co., Inc.

The cis α-thioamide of structure (15), the trans α-thioamide of structure (16), and the α-thioamide of structure (31) where $R_1$ is a Q'$^2$—Z'$^2$—(CH$_2$)$_m$— group wherein Q'$^2$ is a Y'$^2$ (CH$_2$)$_n$— group, where Y'$^2$ is —N(R$_6$)$_2$, can be synthesized according to techniques well known and appreciated by one of ordinary skill in the art. A general synthetic scheme for preparing these compounds is set forth in Scheme F wherein all substituents, unless otherwise indicated, are previously defined. The α-thioamide of structure (38) generically represents the cis α-thioamide of structure (15), the trans α-thioamide of structure (16), and the α-thioamide of structure (31) when $R_1$ is a $Q'_2$—$Z'^2$—$(H_2)_m$— group wherein $Q'^2$ is a $Y'^2$—$(CH_2)_n$— group, where $Y'^2$ is —$N(R_6)_2$.

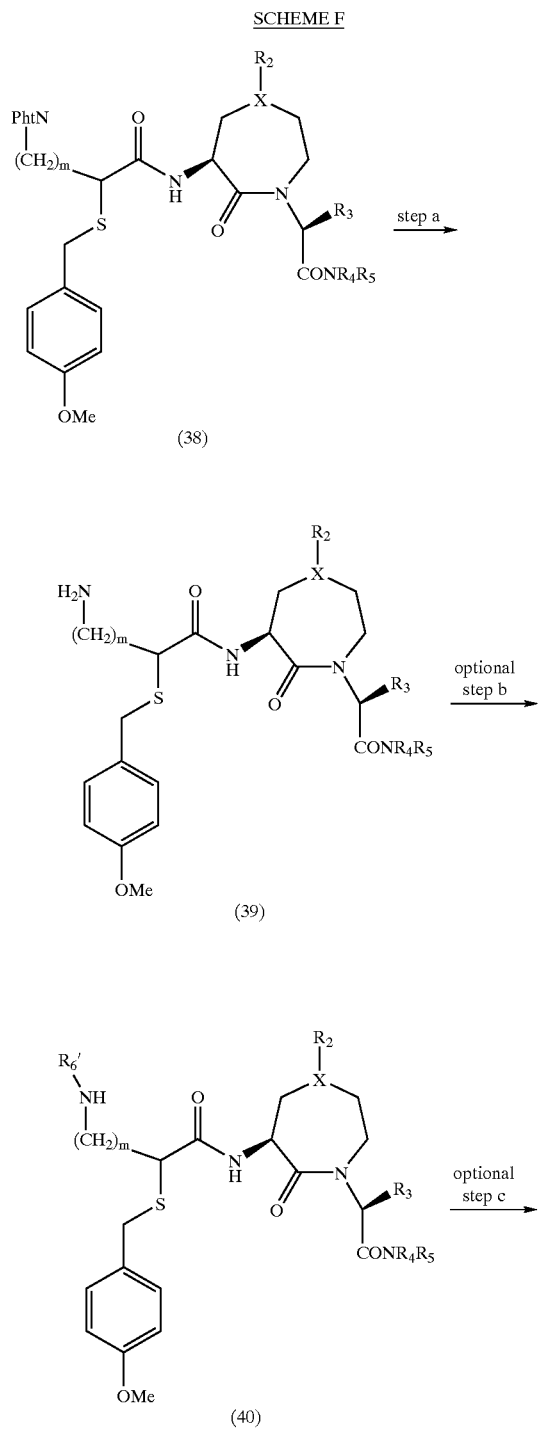

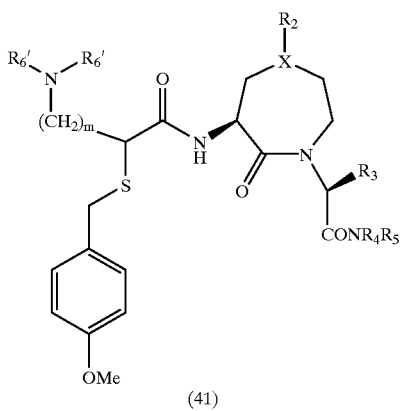

Scheme F provides a general synthetic procedure for preparing compounds of structures (15), (16) and (31) wherein $R_1$ is a $Q'^2$—$Z'^2$—$(CH_2)_m$— group wherein $Q'^2$ is a $Y'^2$—$(CH_2)_n$— group, where $Y'^2$ is —$N(R_6)_2$. All of the substituents are as defined above except $R_6'$ which is defined as $C_1$–$C_6$ alkyl.

In Scheme F, step a, the phthalimido group of the appropriate individual α-thioamide compounds of structure (38) is contacted with a molar excess of hydrazine monohydrate. The reactants are typically contacted in a protic organic solvent, such as methanol. The reactants are typically stirred together at room temperature for a period of time ranging from 5–24 hours. The corresponding free amine compounds of structure (39) are recovered from the reaction zone by evaporation of the solvent, redissolving in $CHCl_3$, filtration to remove phthalhydrazide and removal of the $CHCl_3$ in vacuo.

In Scheme F, optional step b, the individual free amines of structure (39) are converted to the $R_6'$-substituted amines of structure (40) by reductive alkylation.

For example, the a mixture of the free amine of structure (39) in a protic organic solvent, such as methanol, is contacted with $R_6'CHO$, sodium cyanoborohydride and 1 drop of 1% bromocresol green in methanol. The pH of the reaction is maintained with 1N hydrochloric acid in methanol. The $R_6'$-substituted amines of structure (40) are recovered from the reaction zone by extraction and evaporation of the solvent.

In Scheme F, optional step c, the $R_6'$-substituted amines of structure (40) is converted to the di-$R_6'$-substituted amines of structure (41) as described above in Scheme E, optional step b.

The cis α-thioamide of structure (15), the trans α-thioamide of structure (16), and the α-thioamide of structure (31) where $R_1$ is a $Q'^3$—$Z'^3$—$(CH_2)_m$— group, wherein $Q'^3$ is a $Y'^3$—$(CH_2)_n$— group, $Z'^3$ is $CONR_6$, and $Y'^3$ is H, $C_6$–$C_{10}$ aryl, $C_3$–$C_9$ heteroaryl, morpholino, piperidino, pyrrolidino or isoindolyl can be synthesized according to techniques well known and appreciated by one of ordinary skill in the art. A general synthetic scheme for preparing these compounds, signified as the compounds of structure (43), is set forth in Scheme G wherein all substituents, unless otherwise indicated, are previously defined.

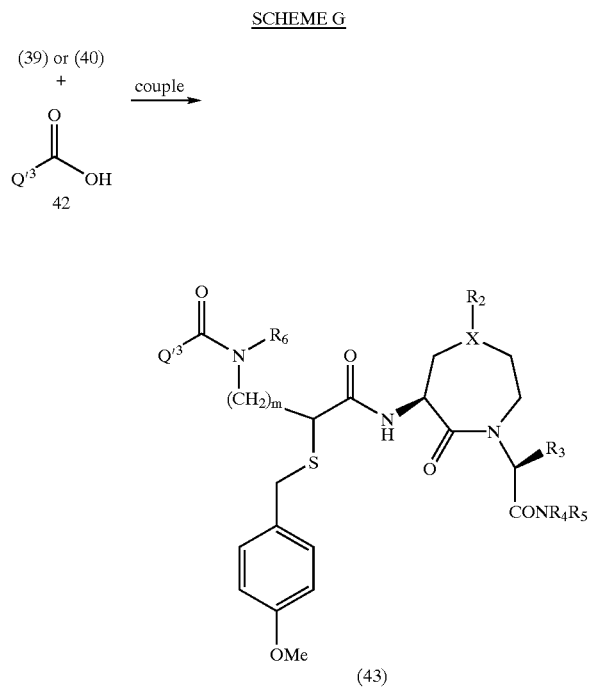

Scheme G provides a general synthetic procedure for preparing compounds of structures (15), (16) and (31) wherein $R_1$ is a $Q'^3$-$Z^3$—$(CH_2)_m$— group wherein $Q'^3$ is a $Y'^3$ $(CH_2)_n$— group, $Z'^3$ is $CONR_6$, and $Y'^3$ is H, $C_6$–$C_{10}$ aryl, $C_3$–$C_9$ heteroaryl, morpholino, piperidino, pyrrolidino or isoindolyl. All of the other substituents are as previously defined.

In Scheme G, the compounds of structure (43) are prepared by coupling the free amine of structure (39) or the $R_6'$-substituted amines of structure (40) with the acid of structure (42). Specifically, an acid of structure (42) is contacted with 1.2 to 1.7 equivalents of a suitable base, such as N-methylmorpholine, in a suitable solvent, such as tetrahydrofuran. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride, an activated intermediate. While maintaining the temperature at between −50° C. and 0° C., an appropriate free amine of structure (39) or an appropriate $R_6'$-substituted amines of structure (40) is added. The reaction may, after the addition of amine of structures (39) or (40) is complete, be warmed to room temperature. The reaction requires from 2 to 48 hours. The product (43) can be isolated and purified by techniques well known in the art, such as extraction, evaporation, chromatography, and recrystallization.

Alternatively, for example, an acid of structure (42) is contacted with thionyl chloride or oxalyl chloride to provide an acid chloride intermediate. The reaction is carried out using thionyl chloride or oxalyl chloride as a solvent or the reaction can be carried out in a suitable solvent, such as toluene, benzene, dichloromethane, carbon tetrachloride, or chloroform. The reaction may be carried out in the presence of a suitable catalyst, such as dimethylformamide or pyridine. The reaction is carried out at temperatures of from −40° C. to the refluxing temperature of the solvent. The reaction generally requires from 30 minutes to 24 hours. The acid chloride intermediate can isolated and purified by techniques well known in the art, such as evaporation, extraction, chromatography, and recrystallization.

The acid chloride intermediate is then contacted with an appropriate amine of structures (39) or (40). The reaction is carried out in a suitable solvent, such as toluene, tetrahydrofuran, dimethylformamide, dichloromethane, pyridine, or chloroform. The reaction is carried out in the presence of a slight molar excess of a suitable base, such as triethyl amine, sodium carbonate, potassium bicarbonate, pyridine or diisopropylethyl amine. The reaction is carried out at a temperature of from −70° C. to the refluxing temperature of the solvent. The reaction generally requires from 30 minutes to 24 hours. The product of structure (43) can be isolated and purified by techniques well known in the art, such as extraction, evaporation, chromatography, and recrystallization.

Alternatively, for example, an acid of structure (42) is contacted with a slight molar excess of an appropriate amine of structures (39) or (40) and 1-hydroxybenzotriazole hydrate in the presence of a slight molar excess of a coupling agent, such as dicyclohexylcarbodiimide (DCC) or 1-(3-dimethyaminopropyl)-3-ethylcarbodiimide (EDC). The reaction is carried out in the presence of a suitable base, such as diisopropylethyl amine. The reaction is carried out in a suitable solvent, such as dichloromethane or chloroform. The product can be isolated and purified by techniques well known in the art, such as extraction, evaporation, chromatography, and recrystallization.

The compounds of structure (42), and activated intermediates thereof, are commercially available or may be readily prepared by techniques and procedures well known and appreciated by one of ordinary skill in the art. For example, benzoic acid, 1-naphthoic acid, 2-naphthoic acid, quinaldic acid, 4-pyridazine-arboxylic acid, 4-pyrazolecarboxylic acid, 2-furoic acid, 3-furoic acid, 2-pyrazinecarboxylic acid, 2-thiophenecarboxylic acid, 4-morpholinecarbonyl chloride, Boc-isonipecotic acid, isonicotinic acid, and picolinic acid are commercially available from Aldrich Chemical Co., Inc and Baychem, Inc.

The cis α-thioamide of structure (15), the trans α-thioamide of structure (16), and the α-thioamide of structure (31) where $R_1$ is a $Q'^3$—$Z'^4$—$(CH_2)_n$— group, wherein $Q'^3$ is as defined in Scheme G, m is defined previously and $Z'^4$ is NHC(O)$NR_6$, can be synthesized according to techniques well known and appreciated by one of ordinary skill in the art. A general synthetic scheme for preparing these compounds, signified as the compounds of structure (45), is set forth in Scheme H wherein all substituents, unless otherwise indicated, are previously defined.

SCHEME H

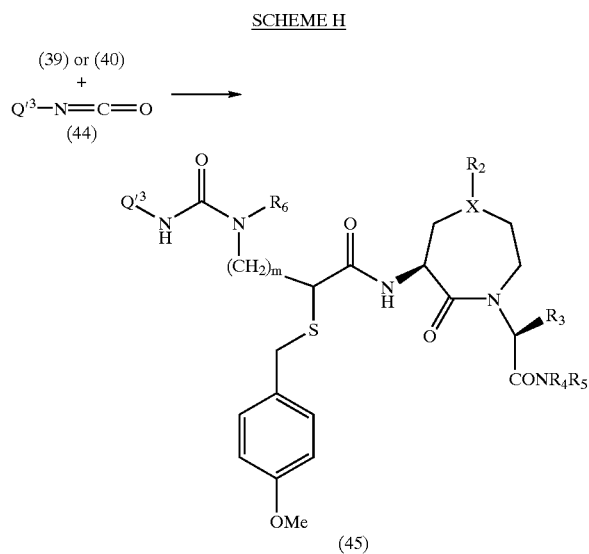

Scheme H provides a general synthetic procedure for preparing compounds of structures (15), (16) and (31) wherein $R_1$ is a $Q'^3$—$Z'^4$—$(CH_2)_m$— group, wherein $Q'^3$ is as defined in Scheme G, m is defined previously and $Z'^4$ is $NHC(O)NR_6$. All of the other substituents are as defined above.

In Scheme H, the compounds of structure (45) are prepared by reacting a free amine of structure (39) or a $R_6'$-substituted amine of structure (40) with the isocyanate of structure (44). For example, an equivalent of, or a slight molar excess of, an appropriate isocyanate of structure (44) is added to a solution of an appropriate free amine of structure (39) or an appropriate $R_6'$-substituted amine of structure (40) in a suitable dry aromatic solvent, such as anhydrous benzene or anhydrous toluene. The mixture is then refluxed for a period of time ranging from 2–24 hours. The appropriate compound of structure (45) can be isolated and purified by techniques well known in the art, such as extraction, evaporation, chromatography, and recrystallization.

The compounds of structure (44), and activated intermediates thereof, are commercially available or may be readily prepared by techniques and procedures well known and appreciated by one of ordinary skill in the art. For example, phenyl isocyanate and 1-naphthyl isocyanate are available from Aldrich Chemical Co., Inc. Other compounds of structure (44) which are known in the art include 4-methyphenyl isocyanate, 4-methoxyphenyl isocyanate, 2-naphthyl isocyanate, 4-aminophenyl isocyanate, 4-fluorophenyl isocyanate, 3-chlorophenyl isocyanate, 4-chlorophenyl isocyanate, 3,4-dichlorophenyl isocyanate, 2,6-dimethylphenyl isocyanate, 2-methoxy-1-naphthyl isocyanate, 2,4,6-trimethylphenyl isocyanate and 4-nitrophenyl isocyanate.

The cis α-thioamide of structure (15), the trans α-thioamide of structure (16), and the α-thioamide of structure (31) where $R_1$ is a $Q'^3$—$Z'^5$—$(CH_2)_m$— group, wherein $Q'^3$ is as defined in Scheme G, m is defined previously and $Z'^5$ is $OC(O)NR_6$, can be synthesized according to techniques well known and appreciated by one of ordinary skill in the art. A general synthetic scheme for preparing these compounds, signified as the compounds of structure (48), is set forth in Scheme I wherein all substituents, unless otherwise indicated, are previously defined.

SCHEME I

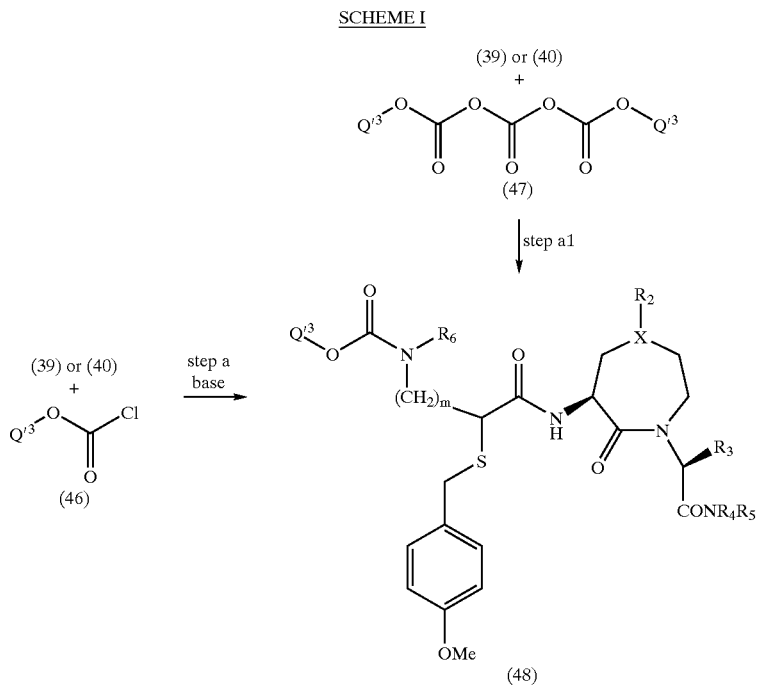

Scheme I provides a general synthetic procedure for preparing compounds of structures (15), (16) and (31) wherein $R_1$ is a $Q'^3$—$Z'^5$—$(CH_2)_m$— group, wherein $Q'^3$ is as defined in Scheme G, m is defined previously and $Z'^5$ is $OC(O)NR_6$. All of the other substituents are as defined above.

In Scheme I, step a, an appropriate free amine of structure (39) or an appropriate $R_6'$-substituted amine of structure (40) is coupled to the chloroformate of structure (46) in the presence of a suitable solvent, such as toluene, tetrahydrofuran, dimethylformamide, dichloromethane, pyridine, or chloroform. The reaction is carried out in the presence of a slight molar excess of a suitable base, such as triethyl amine, sodium carbonate, potassium bicarbonate, pyridine or diisopropylethyl amine. The reaction is carried out at a temperature of from −70° C. to the refluxing temperature of the solvent. The reaction generally requires from 30 minutes to 24 hours. The product of structure (48) can be isolated and purified by techniques well known in the art, such as extraction, evaporation, chromatography, and recrystallization.

The chloroformates of structure (46) are commercially available or may be readily prepared by techniques and procedures well known and appreciated by one of ordinary skill in the art. For example, phenyl chloroformate, benzyl chloroformate, 4-chlorophenyl chloroformate, 4-nitrophenyl chloroformate, 4-methylphenyl chloroformate, 4bromophenyl chloroformate, 4-fluorophenyl chloroformate, 4-methoxyphenyl chloroformate and chloroformic acid 2-naphthyl ester are available from Aldrich Chemical Co., Inc., or are otherwise known in the art.

Alternatively, in Scheme I, step a1, an appropriate free amine of structure (39) or an appropriate $R_6'$-substituted amine of structure (40) is reacted with the anhydride of structure (47) according to the anhydride coupling procedure described previously in Scheme G.

The anhydrides of structure (47) may be readily prepared by techniques and procedures well known and appreciated by one of ordinary skill in the art. See for example, Pope, B. M. et al., *Org. Synth.*, VI, 418 (1988); Dean, C. S. et al., *Chem. Comm.*, 728 (1969); Tarbell, D. S. et al., *Proc. Natl. Acad. Sci.* (USA) 69, 730 (1972) or Dean, C. S. et al., *J. Org. Chem.* 35, 3393 (1970).

The cis α-thioamide of structure (15), the trans α-thioamide of structure (16), and the α-thioamide of structure (31) where $R_1$ is a $Q'^3$—$Z'^5$—$(CH_2)_m$— group, wherein $Q'^3$ is as defined in Scheme G, m is defined previously and $Z'^6$ is $SO_2NR_6$, can be synthesized according to techniques well known and appreciated by one of ordinary skill in the art. A general synthetic scheme for preparing these compounds, signified as the compounds of structure (51), is set forth in Scheme J wherein all substituents, unless otherwise indicated, are previously defined.

SCHEME J

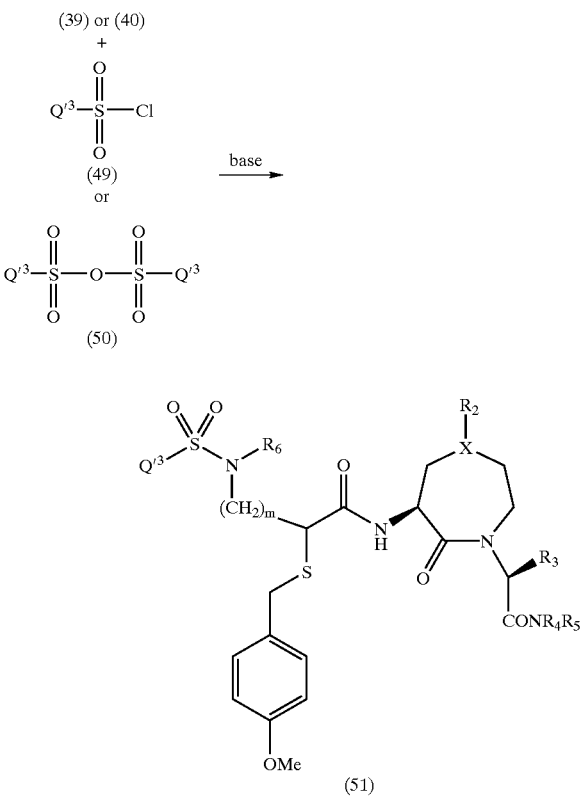

Scheme J provides a general synthetic procedure for preparing compounds of structures (15), (16) and (31) wherein $R_1$ is a $Q'^3$—$Z'^6$—$(CH_2)_m$— group, wherein $Q'^3$ is as defined in Scheme G, m is defined previously and $Z'^r$ is $SO_2NR_6$. All of the other substituents are as defined above.

In Scheme J, an appropriate free amine of structure (39) or an appropriate $R_6'$-substituted amine of structure (40) is reacted with the with the chloride of structure (49) or the anhydride of structure (50) according to the anhydride coupling procedure described previously in Scheme G.

The chlorides of structure (49) are commercially available or may be readily prepared by techniques and procedures well known and appreciated by one of ordinary skill in the art. For example, benzenesulfonyl chloride, 1-napthalenesulfonyl chloride, 2-napthalenesulfonyl chloride, dansyl chloride, 8-quinolinesulfonyl chloride, 2-dibenzofuransulfonyl chloride, 1,2-napthoquinone-2-diazide-4-sulfonyl chloride, N-morpholinylsulfonyl chloride, N-piperidinylsulfonyl chloride, 2,4,5-trichlorobenzenesulfonyl chloride, 2,5-dichlorobenzenesulfonyl chloride, 2-nitrobenzenesulfonyl chloride, 2,4-dinitrobenzenesulfonyl chloride, 3,5-dichloro-2-hydroxybenzenesulfonyl chloride, 2,4,6-triisopropylbenzenesulfonyl chloride, 2-mesitylenesulfonyl chloride, 3-nitrobenzenesulfonyl chloride, 4-bromobenzenesulfonyl chloride, 4-fluorobenzenesulfonyl chloride, 4-chlorobenzenesulfonyl chloride, 4-chloro-3- nitrobenzenesulfonyl chloride, 4-nitrobenzenesulfonyl chloride, 4-methoxybenzenesulfonyl chloride, 4-t-butylbenzenesulfonyl chloride, p-toluenesulfonyl chloride, 2,3,4-trichlorobenzenesulfonyl chloride, 2,5-dimethoxybenzenesulfonyl chloride, 4-ethylbenzenesulfonyl chloride, 3,4-dimethoxybenzenesulfonyl chloride, 2,6-dichlorobenzenesulfonyl chloride, 3-bromobenzenesulfonyl chloride, 4-methoxy-2-nitrobenzenesulfonyl chloride and 4-n-butylbenzenesulfonyl chloride are available from Aldrich Chemical Co., Inc., other chemical suppliers, such as Lancaster, Salor, or Maybridge, or are otherwise known in the art.

The anhydrides of structure (50) are commercially available or may be readily prepared by techniques and procedures well known and appreciated by one of ordinary skill in the art. For example, benzenesulfonic anhydride, 4-toluenesulfonic anhydride, 2-mesitylenesulfonic anhydride and 4-nitrobenzenesulfonic anhydride are available from Aldrich Chemical Co., Inc., or are otherwise known in the art.

The cis α-thioamide of structure (15), the trans α-thioamide of structure (16), and the α-thioamide of structure (31) where $R_1$ is a $Q'_3$—$Z'^7$—$(CH_2)_m$— group, wherein $Q'^3$ is as defined in Scheme G, m is defined previously and $Z'^7$ is $NR_6C(O)$, can be synthesized according to techniques well known and appreciated by one of ordinary skill in the art. A general synthetic scheme for preparing these compounds, signified as the compounds of structure (54), is set forth in Scheme K wherein all substituents, unless otherwise indicated, are previously defined.

SCHEME K

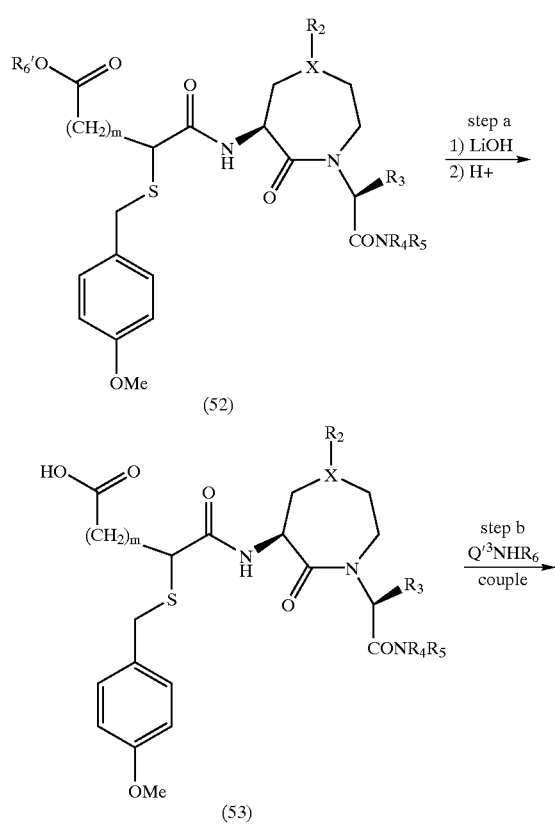

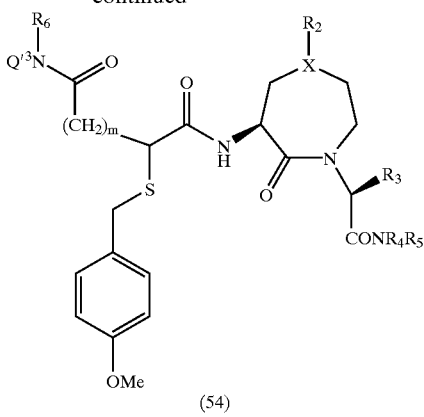

(54)

Scheme K provides a general synthetic procedure for preparing compounds of structures (15), (16) and (31) wherein $R_1$ is a $Q'_3$—$Z'^7$ $(CH_2)_m$— group, wherein $Q'^3$ is as defined in Scheme G, m is defined previously and $Z'^7$ is $NR_6C(O)$. All of the other substituents are as defined above.

In Scheme K, step a, an appropriate ester of structure (52) is deprotected under conditions well known in the art to provide the acid of structure (53). For example, when $R_6'$ is methyl or ethyl, the ester of structure (52) is dissolved in a suitable organic solvent, such as ethanol and treated with approximately an equal volume of water. To this solution, with stirring is added 1 to 2 equivalents of lithium hydroxide and the reaction is allowed to stir for 1 to 6 hours. The resulting acid is then isolated and purified by techniques well known in the art. For example, the organic solvent is removed under vacuum and the remaining aqueous solution is acidified with dilute hydrochloric acid. The aqueous phase is then extracted with a suitable organic solvent, such as ethyl acetate, and the combined organic extracts are dried over anhydrous magnesium sulfate, filtered and concentrated under vacuum. The residue can then be purified by flash chromatography on silica gel with a suitable eluent, such as methanol/chloroform to provide the acid of structure (53).

In Scheme K, step b, the acid of structure (53) is coupled with the amine of structure (53a) under conditions well known in the art to provide the retroamide of structure (54). For example, the acid of structure (53) is dissolved in a suitable organic solvent, such as methylene chloride, under an inert atmosphere, such as nitrogen. The solution is then treated with one to four equivalents of a suitable amine, such as N-methylmorpholine, cooled to about −20° C. and one equivalent of isobutylchloroformate is added. The reaction is allowed to stir for about 10 to 30 minutes and 1 to 4 equivalents of the amine of structure (53a) is added to the reaction. The reaction is stirred for 30 minutes to 2 hours at about −20° C. and then it is allowed to warm to room temperature and stir for 1 to 3 hours. The retroamide (54) is then isolated and purified by techniques well known in the art, such as extractive techniques and flash chromatography. For example, the reaction is diluted with a suitable organic solvent such as methylene chloride, rinsed with water, dried over anhydrous magnesium sulfate, filtered and concentrated under vacuum. The residue is purified by flash chromatography on silica gel with a suitable eluent, such as ethyl acetate/hexane to provide the retroamide (54).

Alternatively, the amine of structure (53a) is dissolved in a suitable anhydrous organic solvent, such as methylene chloride under an inert atmosphere, such as nitrogen. To this solution is added an equivalent of N-hydroxybenztriazole hydrate, an equivalent of 1-(3-dimethylaminopropyl)-3-ethylcarbodiimide hydrochloride and an equivalent of the acid of structure (53), dissolved in a suitable anhydrous organic solvent, such as methylene chloride. The reaction is then allowed to stir for about 1 to 15 hours. The retroamide of structure (54) is then isolated and purified by techniques well known in the art, such as extractive techniques and flash chromatography. For example, the reaction is diluted with a suitable organic solvent, such as ethyl acetate, rinsed with water, dried over anhydrous magnesium sulfate, filtered and concentrated under vacuum. The residue is purified by flash chromatography on silica gel with a suitable eluent, such as ethyl acetate/hexane to provide the retroamide (54).

The cis α-thioamide of structure (15), the trans α-thioamide of structure (16), and the α-thioamide of structure (31) where $R_1$ is a $Q'^3$—$Z'^8$—$(CH_2)_m$— group, wherein $Q'^3$ is as defined in Scheme G, m is defined previously and $Z'^8$ is HNC(O)O, can be synthesized according to techniques well known and appreciated by one of ordinary skill in the art. A general synthetic scheme for preparing these compounds, signified as the compounds of structure (56), is set forth in Scheme L wherein all substituents, unless otherwise indicated, are previously defined.

SCHEME L

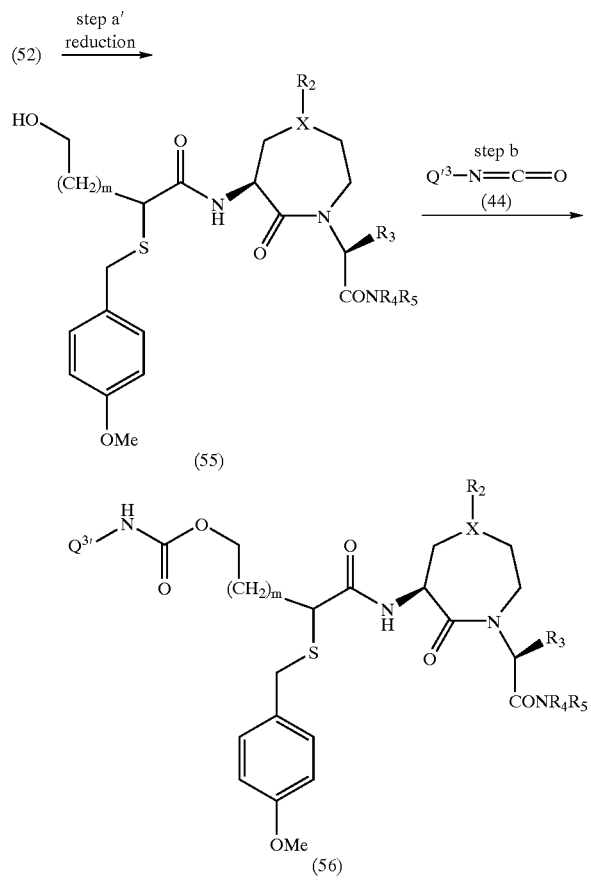

structure (52) is dissolved in a suitable solvent, such as hexane, dichloromethane, tetrahydrofuran or toluene, with tetrahydrofuran being preferred, and contacted with a suitable reducing agent, such as lithium borohydride, sodium borohydride, lithium aluminum hydride, diisobutylaluminum hydride, 9-borabicyclo[3.3.1]nonane, preferably lithium borohydride. The reaction is carried out by either adding a solution of an appropriate ester (52) to a solution of an appropriate reducing agent or by adding a solution of an appropriate reducing agent to a solution of an appropriate ester of structure (52). The addition is carried out at a temperature of from about −30° C. to about 10° C. The reaction is carried out at a temperature of from about 0° C. to about 30° C. The reaction generally requires from 2 to 5 hours. The product can be isolated by quenching and extraction. The quench is carried out at a temperature of from about −15° C. to about 0° C. The alcohol of structure (55) can be isolated by methods well known and appreciated in the art, such as extraction and evaporation. The alcohol of structure (55) can be purified as is well known in the art by chromatography and distillation.

In Scheme L, step b, the alcohol of structure (55) is reacted with the isocyanate of structure (44) according to the procedures set forth in Scheme H above to afford the appropriate compound of structure (56).

Alternatively, the cis α-thioamide of structure (15), the trans α-thioamide of structure (16), and the α-thioamide of structure (31) can be synthesized according to techniques well known and appreciated by one of ordinary skill in the art. An alternate general synthetic scheme for preparing these compounds is set forth in Scheme M wherein all substituents, unless otherwise indicated, are previously defined.

SCHEME M

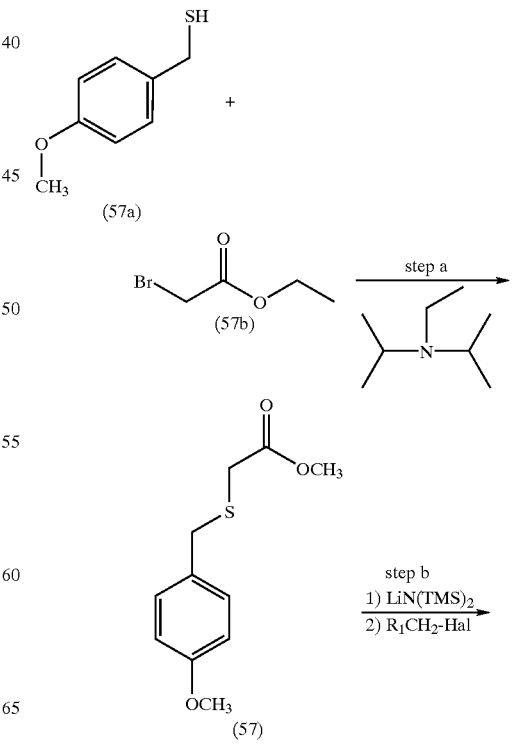

Scheme L provides a general synthetic procedure for preparing compounds of structures (15), (16) and (31) wherein $R_1$ is a $Q'^3$—$Z'^8$—$(CH_2)_m$— group, wherein $Q'^3$ is as defined in Scheme G, m is defined previously and $Z'^8$ is HNC(O)O. All of the other substituents are as defined above.

In Scheme L, step a, an appropriate ester of structure (52) is reduced under conditions well known in the art to provide the alcohol of structure (55). For example, the ester of

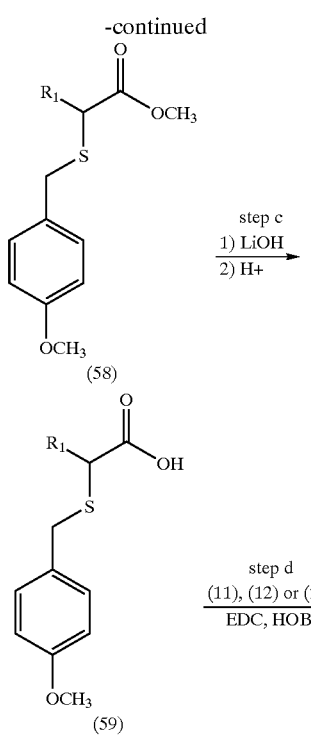

Scheme M provides an alternate general synthetic procedure for preparing compounds of structures (15), (16) and (31). All of the substituents are as defined above.

In Scheme M, step a, the thiol of structure (57a) in a suitable organic solvent such as to dimethylformamide, is degassed and treated with ethyl bromoacetate (57b) and a suitable tertiary amine such as diisopropyl ethyl amine. The reaction mixture is placed in a cooling bath and stirred for a period of time ranging from about 20 minutes to about 1 hour whereupon a precipitate is observed. The cooling bath is then removed and the reaction mixture is stirred for an additional 48 to 72 hours. The sulfide ester of structure (57) can be isolated by methods well known and appreciated in the art, such as extraction and evaporation. The sulfide ester of structure (57) can be purified as is well known in the art by chromatography and distillation.

In Scheme M, step b, the sulfide ester of structure (57) in a suitable organic solvent such as tetrahydrofuran is treated with an amide base such as lithium bis(trimethylsilyl)amide. The resulting intermediate is then reacted with an $R_1$-substituted alkyl halide ($R_1CH_2$-Hal) to yield the $R_1$-substituted sulfide ester of structure (58). The $R_1$-substituted sulfide ester of structure (58) can be isolated by methods well known and appreciated in the art, such as extraction and evaporation. The $R_1$-substituted sulfide ester of structure (58) can be purified as is well known in the art by chromatography and distillation.

In Scheme M, step c, the $R_1$-substituted sulfide ester of structure (58) is deprotected to yield the $R_1$-substituted sulfide acid of structure (59) according to the procedure described in Scheme K, step a.

In Scheme M, step d, the $R_1$-substituted sulfide acid of structure (59) is coupled with an appropriate compound of structures (1), (12) or (29) to provide an appropriate compound of structures (15), (16) or (31) according the procedures described in Scheme G.

The compounds of formula (1) wherein $R_8$ is a —C(O)—$(CH_2)_q$—K group can be synthesized according to techniques well known and appreciated by one of ordinary skill in the art, as disclosed in U.S. Pat. No. 5,424,425, issued Jun. 13, 1995. A general synthetic scheme for preparing these compounds, signified as the compounds of structure (61), is set forth in Scheme N wherein all substituents, unless otherwise indicated, are previously defined.

SCHEME N

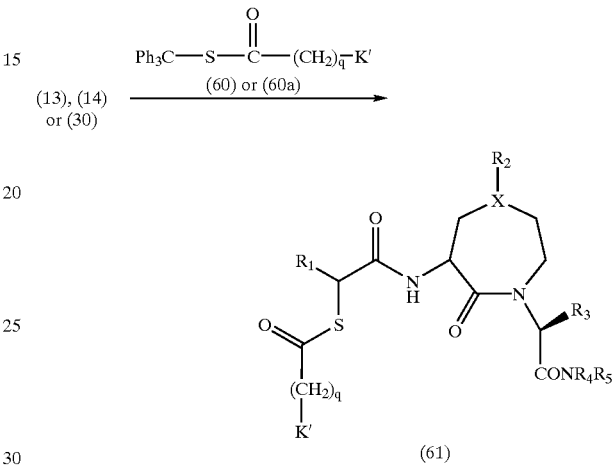

Scheme N provides a general synthetic procedure for preparing compounds of structure (61) wherein K' is

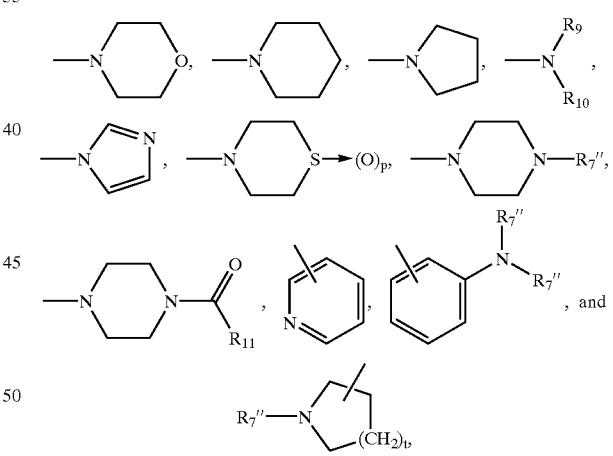

$R_7''$ represents Boc, $C_1$–$C_4$ alkyl or a —$(CH_2)_p$—$Ar_2$ group. All of the other substituents are as defined above.

In Scheme N the appropriate thioacetyl compound of structure (61) can be prepared by reacting the appropriate bromoamide of structure (13), (14) or (30) with the appropriate triphenylmethyl aminothiolacetate of structure (60 or 60a) under basic conditions such as sodium hydride, hydrogen sulfide in a suitable aprotic solvent such as dimethylformamide.

For those thioacetyl compounds of structure (61) wherein K' is

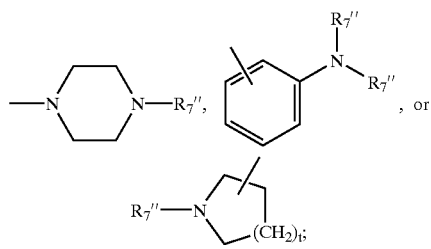, or

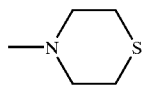

wherein R₃" is Boc, the Boc protecting group can be removed using trifluoroacetic acid to give the corresponding compounds where R₇ is hydrogen.

In addition, the sulfide functionality of those thioacetyl compounds of structure (61) is wherein K is

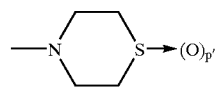

may be oxidized by techniques and procedures well known in the art, such as magnesium monoperoxyphthalic acid hexahydrate to give the thioacetyl compounds of structure (61) wherein K is —N⌐S→(O)$_{p'}$ wherein p' is 1 or 2.

Scheme O provides a general synthetic scheme for preparing the triphenylmethyl aminothiolacetates of structures (60) and (60a).

SCHEME O

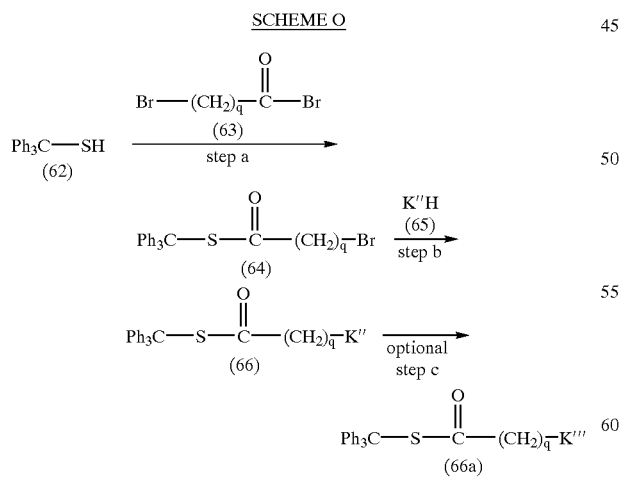

Scheme O provides a general synthetic procedure for preparing compounds of structure (64) and (64a) wherein K" is

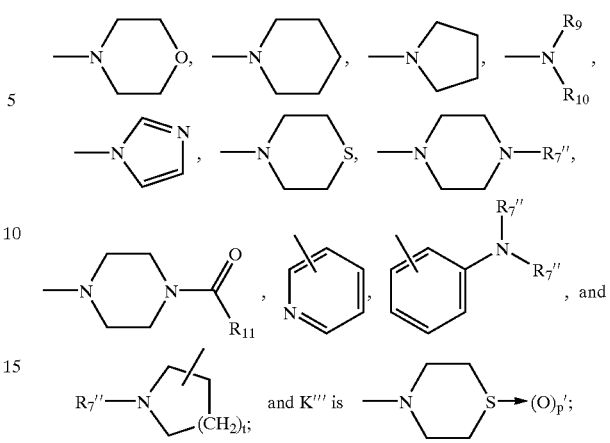

$R_7''$ represents Boc, $C_1$–$C_4$ alkyl or a —$(CH_2)_p$—$Ar_2$ group. All of the other substituents are as defined above.

In Scheme 0, step a, a triphenylmercaptan (62) and bromoacetyl bromide (63) are reacted under basic conditions, such as pyridine, in an aprotic solvent, such as methylene chloride to give triphenylmethylbromothiolacetate of structure (64).

In Scheme O, step b, triphenylmethyl bromothiolacetate of structure (64) is reacted with the appropriate amino compound of structure (65) under basic conditions, such as pyridine, in an aprotic solvent such as methylene chloride to give the appropriate triphenylmethyl aminothiolacetate compound of structure (66).

In Scheme O, optional step c, the sulfide functionality of those thioacetyl compounds of structure (66) wherein K is

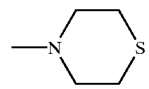

may be oxidized by techniques and procedures well known in the art, such as magnesium monoperoxyphthalic acid hexahydrate to give the thioacetyl compounds of structure (66a) wherein K is

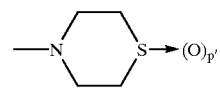

wherein p' is 1 or 2.

Alternatively, the compounds of formula (1) wherein $R_8$ is a —C(O)—$(CH_2)_q$—K group may be prepared as described in Scheme P. In Scheme P, all substituents are as previously defined unless otherwise indicated.

SCHEME P

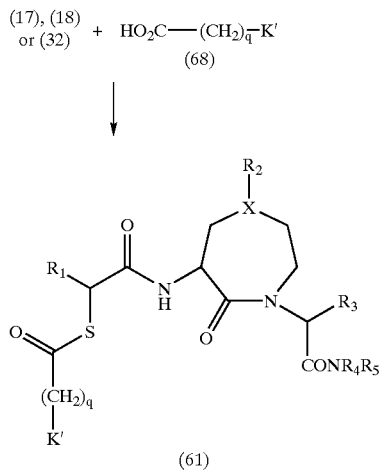

(61)

Scheme P provides a general synthetic procedure for preparing compounds of structure (61) wherein all of the substituents are as previously defined.

In Scheme P, the thiol functionality of the thiol compounds of structures (17), (18) or (32) is coupled with the appropriate acid of structure (68) in the presence of a suitable coupling agent to give the appropriate thioacetyl compound of structure (61). For example, the appropriate thiol compound of structures structures (17), (18) or (32) can be reacted with the appropriate acid of structure (68) in the presence of a coupling agent such as 2-fluoro-1-methylpyridinium p-toluenesulfate, EDC (1-(dimethylaminopropyl)-3-ethylcarbodiimide hydrochloride), carbonyldiimidazole, EEDQ (1-ethoxycarbonyl-2-ethoxy-1,2-dihydroquinoline, DCC, or diethylcyanophosphonate in a suitable aprotic solvent such as methylene chloride to give the appropriate thioacetyl compound of structure (61).

The compounds of formula (1) wherein $R_9$ is a —S—G group can be synthesized according to techniques well known and appreciated by one of ordinary skill in the art, as disclosed in PCT Int. Publ. No. WO 95/21839, published Aug. 17, 1995. A general synthetic scheme for preparing these compounds, signified as the compounds of structure (71), is set forth in Scheme Q wherein all substituents, unless otherwise indicated, are previously defined.

SCHEME Q

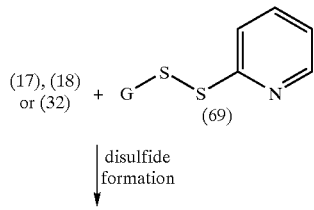

disulfide formation

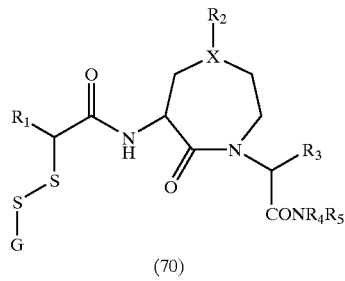

(70)

The disulfides of structure (69) can be obtained by methods known in the art or by methods known analogously in the art, Roques, B. P. et al., *J. Med. Chem.* 33, 2473–2481 (1992).

In Scheme Q, an appropriate disulfide of structure (69) is contacted with an appropriate thiol of structures (17), (18) or (32) to give a disulfide of structure (70) or a protected form thereof. An appropriate disulfide of structure (70) is one in which G is as desired in the final product of formula (1) or gives rise upon deprotection to G as is desired in the final product of formula (1).

For example, an appropriate disulfide of structure (69) is contacted with an appropriate thiol of structures (17), (18) or (32). The reaction is carried out in a suitable solvent, such as ethanol, methanol, dichloromethane, or mixtures of ethanol or methanol and dichloromethane. The solvent is degassed by passing a stream of nitrogen gas through it for 15 minutes before the reaction is carried out. The reaction is carried out using from 1.0 to 4.0 molar equivalents of an appropriate compound of structure (69). The reaction is carried out at temperatures of from 0° C. to the refluxing temperature of the solvent, with a temperature of 10° C. to 30° C. being preferred. The reaction generally requires from 1 to 48 hours. The product can be isolated by techniques well known in the art, such as extraction, evaporation, and precipitation. The appropriate disulfide or protected disulfide of structure (70) can be purified by chromatography and recrystallization.

The protected disulfides of structure (70) can be deprotected according to techniques well known in the art. The selection, use and removal of protecting groups and the removal of protecting groups in a sequential manner utilizing suitable protecting groups such as those described in *Protecting Groups in Organic Synthesis* by T. Greene is well known and appreciated by those skilled in the art.

The following examples present typical syntheses as described in Schemes A through Q. These examples are understood to be illustrative only and are not intended to limit the scope of the present invention in any way. As used herein, the following terms have the indicated meanings: "g" refers to grams; "mol" refers to moles; "mmol" refers to millimoles; "L" refers to liters; "mL" refers to milliliters; "bp" refers to boiling point; "° C." refers to degrees Celsius; "mm Hg" refers to millimeters of mercury; "mp" refers to melting point; "mg" refers to milligrams; "$\mu$M" refers to micromolar; "$\mu$g" refers to micrograms; "h" or "hrs." refers to hours, "min" refers to minutes; "HOBt" refers to hydroxybenzotriazole; "EDC" refers to 1-(3-dimethylaminopropyl)-3-ethylcarbodiimide hydrochloride; "NCEP" refers to N-carbethoxy phthalimide; and "MTBE" refers to methyl:tert-butyl ether.

EXAMPLE 1

Preparation of 2H-Isoindole-2-hexanamide. N-[hexahydro-1-[2-methylamino)-2-oxo-1-(phenylmethyl)ethyl]-2-oxo-5-phenyl-1H-azepin-3-yl]-1,3-dihydro-α-mercapto-1,3-dioxo-, [3S-[1(R*), 3α, 5α]]-; Compound II-1 (MDL 108,180)

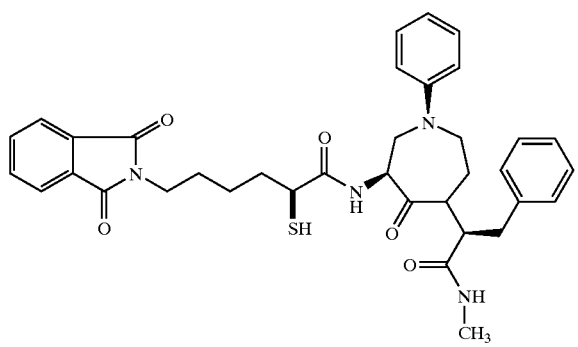

Step 1.1:

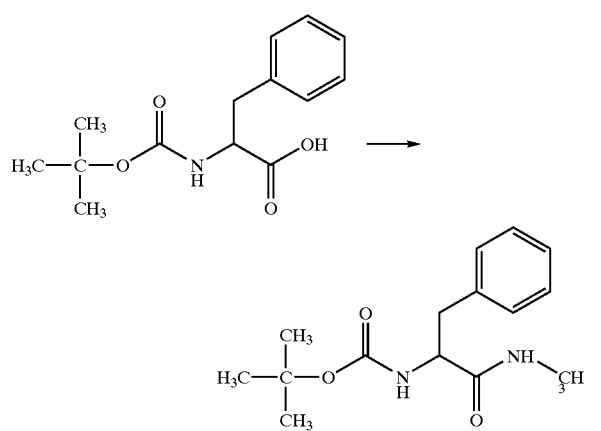

Scheme C, step a; Cool a solution of Boc-Phe-OH (8.00 g, 30.2 mmol) in tetrahydrofuran to −30° C. and treat sequentially with N-methylmorpholine (3.5 mL, 32 mmol) and isobutyl chloroformate (4.5 mL, 35 mmol). After 10 min, treat the reaction mixture with 40% aqueous methylamine (13 mL, 380 mmol), stir for 2 hours, and concentrate. Dissolve the residue in methylene chloride (125 mL) and wash with 1N hydrochloric acid and saturated NaHCO₃ (75 mL each). Dry the organic layer (NaSO₄) and concentrate to give crude title compound, which is used without further purification.

Step 1.1.1:

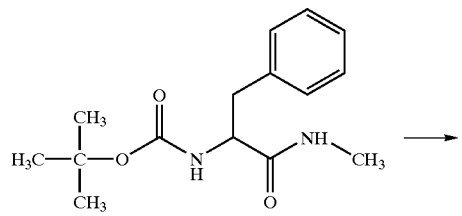

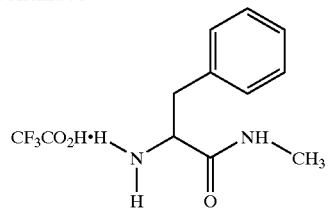

Scheme C, step b; Stir a solution of the crude product of Example 1.1 in methylene chloride (100 mL) and trifluoroacetic acid (20 mL) at ambient temperature for 3 hours and concentrate. Remove residual trifluoroacetic acid by coevaporation with carbon tetrachloride and toluene using a rotary evaporator. Triturate the sticky residue with diethyl ether to yield the title compound as a white solid (9.12 g, 100%).

Step 1.2

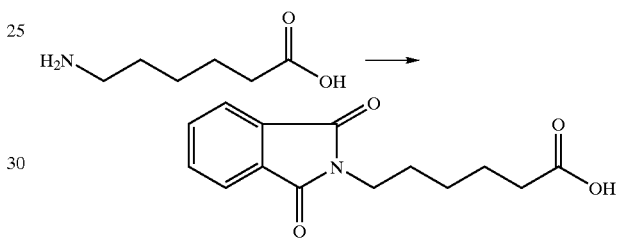

Scheme D, step a; Treat 6-aminocaproic acid (8.0 g, 60 mmol) in H₂O (100 mL) with Na₂CO₃ (6.84 g, 64 mmol) and NCEP (14.0 g, 64 mmol). Stir the reaction mixture at ambient temperature for 90 min and extract with ethyl acetate (100 mL). Cool the aqueous layer in an ice bath and acidify to pH~1 using concentrated hydrochloric acid. Collect the white precipitate by filtration, wash with water, and dry in a vacuum oven overnight to give 6-phthalimidocaproic acid (12.7 g, 80% yield).

Step 1.2.1:

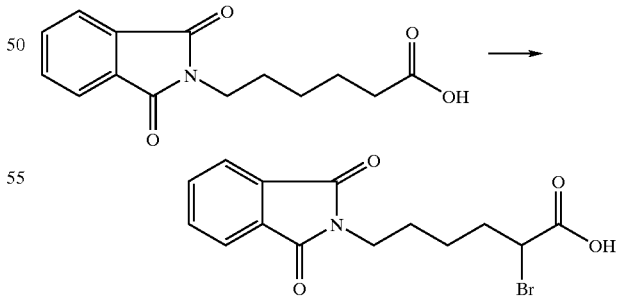

Scheme D, step b; Treat dropwise a mixture of 6-phthalimidocaproic acid (12.7 g, 48 mmol) and dry red phosphorous (1.95 g, 63 mmol) with bromine (12.7 mL, 246 mmol) at 0° C. Warm the resulting lumpy mixture to room temperature and heat to 80° C. for 3 hours. Cool the reaction mixture to room temperature, pour into water (300 mL) containing NaHSO₃, and neutralize using solid NaHCO₃. Wash the aqueous layer with diethyl ether (150 mL) and acidify with concentrated hydrochloric acid. Collect the pale yellow precipitate by filtration and dry to give 2-bromo-6-phthalimidocaproic acid (15 g, 91.5% yield).

Step 1.3:

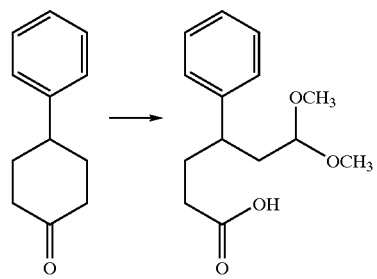

Scheme A, step a; A solution of diisopropylamine (16.2 mL, 116 mmol) in tetrahydrofuran (100 mL) at 0° C. is treated dropwise with n-butyllithium (44 mL, 110 mmol, 2.5M-hexanes). Stir for 30 min. Cool the solution to −78° C. and add a solution of 4-phenylcyclohexanone (17.42 g, 100 mmol) in tetrahydrofuran (40 mL) using a cannula. After 1 hour, quench the reaction with chlorotrimethylsilane (14 mL, 10 mmol). Stir the mixture for 45 min, and remove the cooling bath. After 2 hours, pour the reaction mixture into ice water (100 mL) and saturated aqueous NaHCO₃ solution (100 mL). Extract the mixture with pentanes (300 mL). Wash the organic layer with brine (150 mL), dry (Na₂SO₄), and concentrate to yield the silyl enol ether as a pale yellow oil (25.6 g, 104%).

Dissolve the crude silyl enol ether from above in a methylene chloride (200 mL)/methanol (300 mL) solvent mixture, cool to −78° C., and treat with ozone until a blue color persists (55 min). Purge excess ozone from the system by bubbling argon through the solution for 20 min. Add dimethyl sulfide (40 mL, 540 mmol), and the allow the reaction mixture to warm gradually to ambient temperature overnight. After 16 hours, concentrate the solution to about 150 mL, and add trimethyl orthoformate (50 nL, 460 mmol) and acetyl chloride (10 mL, 140 mmol). Heat the mixture at reflux for 4 hours and cool to ambient temperature. Add a solution of potassium hydroxide (22 g, 600 mmol) in water (100 mL). Heat the reaction mixture at 60° C. for 2 hours, cool to ambient temperature, concentrate and partition between MTBE (2×125 mL) and water (75 mL). Cool the aqueous layer in an ice bath and acidify to pH=1~2 using concentrated aqueous hydrochloric acid. Extract with methylene chloride (250 mL). Wash the organic layer with brine (75 mL), dry (Na₂SO₄), and concentrate to afford the title compound as a pale orange oil (20.3 g, 80% overall).

Step 1.3.1:

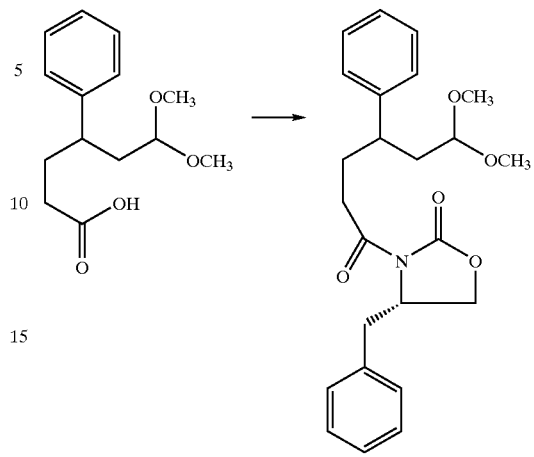

Scheme A, step b; Treat the product of Example 1.3 (16.0 g, 63.4 mmol) in tetrahydrofuran (200 mL) with triethylamine (10.6 mL, 76.1 mmol) and cool to −78° C. Add trimethylacetyl chloride (8.6 mL, 70 mmol) dropwise. After 15 min, transfer the mixture to an ice bath for 45 min, then recool to −78° C. Treat the resulting slurry via cannula with a solution of lithiated auxially which is prepared by adding n-butyllithium (28.4 mL, 71.0 mmol, 2.5 M-hexanes) to (S)-4-benzyl-2-oxazolidinone (12.94 mL, 73.0 mmol) in tetrahydrofuran (200 mL) cooling to −78° C. and stirring for 1 hour. Allow the reaction mixture to warm gradually to ambient temperature overnight. After 18 hours, add water (5 mL) and concentrate the solution. Partition the residue between saturated aqueous ammonium chloride solution (75 mL) and methylene chloride (200+125 mL). Dry the organic layer (Na₂SO₄) and concentrate. Purify the crude product by flash chromatography using hexanes:ethyl acetate (3:1 to 3:2) to afford the desired acyloxazolidinone as a light tan oil (22.13 g, 85%).

Step 1.3.2:

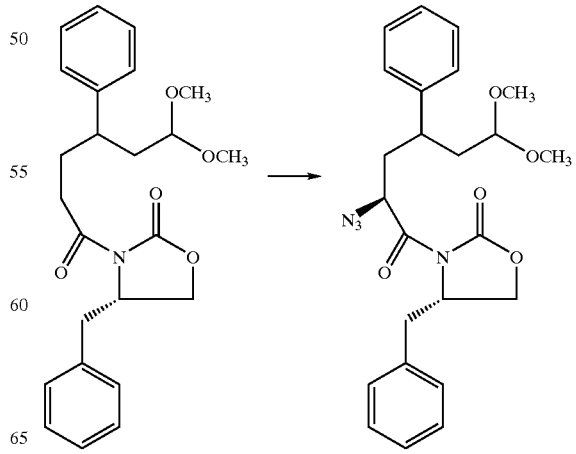

Scheme A, step c; Cool a solution of potassium bis(trimethylsilyl)amide (58 mL, 29 mmol, 0.5 M-toluene) in tetrahydrofuran (50 mL) to −78° C. and treat dropwise via cannula with a solution of acyloxazolidinone (10.58 g, 25.71 mmol) in tetrahydrofuran (100 mL), precooled to −78° C. After 30 min, add a solution of triisopropylbenzenesulfonyl azide (9.90 g, 32 mmol) in tetrahydrofuran (50 mL), precooled to −78° over 10 min using a cannula. Stir the solution for 3 min, quench with acetic acid (6.9 mL, 120 mmol), stir for 5 min, and transfer to an oil bath (35° C.). After 1.5 h, cool the suspension to ambient temperature, and add water to obtain a solution. Concentrate the solution, and partition the residue between saturated aqueous ammonium chloride solution (75 mL) and ethyl acetate (350 mL). Wash the organic layer with saturated aqueous NaHCO$_3$:brine (1:1=75 mL), dry (Na$_2$SO$_4$) and concentrate. Triturate the residue with chloroform/methylene chloride and filter. Concentrate the filtrate, and purify the crude material by flash chromatography using hexanes:ethyl acetate (3:1 to 3:2) to afford the desired α-azidoacyloxazolidinone as a pale yellow oil (9.96 g, 86%).

Step 1.3.3:

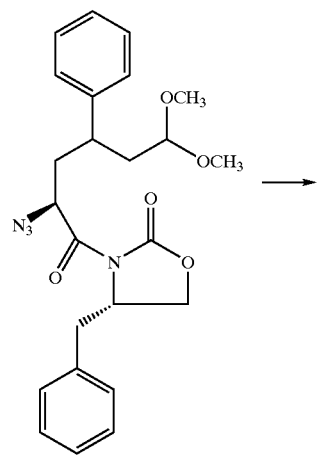

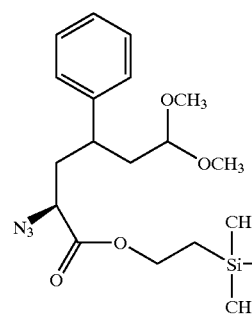

Scheme A, step d; Cool α-azidoacyloxazolidinone (9.86 g, 21.8 mmol) in tetrahydrofuran (300 mL)/water (90 mL) in an ice bath and treat sequentially with 30% aqueous H$_2$O$_2$ (8.8 mL, 77 mmol) then lithium hydroxide (1.05 g, 43.8 mmol). Stir the mixture for 1.5 h at ambient temperature and add Na$_2$SO$_3$ (12 g, 95 mmol) in water (68 mL). Remove the tetrahydrofuran using a rotary evaporator. Extract the aqueous layer with diethyl ether (2×125 mL), cooled in an ice bath, acidified to pH 1–2 using 6 N HCl, and extract with methylene chloride (2×200 mL). Dry the organic layer (Na$_2$SO$_4$) and concentrate to afford the desired acid as a pale yellow oil (7.19 g, 112%).

Treat sequentially the so formed α-azidoacid (21.8 mmol) in tetrahydrofuran (120 m/L) at ambient temperature with 2-trimethylsilylethanol (9.4 mL, 66 mmol), pyridine (5.3 mL, 66 mmol), and EDC (8.40 g, 44 mmol). Stir the mixture for 2.5 days and concentrate. Dissolve the mixture in MTBE (150 mL), and wash the solution sequentially with 5% aqueous sulfuric acid, saturated NaHCO$_3$, and brine (50 mL each). Dry the organic layer (Na$_2$SO$_4$) and concentrate. Purify the residue by flash chromatography using hexanes:ethyl acetate (7:1 to 6:1) to afford the title compound as a colorless oil (7.09 g, 83%).

Step 1.3.4:

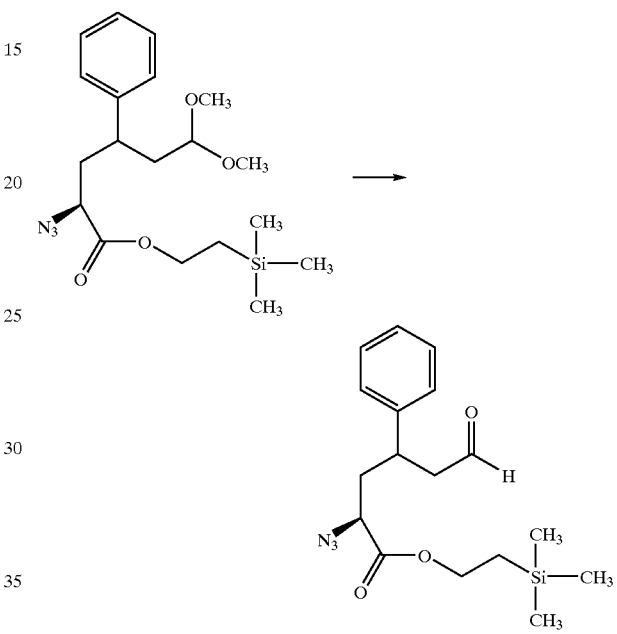

Scheme A, step e; Heat a solution of the product of example 1.3.3 (3.00 g, 7.62 mmol) in acetic acid (30 mL), water (10 mL), and tetrahydrofuran (10 mL) in an oil bath at 60° C. for 4 h. Cool the solution to ambient temperature and concentrate using a rotary evaporator (bath temperature=40° C.). Partition the residue between MTBE (125 mL) and brine (50 mL). Wash the organic layer with saturated aqueous NaHCO$_3$:brine (1:1=50 mL), dry (Na$_2$SO$_4$) and concentrate. Purify the residue by flash chromatography using hexanes:ethyl acetate (6:1) to afford the title compound as a colorless oil (2.52 g, 95%).

Step 1.3.5:

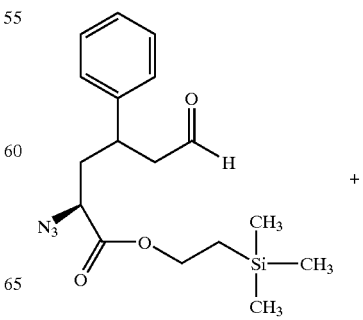

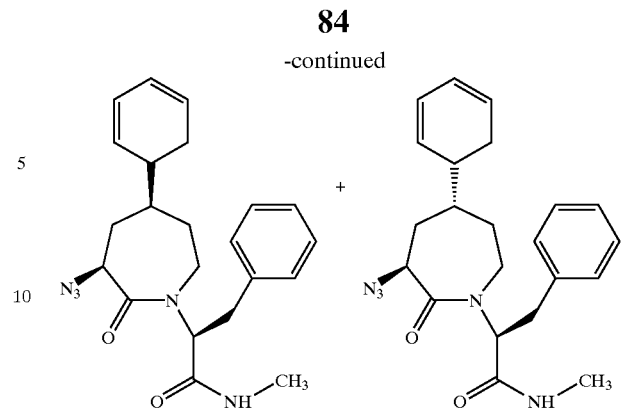

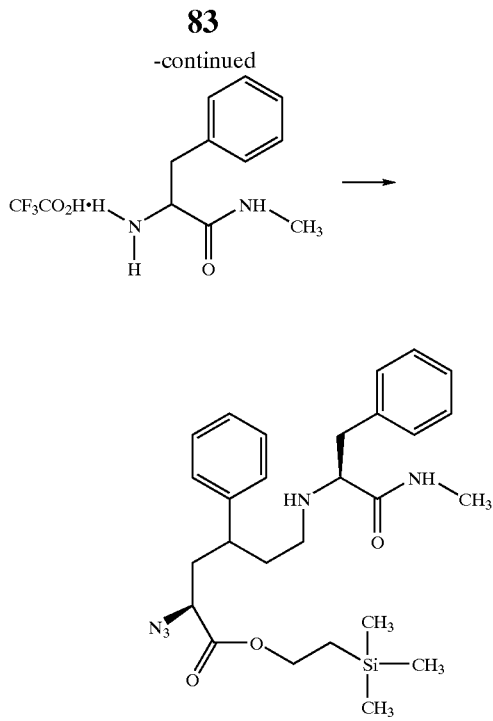

Scheme A, step f; Treat a solution of the product of example 1.3.4 (717 mg, 2.06 mmol) and the amine salt product of Step 1.1.1 (1.81 g, 6.19 mmol) in methanol (20 mL) with powdered activated 3A sieves. After 30 min, add sodium cyanoborohydride (0.73 mL, 0.73 mmol, 1.0M-THF). Stir the reaction mixture for 2.5 h, filter through a pad of Celite®, and concentrate. Dissolve the residue in methylene chloride (100 mL) and wash with saturated aqueous NaHCO₃:brine (1:1=30 mL). Dry the organic layer (Na₂SO₄) and concentrate. Purify the product mixture by flash chromatography using hexanes:ethyl acetate (1:1 to 1:2) to afford the title compound as a viscous colorless oil (737 mg, 70%).

Step 1.3.6:

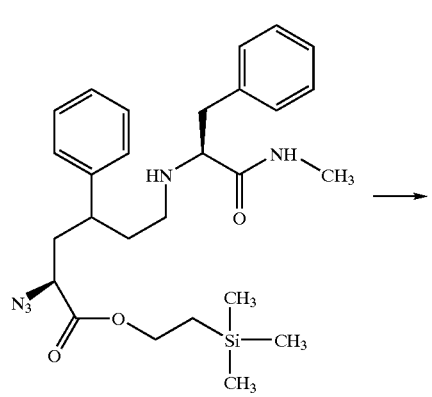

Scheme A, step g; Treat a solution of the product of example 1.3.5 (737 mg, 1.45 mmol) in tetrahydrofuran (15 mL) at ambient temperature with tetra-n-butylammonium fluoride (2.2 mL, 2.2 mmol, 11.0M-THF) and stir. After 3 h, concentrate the solution. Dissolve the residue in ethyl acetate (125 mL) and wash with 10% aqueous HCl (30 mL) and brine (25 mL). Dry the organic layer (Na₂SO₄) and concentrate to yield crude amino acid (0.72 g, 122%). Dissolve this material in tetrahydrofuran (27 mL), cool in an ice bath, and treat sequentially with N-methylmorpholine (0.35 mL, 3.2 mmol) and isobutyl chloroformate (0.24 mL, 1.85 mmol). Stir the suspension for 2.5 h and filter. Wash the salts with dry tetrahydrofuran and concentrate the filtrate. Purify the residue by radial chromatography using hexanes-:ethyl acetate (1:1 to 2:3) to afford separately, the cis- (230 mg, 41%) and trans- (290 mg, 51%) isomers of the title compound.

Step 1.3.7:

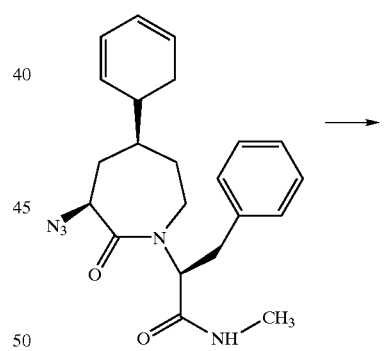

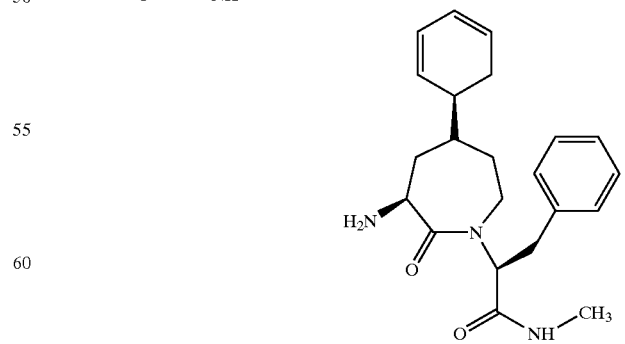

Scheme A, step h1; Degas (vacuum-N₂) a solution of the cis-isomer of the product of example 1.3.6 (145 mg, 0.370 mmol) in methanol (6 mL) and treat with 1,3-propanedithiol (0.20 mL, 1.99 mmol) and triethylamine (0.27 mL, 1.94 mmol). Stir the solution for 66 h and concentrate. Purify the residue by flash chromatography using methylene chloride:methanol (100:0, then 95:5 to 90:10) to afford the title compound as a colorless oil (140 mg, 104%).

Step 1.3.8:

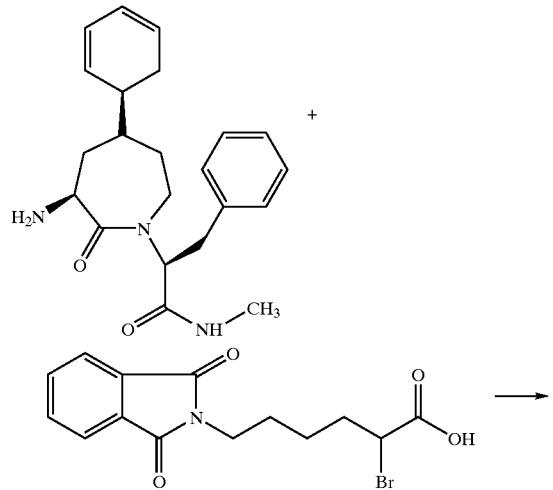

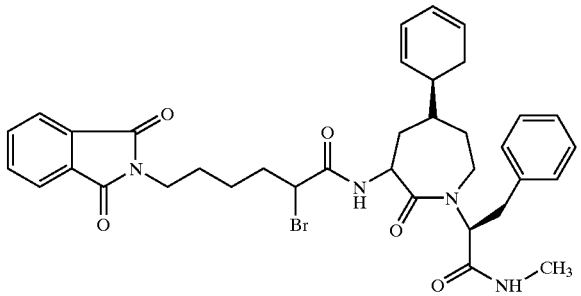

Scheme A, step i1; Stir a mixture of the product of example 1.3.7 (135 mg, 0.370 mmol), 2-bromo-6-phthalimidocaproic acid (189 mg, 0.56 mmol, example 1.2.1), EDC (106 mg, 0.55 mmol) and HOBt (75 mg, 0.56 mmol) in methylene chloride (8 mL) at ambient temperature for 18 h. Concentrate the reaction mixture and partition between ethyl acetate (60 mL) and 5% aqueous sulfuric acid (15 mL). Wash the organic layer with saturated NaHCO₃, then brine (15 mL each), dry (Na₂SO₄), and concentrate. Purify the crude product by flash chromatography using hexanes:ethyl acetate (2:3 to 1:3) to afford the title compound as a white foam (220 mg, 87%).

Step 1.3.9:

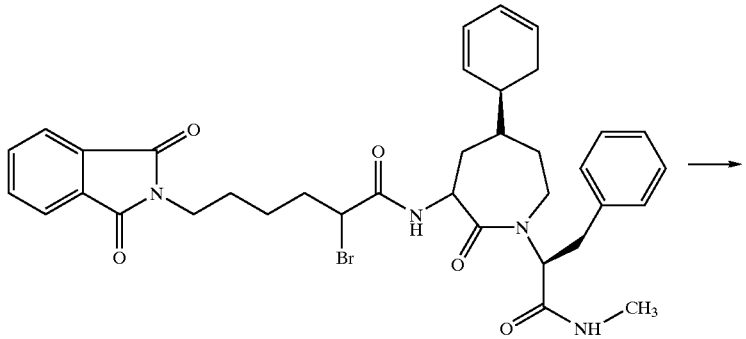

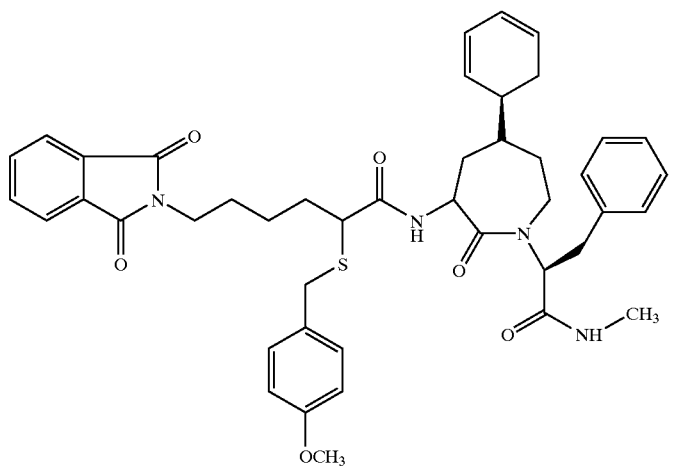

Scheme A, step j 1; Degas (vacuum-$N_2$) a solution of p-methoxybenzylmercaptan (0.09 mL, 0.65 mmol) in dimethylformamide (3 mL) and treat with sodium hydride (20 mg, 0.50 mmol, 60% oil dispersion). After 1 h, add a solution of the product of example 1.3.8 (220 mg, 0.320 mmol) in dimethylformamide (2 mL+3 mL wash) to the mercaptide using a cannula. Add a spatula tip of tetra-n-butylammonium iodide as a catalyst. Stir the reaction mixture for 20 h and add saturated aqueous ammonium chloride solution (25 mL) and water (5 mL). Extract the solution with ethyl acetate (75 mL) and wash the organic layer with brine (25 mL). Back-extract the combined aqueous layers with ethyl acetate (50 mL). Dry the combined organic layers ($Na_2SO_4$), concentrate, and place under high vacuum. Purify the crude product by flash chromatography using methylene chloride:ethyl acetate (2:1 to 1:2) to afford the title compound as a white foam (194 mg, 80%).

Step 1.3.10:

Scheme A, step k1; Cool a mixture of the product of example 1.3.9 (194 mg, 0.255 mmol), mercuric acetate (102 mg, 0.32 mmol), and anisole (0.28 mL, 2.55 mmol) in methylene chloride (8 mL) in an ice bath, degas (vacuum-$N_2$) and treat with trifluoroacetic acid (2.5 mL). After 4 h, bubble $H_2S$ gas through the reaction mixture for 15 min. Filter the black precipitate and wash with methylene chloride. Concentrate the filtrate and remove residual trifluoroacetic acid by coevaporation with carbon tetrachloride. Triturate the residue with hexanes to yield the title compound (MDL 108,180) as a light tan solid (150 mg, 92%). IR(KBr) 702, 721, 752, 962, 1045, 1173, 1209, 1366, 1398, 1437, 1494, 1643, 1711, 1773, 2862, 2940, 3028, 3380 $cm^{-1}$; $^1H$ NMR ($CDCl_3$) δ 1.34–1.81 (m, 6), 1.87–2.11 (m, 4), 2.82 (d, 3, J=4.9), 2.90–3.06 (m, 2), 3.13–3.34 (m, 3), 3.48 (dd, 1, J=11,16), 3.67 (t, 2, J=7.3), 3.69–3.76 (m, 1), 4.59–4.66 (m, 1), 5.03 (t, 1, J=8.1), 6.32–6.39 (m, 1),

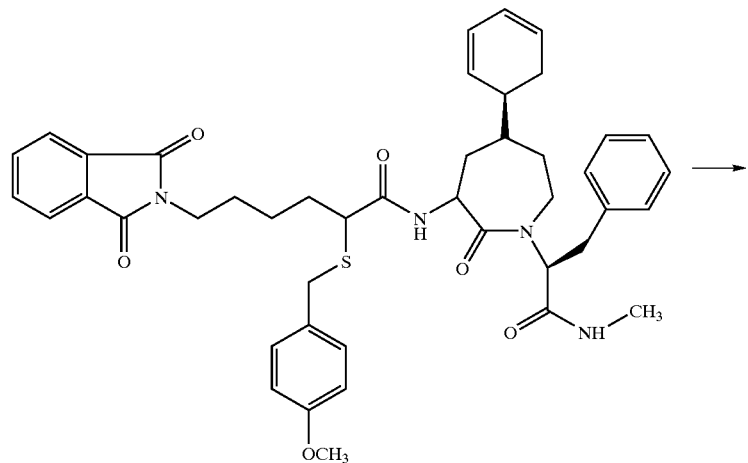

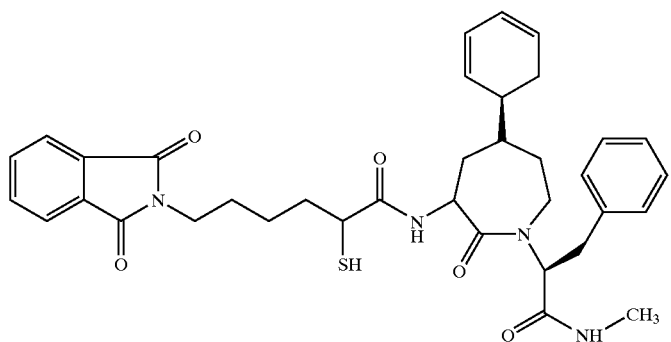

7.00–7.03 (n, 2), 7.15–7.35 (m, 8), 7.60–7.65 (m, 1), 7.68–7.73 (m, 2), 7.78–7.84 (m, 2).
MW Calcd for $C_{36}H_4N_4O_5S$=640.8.
Found (M+H+)=641.

EXAMPLE 2

Preparation of 2H-Isoindole-2-hexanamide, N-[hexahydro-1-[2-(methylamino)-2-oxo-1-(phenylmethyl)ethyl]-2-oxo-5-phenyl-1H-azepin-3-yl]-1,3-dihydro-α-mercapto-1,3-dioxo-, [3S-[1(R*), 3α, 5β]]-; Compound III-1 (MDL 106,540)

Step 2.1:

Scheme A, step h2; Prepare by the method of example 1.3.7 using the trans-isomer of example 1.3.6 (290 mg, 0.740 mmol). Purify by flash chromatography using methylene:methanol (100:0, then 95:5 to 90:10) to give the title compound (249 mg, 92%).

Step 2.2:

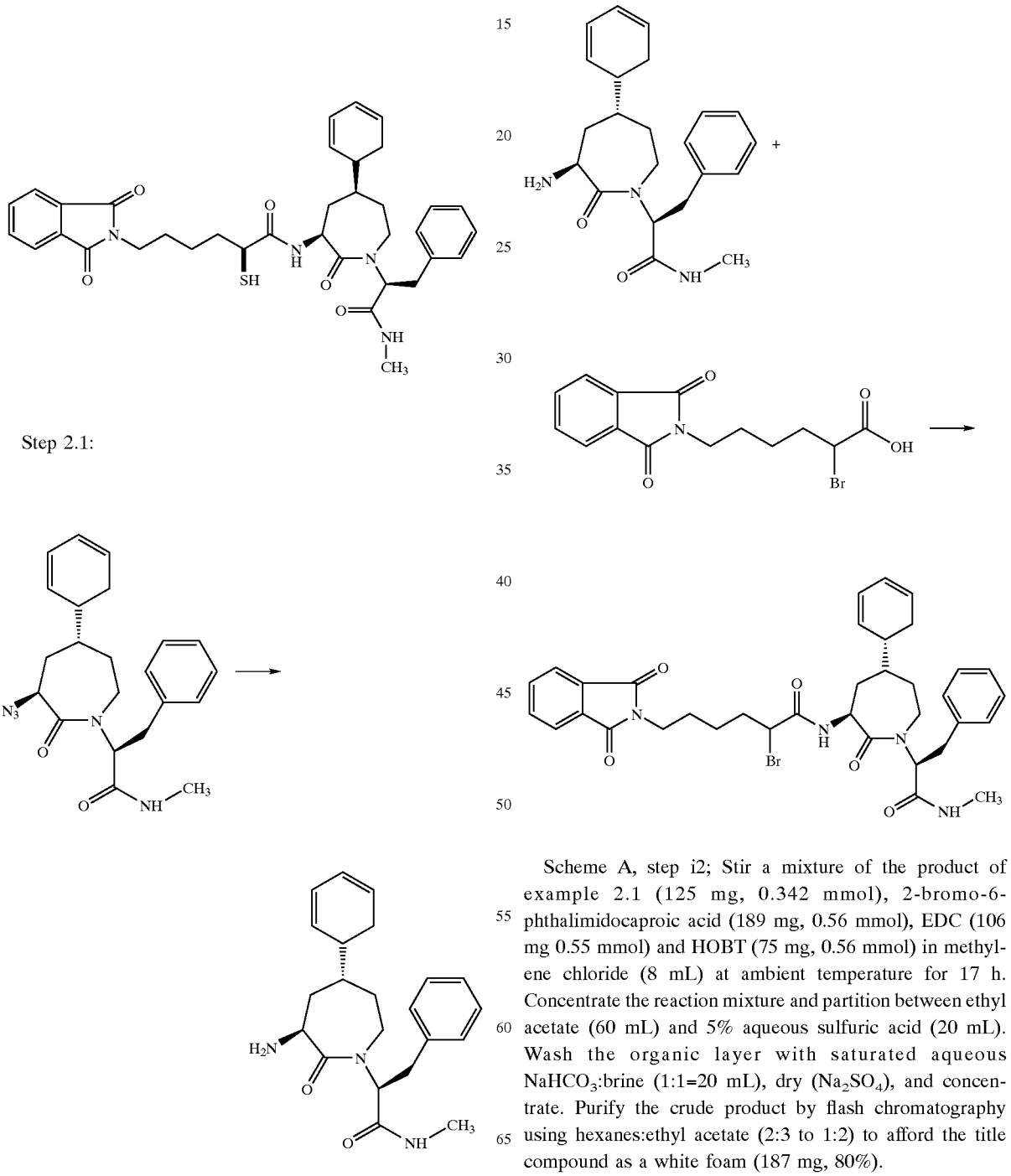

Scheme A, step i2; Stir a mixture of the product of example 2.1 (125 mg, 0.342 mmol), 2-bromo-6-phthalimidocaproic acid (189 mg, 0.56 mmol), EDC (106 mg 0.55 mmol) and HOBT (75 mg, 0.56 mmol) in methylene chloride (8 mL) at ambient temperature for 17 h. Concentrate the reaction mixture and partition between ethyl acetate (60 mL) and 5% aqueous sulfuric acid (20 mL). Wash the organic layer with saturated aqueous $NaHCO_3$:brine (1:1=20 mL), dry ($Na_2SO_4$), and concentrate. Purify the crude product by flash chromatography using hexanes:ethyl acetate (2:3 to 1:2) to afford the title compound as a white foam (187 mg, 80%).

Step 2.3:

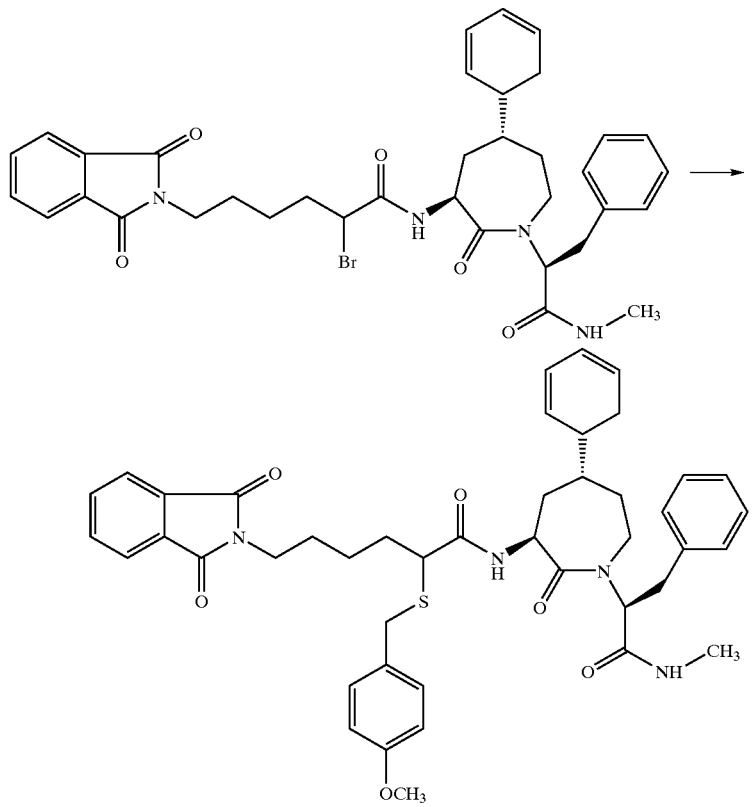

Scheme A, step j2; Degas a solution of the product of example 2.2 (150 mg, 0.22 mmol), p-methoxybenzylmercaptan (0.08 mL, 0.57 mmol), and tetra-n-butylammonium iodide (spatula tip, catalyst), in dimethylformamide (3 mL) and treat at ambient temperature with cesium carbonate (94 mg, 0.29 mmol). After 24 h, add saturated aqueous ammonium chloride solution (20 mL) and water (5 mL). Extract the solution with ethyl acetate (75 mL), and wash the organic layer with brine (2×20 mL). Dry ($Na_2SO_4$) the combined organic layer, concentrate, and place under high vacuum. Purify the crude product by flash chromatography using hexanes:ethyl acetate (2:3 to 1:2) to give the title compound as a white foam (160 mg, 77%).

Step 2.4:

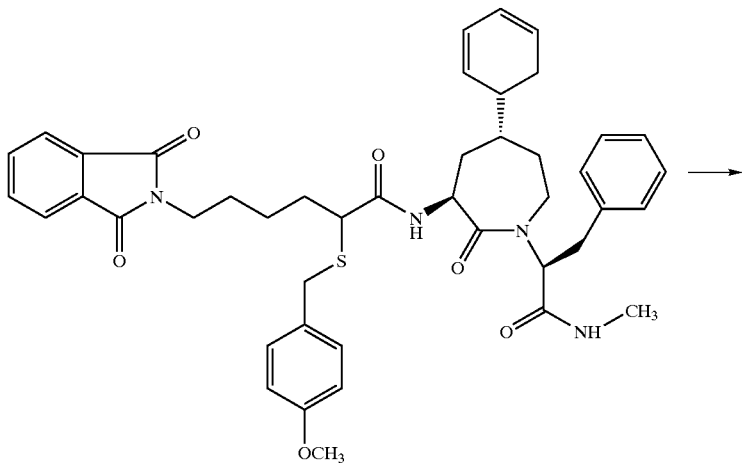

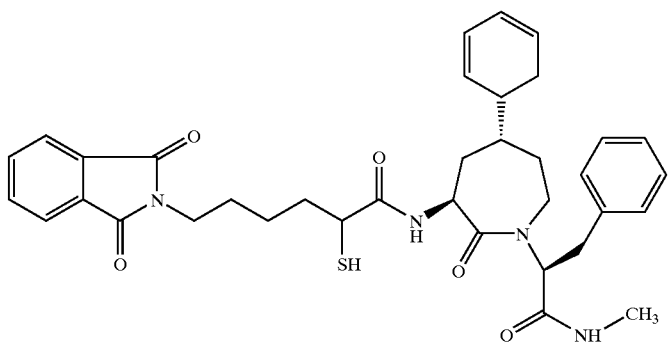

Scheme A, step k2; Cool a mixture of the product of example 2.3 (160 mg, 0.210 mmol), mercuric acetate (84 mg, 0.26 mmol), and anisole (0.23 mL, 2.10 mmol) in methylene chloride (6.6 mL) in an ice bath, degas and treat with trifluoroacetic acid (3 mL). After 4 h, bubble H$_2$S gas through the reaction mixture for 15 min. Filter the black precipitate and wash with methylene chloride. Concentrate the filtrate and remove residual trifluoroacetic acid by coevaporation with carbon tetrachloride. Purify the residue by flash chromatography using hexanes:ethyl acetate (1:1 to 1:2) to yield the title compound (MDL 106,540) as a light tan solid (96 mg, 71%). IR(KBr) 702, 721, 1337, 1366, 1398, 1437, 1454, 1468, 1497, 1530, 1645, 1678, 1710, 1770, 2938, 3380 cm$^{-1}$; $^1$H NMR (CDCl$_3$) δ 1.35–1.80 (m, 7), 1.94–2.10 (m, 2), 1.96 (d, 0.5, J=8.7), 1.97 (d, 0.5, J=8.8), 2.50–2.70 (m, 2), 2.81 (d, 1.5, J=4.8), 2.82 (d, 1.5, J=4.8), 2.91–3.00 (m, 1), 3.22–3.29 (m, 1), 3.31–3.39 (m, 1), 3.47–3.58 (m, 1), 3.67 (t, 2, J=7.2), 3.72–3.80 (m, 1), 4.82–4.90 (m, 1), 5.25 (t, 1, J=7.8), 6.07–6.10 (m, 1), 7.15–7.30 (m, 10), 7.48–7.55 (m, 1), 7.66–7.72 (m, 2), 7.78–7.84 (m, 2).

MW Calcd for C$_{36}$H$_{40}$N$_4$O$_5$S=640.8.
Found (M+H)+=641.

EXAMPLE 3

Preparation of 2H-Isoindole-2-hexanamide, N-[hexahydro-4-[2-(methylamino)-2-oxo-1-(phenylmethyl)ethyl]-5-oxo-1-(phenylmethyl)-1H-1,4-diazepin-6-yl]-1,3-dihydro-α-mercapto-1,3-dioxo-, [6S-[4(R*), 6R*(R*)]]-: Compound IV-1

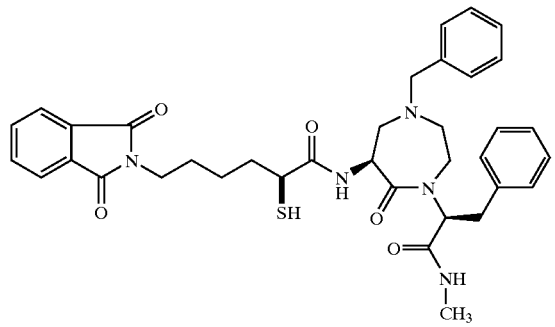

Step 3.1:

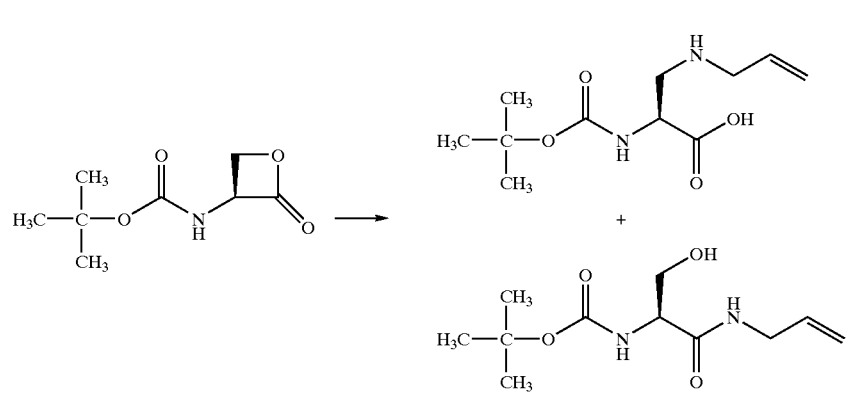

Scheme B, step b; A solution of N-tert-butoxycarbonyl-L-serine β-lactone (1.00 g, 5.82 mmol; Pansare, S. V. et al., *Org. Synth.* 70, 10 (1991)) in CH₃CN (100 mL) is added dropwise over 1.5 h to a solution of allyl amine (10 mL, 133 mmol) in CH₃CN (200 mL). After 1 h, the solution is concentrated, and the solid residue is triturated with CH₃CN to afford the desired amino acid as a white solid (648 mg, 46%). The filtrate is concentrated to yield the hydroxyamide byproduct as a white solid (632 mg, 44%).

Step 3.2

Step 3.3

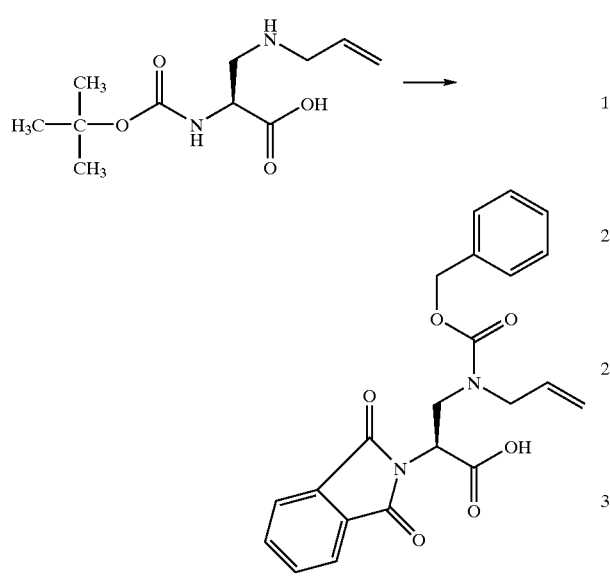

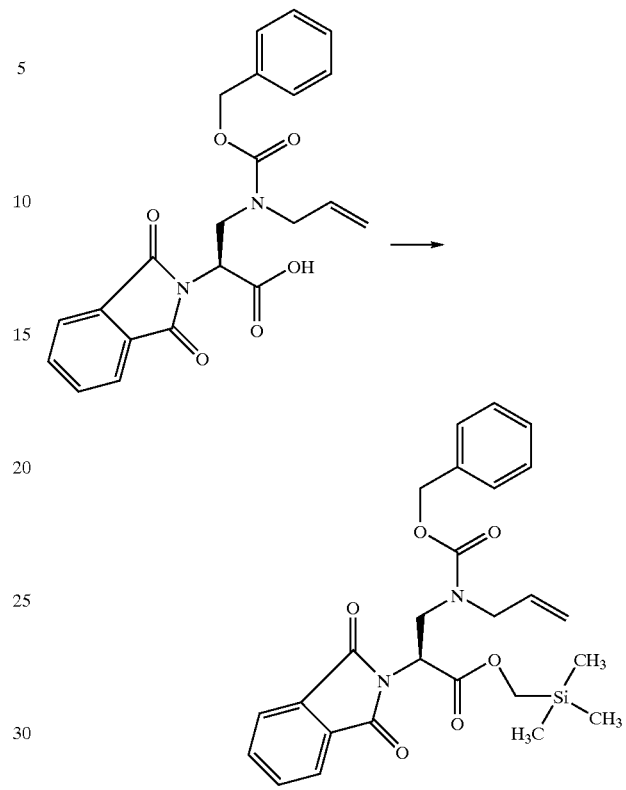

Scheme B, step c; A solution of the amino acid product of Step 3.1 (640 mg, 2.62 mmol) in saturated aqueous NaHCO₃ (7.5 mL) and water (1 mL) is treated at ambient temperature with a solution of benzyl chloroformate (0.42 mL, 2.94 mmol) in acetone (1 mL) over 5 min. The cloudy reaction mixture is stirred for 2 h. The resulting solution is partitioned between MTBE (40 mL) and water (25 mL). The aqueous layer is cooled in an ice bath, brought to about pH 2 using 5% aqueous HCl, saturated with NaCl, and extracted with methylene chloride (2×45 mL). The combined organic layers are dried (Na₂SO₄) and concentrated to give the CBz-protected amino acid as a colorless oil (1.14 g). A solution of the CBz-protected amino acid (1.14 g) in methylene chloride (100 mL) and trifluoroacetic acid (20 mL) is stirred at ambient temperature for 1 h and concentrated. Residual trifluoroacetic acid is removed by coevaporation with carbon tetrachloride using a rotary evaporator to give the amino acid tfa salt (1.27 g).

A solution of the amino acid tfa salt (1.27 g) in water (25 mL), dioxane (10 mL) and solid Na₂CO₃ (306 mg, 2.88 mmol) is treated with NCEP (945 mg, 4.32 mmol) and stirred at 40° C. After 4 h, additional Na₂CO₃ (306 mg) is added to bring the mixture from about pH 4 to about pH 8–10. NCEP (630 mg, 2.87 mmol) is added, and the reaction mixture is stirred for 16 h and concentrated. Water (40 mL) is added and the mixture is extracted with MTBE (40 mL). The aqueous layer is cooled in an ice bath, acidified to about pH 1 with 6N HCl, and extracted with methylene chloride (60 mL) then ethyl acetate (60 mL). The organic layer is dried (Na₂SO₄) and concentrated. The product mixture is purified by flash chromatography using hexanes:ethyl acetate: acetic acid (1:1:0.1) to afford the desired phthalimido acid (1.2 g).

Scheme B, step d; The phthalimido acid product of Step 3.2 (1.2 g) in tetrahydrofuran (25 mL) and methylene chloride (10 mL) is treated sequentially at ambient temperature with 2-trimethylsilylethanol (1.2 mL, 8.4 mmol), pyridine (0.68 mL, 8.4 mmol), and EDC (1.26 g, 6.55 mmol). The mixture is stirred 18 h and concentrated. The residue is dissolved in MTBE (75 mL), and the solution is washed sequentially with 5% aqueous sulfuric acid and saturated aqueous NaHCO₃:brine=1:1 (40 mL each). The organic layer is dried (Na₂SO₄) and concentrated. The residue is purified by flash chromatography using methylene chloride: ethyl acetate (100:0 to 95:5) to afford the desired ester as a colorless oil (1.12 g, 84% overall).

Step 3.4

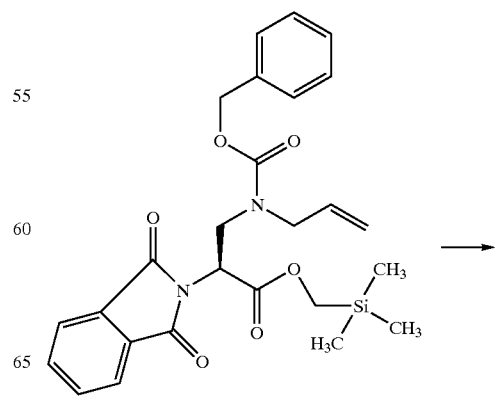

-continued

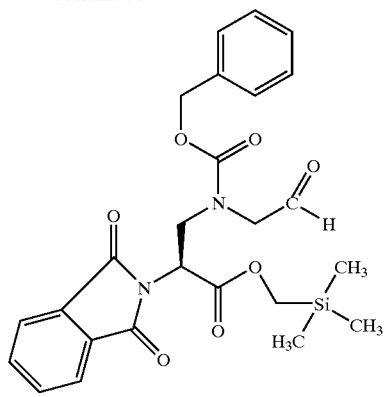

Scheme B, step e; A solution of the ester product of Step 3.3 (1.12 g, 2.20 mmol) in methylene chloride (30 mL) and methanol (3 mL) is cooled to −78° C. under argon. Ozone is passed through the solution until a blue color persists. The excess ozone is purged by in bubbling argon through the solution for 15 min. Dimethyl sulfide (3 mL) is added and the solution is allowed to warm gradually to ambient temperature overnight. After 15 h, the reaction mixture is diluted with methylene chloride (100 mL) and washed with brine (40 mL). The organic layer is dried ($Na_2SO_4$) and concentrated. The product mixture is purified by flash chromatography using hexanes:ethyl acetate (3:2 to 1:1) to afford the desired aldehyde (1.11 g, 99%).

Step 3.5

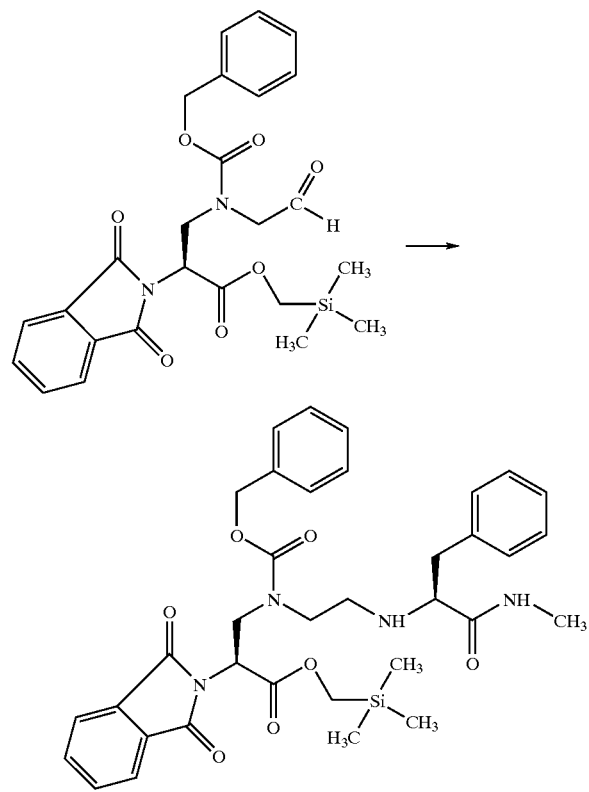

Scheme B, step f; A solution of aldehyde (1.11 g, 2.17 mmol) and amine salt product of Step 1.1.1 (1.84 g, 6.29 mmol) in methanol (23 mL) is stirred 10 min and treated with sodium cyanoborohydride (2.2 mL, 2.2 mmol, 1.0M-THF). The reaction mixture is stirred 3 h and concentrated. The residue is dissolved in methylene chloride (1250 mL) and washed with saturated aqueous $NaHCO_3$:brine (1:1=40 mL). The organic layer is dried ($Na_2SO_4$) and concentrated. The product mixture is purified by flash chromatography using hexanes:ethyl acetate (3:2 to 1:2) to afford the desired amino-ester as a white foam (1.32 g, 90%).

Step 3.6

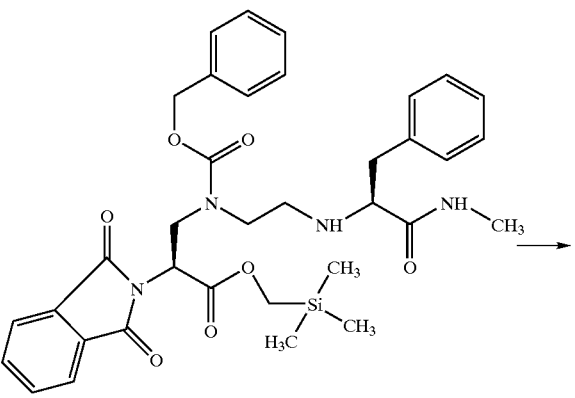

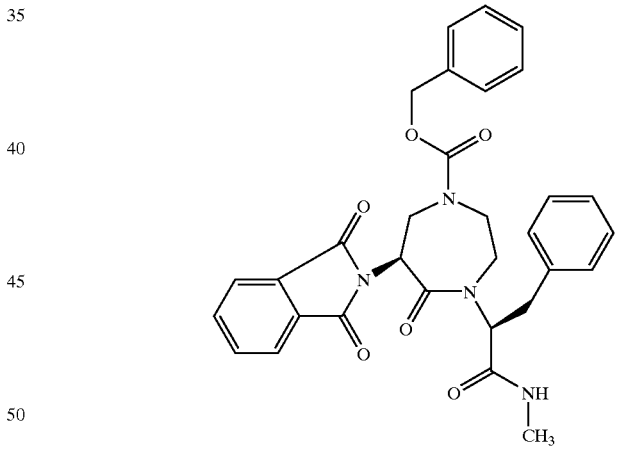

Scheme B, step g; A solution of the silyl ester product of Step 3.5 (1.30 g, 1.93 mmol) in tetrahydrofuran (20 mL) is treated at ambient temperature with tetra-n-butylammonium fluoride (3.0 mL, 3.0 mmol, 1.0M-THF) and stirred. After 1.5 h, the solution is concentrated. The residue is dissolved in ethyl acetate (125 mL) and washed with 10% aqueous hydrochloric acid (30 mL) and brine (25 mL). The organic layer is dried ($Na_2SO_4$) and concentrated to yield crude amino acid (1.54 g). This material is dissolved in tetrahydrofuran (36 mL), cooled in an ice bath, and treated sequentially with N-methylmorpholine (0.47 mL, 4.27 mmol) and isobutylchloroformate (0.32 mL, 2.47 mmol). The suspension is stirred for 4 h and filtered through a pad of Celite®. The salts are washed with dry tetrahydrofuran, and the filtrate is concentrated. The residue is purified by flash chromatography using hexanes:ethyl acetate (3:2 to 1:1) to afford the lactam (954 mg, 89%).

Step 3.7

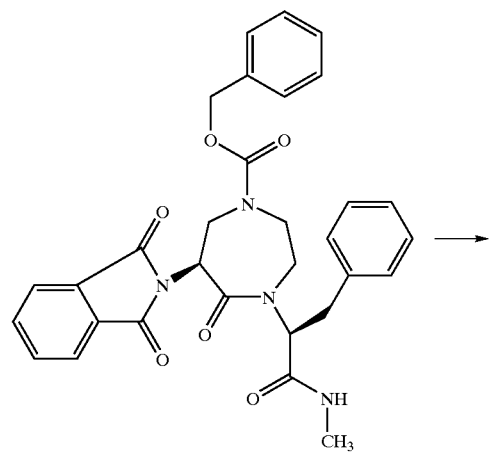

Scheme B, step h; A solution of the Z-lactam product of Step 3.6 (954 mg, 1.72 mmol) in methanol (17 mL) is degassed (vacuum-N₂), treated with 10% Pd—C (500 mg), and stirred under a H₂ atmosphere (balloon) for 15 h. Additional catalyst (250 mg) is added, the mixture is stirred 7 h, degassed and filtered. The filtrate is concentrated to yield the desired product (720 mg, 100%).

Step 3.8

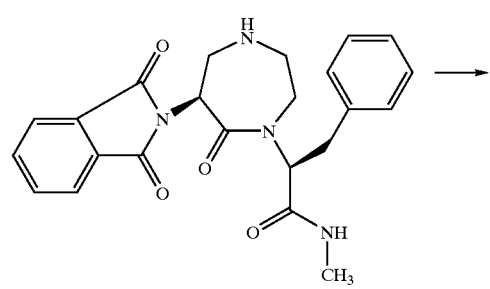

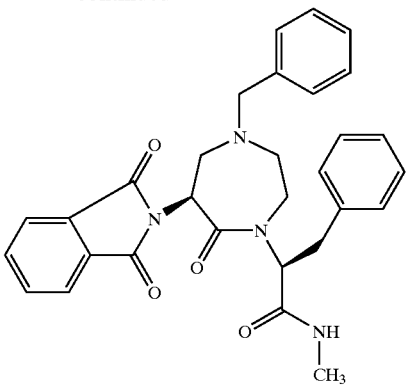

Scheme B, step i; A solution of the amine product of Step 3.7 (720 mg, 1.71 mmol) in CH₃CN (10 mL) and dimethylformamide (3 mL) is treated with benzyl bromide (0.30 mL, 2.5 mmol) and solid K₂CO₃ (130 mg, 0.94 minor). After 18 h, the mixture is concentrated, and the residue is partitioned between ethyl acetate (75 mL) and water (15 mL). The organic layer is dried (Na₂SO₄) and concentrated. The product mixture is purified by flash chromatography using hexanes:ethyl acetate (1:2) to afford the desired product (500 mg, 57%).

Step 3.9

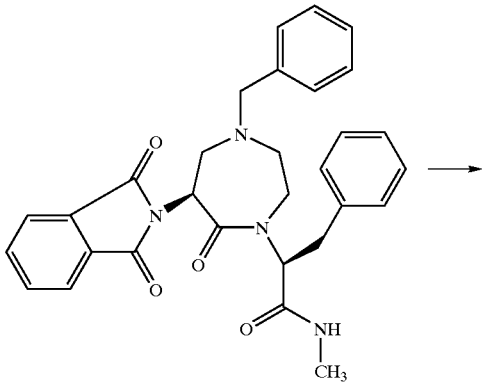

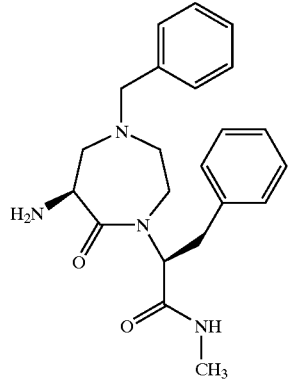

Scheme B, step j; A solution of the phthalimido lactam of Step 3.8 (500 mg, 0.979 mmol) in methanol (10 mL) is treated at ambient temperature with hydrazine hydrate (2.0 mL, Step 3.11

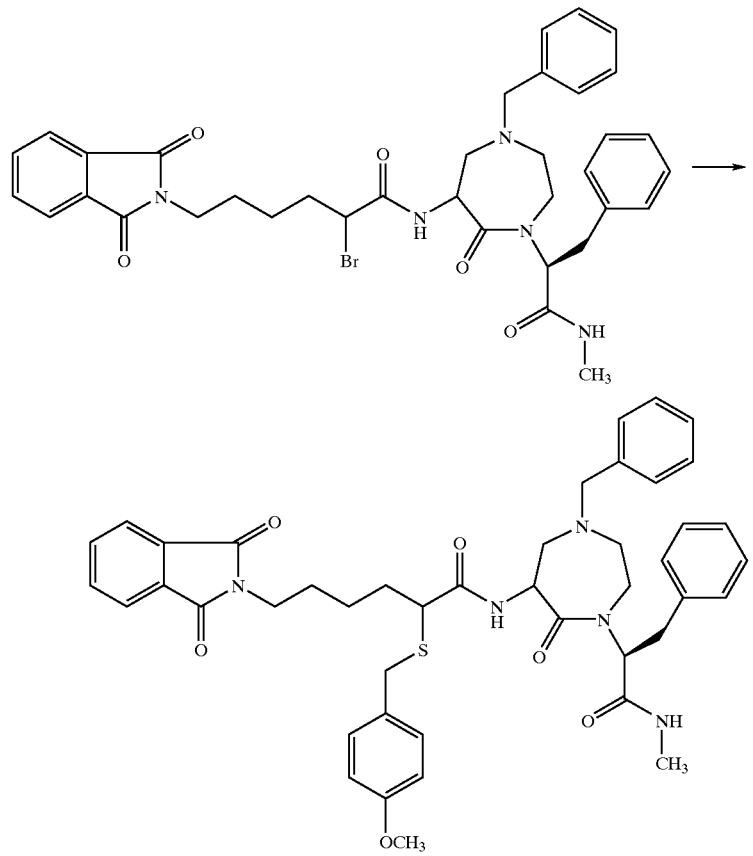

Scheme B, step 1; A solution of bromoamide of Step 3.10 (500 mg, 0.714 mmol) and p-methoxybenzylmercaptan (0.35 mL, 2.5 mmol) in dimethylformamide (5 mL) is degassed (vacuum-$N_2$) and treated at ambient temperature with cesium carbonate (400 mg, 1.22 mmol). After 18 h, the orange suspension is concentrated, and the residue is partitioned between ethyl acetate (75 mL) and water (15 mL). The organic layer is dried ($Na_2SO_4$) and concentrated. The crude product is purified by flash chromatography using ethyl acetate to afford the α-thioamide (326 mg, 59%).

Step 3.12

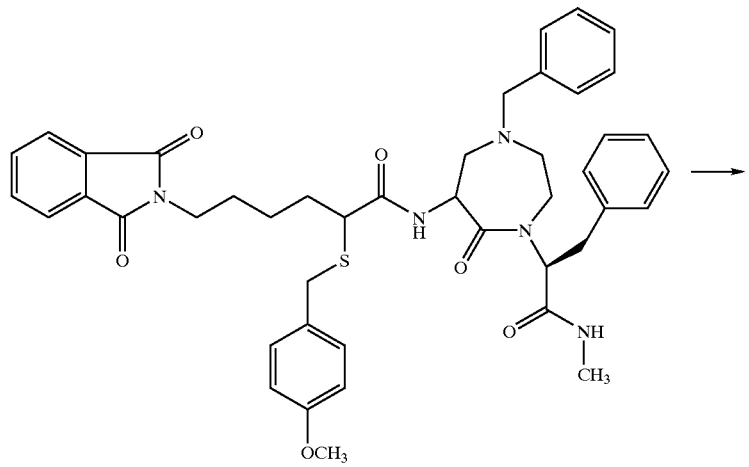

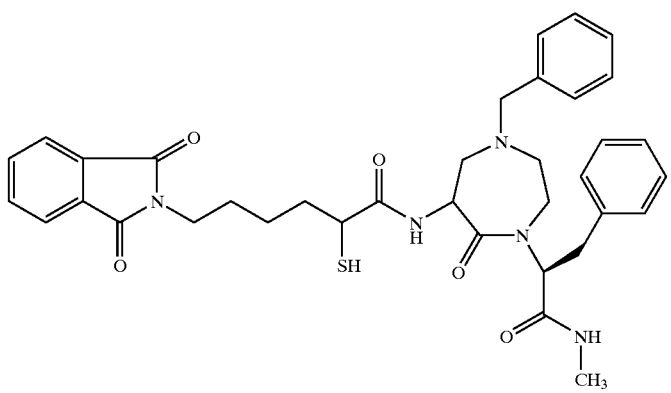

Scheme B, step m; A mixture of α-thioamide of Step 3.11 (326 mg, 0.420 mmol), mercuric acetate (234 mg, 0.734 mmol) and anisole (0.45 mL, 4.2 mmol) in methylene chloride (12 mL) is cooled in an ice bath, degassed (vacuum-$N_2$) and treated with trifluoroacetic acid (5 mL). After 3 h, $H_2S$ gas is bubbled through the reaction mixture for 15 min. The black precipitate is filtered and washed with methylene chloride. The filtrate is concentrated and residual trifluoroacetic acid is removed by coevaporation with carbon tetrachloride. The residue is triturated with hexanes to yield the product mixture as a tan solid (350 mg). This mixture is purified by reverse phase preparative HPLC using 30% $CH_3CN$/water (0.1% tfa) as the eluent to give the desired product (130 mg, 47%).

EXAMPLE 4
Preparation of Compound II-2

Step 4.1

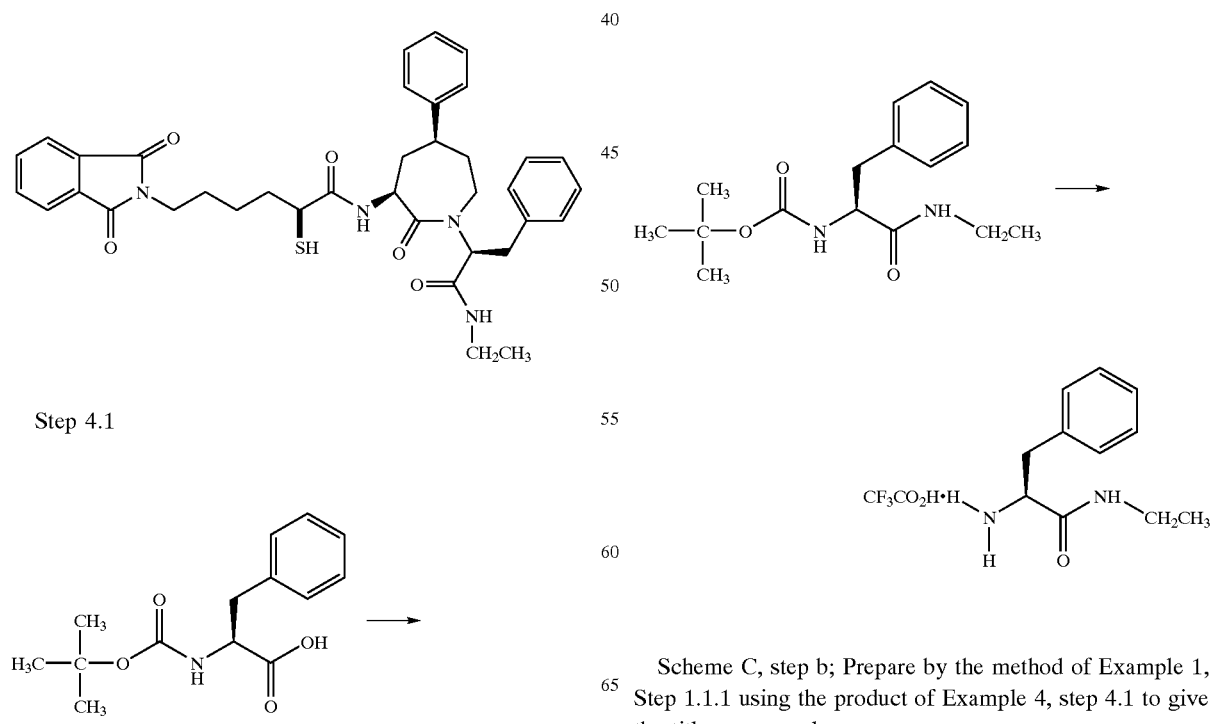

Scheme C, step a; Prepare by the method of Example 1, Step 1.1 using ethylamine to give the title compound.

Step 4.1.1

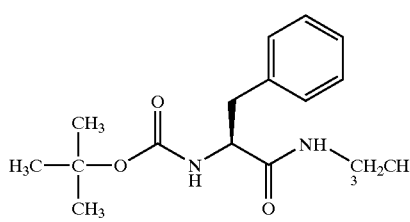

Scheme C, step b; Prepare by the method of Example 1, Step 1.1.1 using the product of Example 4, step 4.1 to give the title compound.

Step 4.2

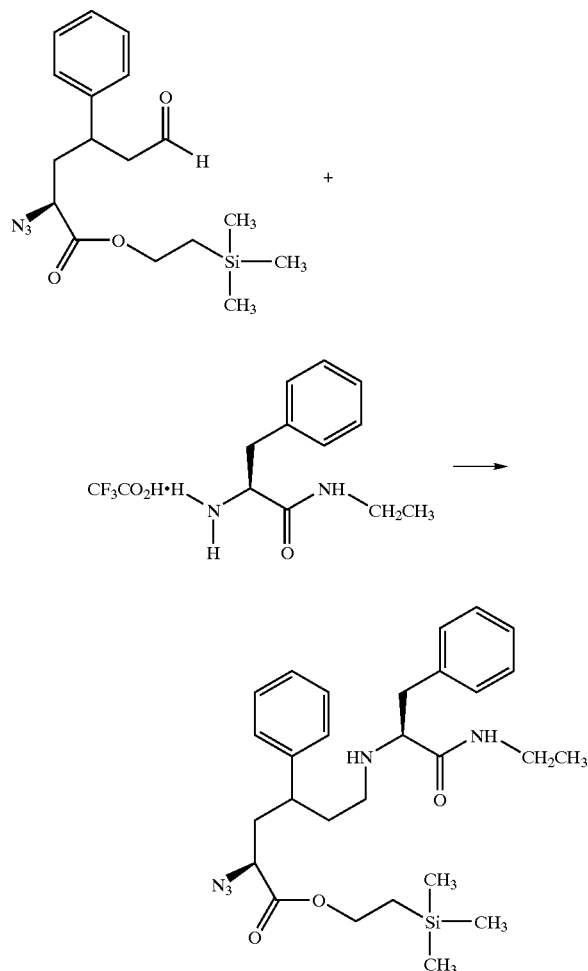

Scheme A, step f; Prepare by the method of Example 1, step 1.3.5 using the product of Example 4, step 4.1.1 to provide the title compound.

Step 4.3

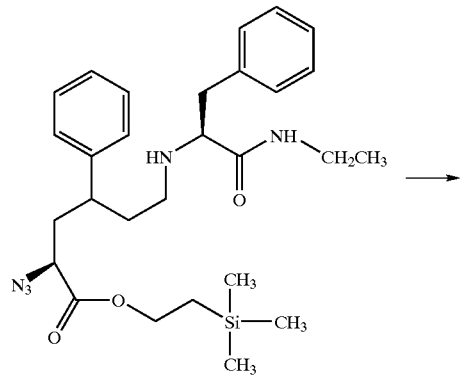

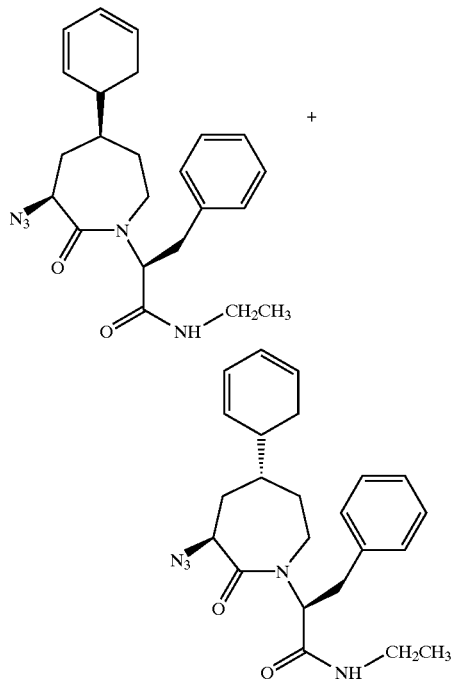

Scheme A, step g; Prepare by the method of Example 1, step 1.3.6 using the product of Example 4, step 4.2 to provide the title cis- and trans-compounds.

Step 4.4

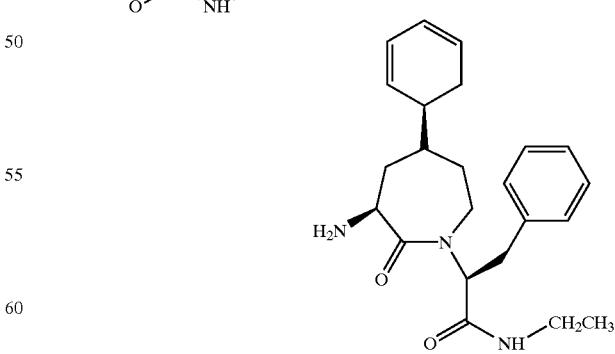

Scheme A, step h1; Prepare by the method of Example 1, step 1.3.7 using the cis-isomer product of Example 4, step 4.3 to provide the title compound.

Step 4.5
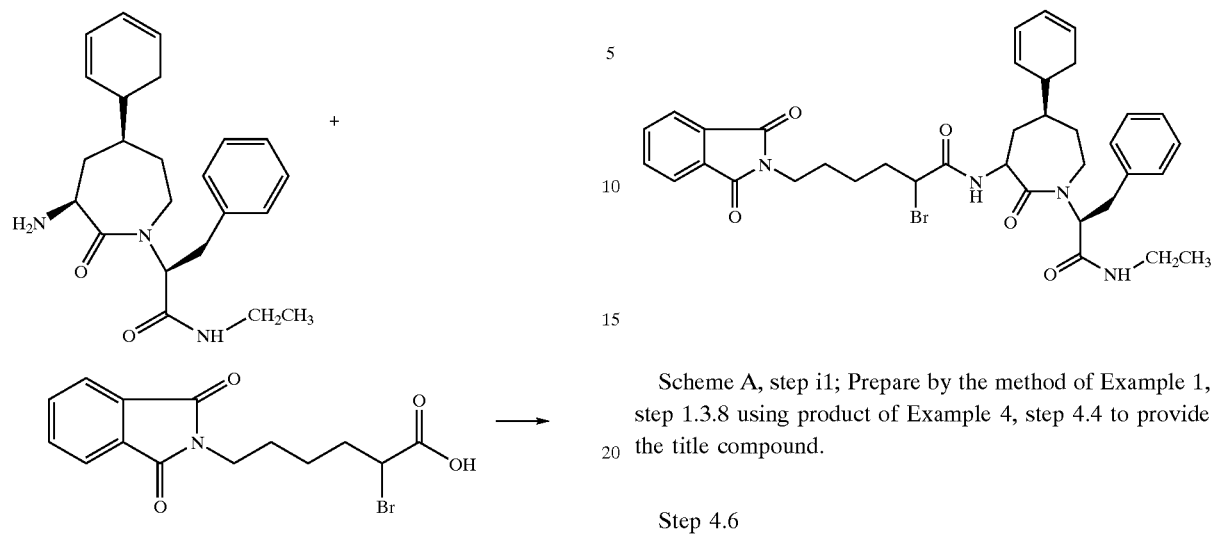
Scheme A, step i1; Prepare by the method of Example 1, step 1.3.8 using product of Example 4, step 4.4 to provide the title compound.
Step 4.6
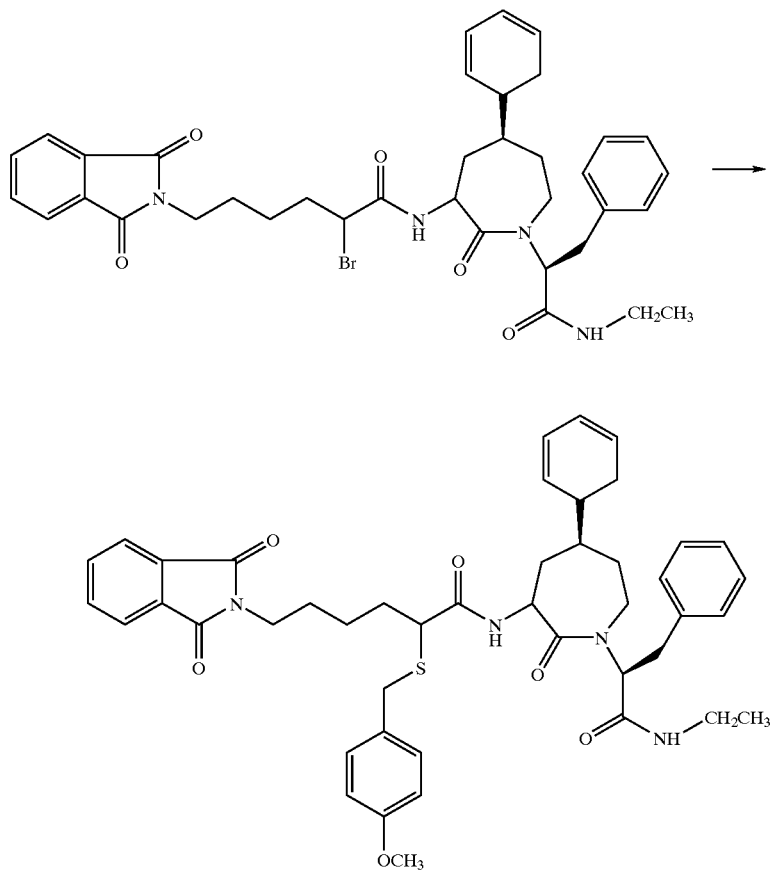

Scheme A, step j1; Prepare by the method of Example 1, step 1.3.9 using product of Example 4, step 4.5 to provide the title compound.

Step 4.7

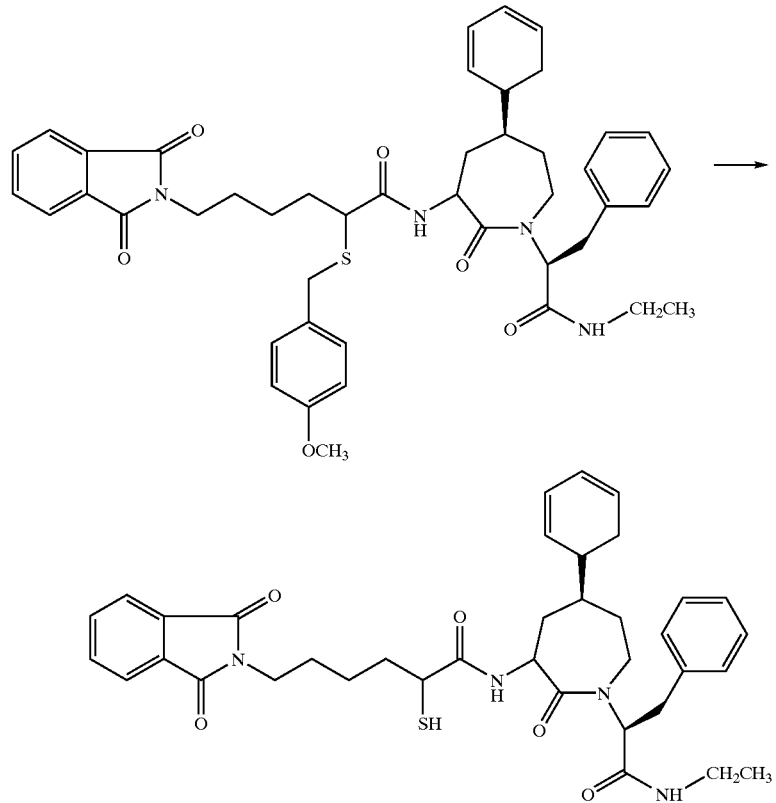

Scheme A, step k1; Prepare by the method of Example 1, step 1.3.10 using product of Example 4, step 4.6 to provide the title compound.

EXAMPLE 5

Preparation of Compound III-9

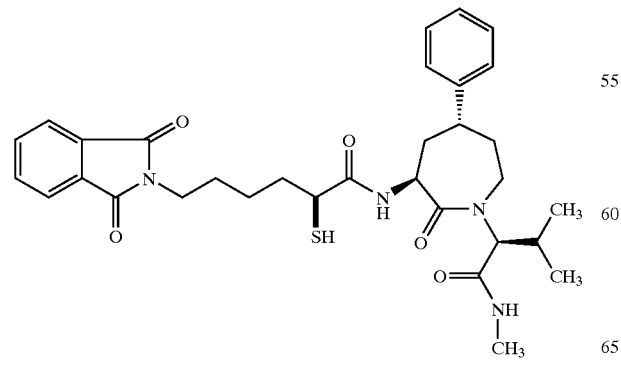

Step 5.1

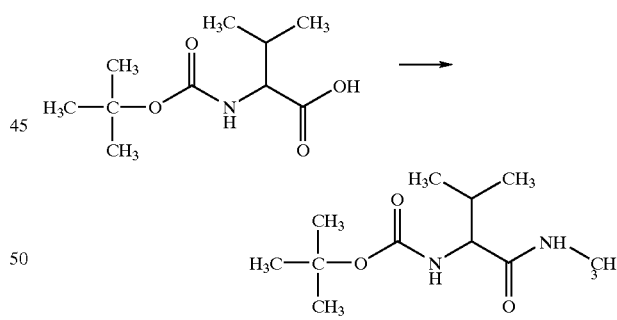

Scheme C, step a; Prepare by the method of Example 1, Step 1.1 using Boc-Val-OH to give the title compound.

Step 5.1.1

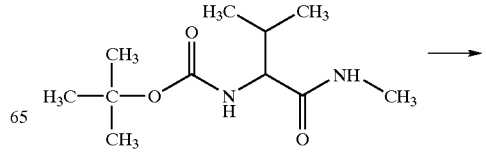

111

-continued

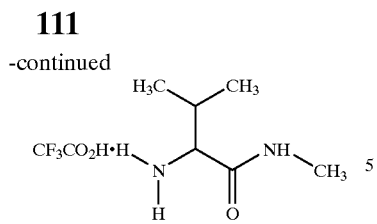

Scheme C, step b; Prepare by the method of Example 1, Step 1.1.1 using the product of Example 5, step 5.1 to give the title compound.

Step 5.2

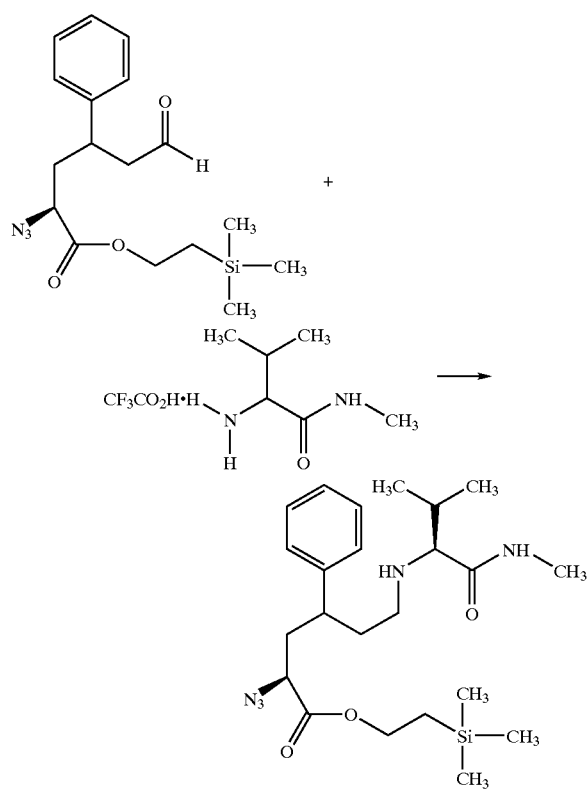

Scheme A, step f; Prepare by the method of Example 1, step 1.3.5 using the product of Example 5, step 5.1.1 to provide the title compound.

Step 5.3

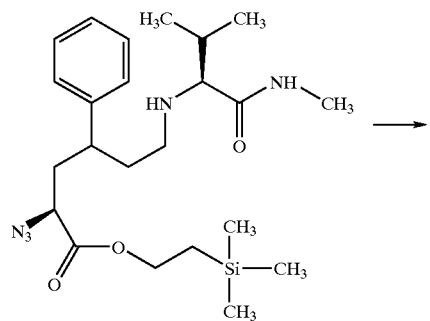

112

-continued

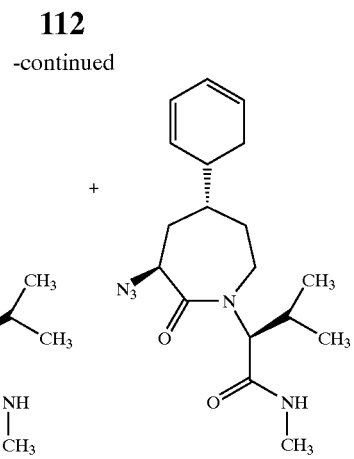

Scheme A, step g; Prepare by the method of Example 1, step 1.3.6 using the product of Example 5, step 5.2 to provide the title cis- and trans-compounds.

Step 5.4

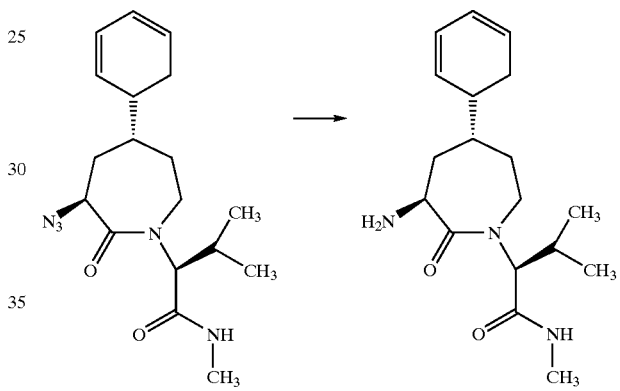

Scheme A, step h1; Prepare by the method of Example 1, step 1.3.7 using the trans-isomer product of Example 5, step 5.3 to provide the titled compound.

Step 5.5

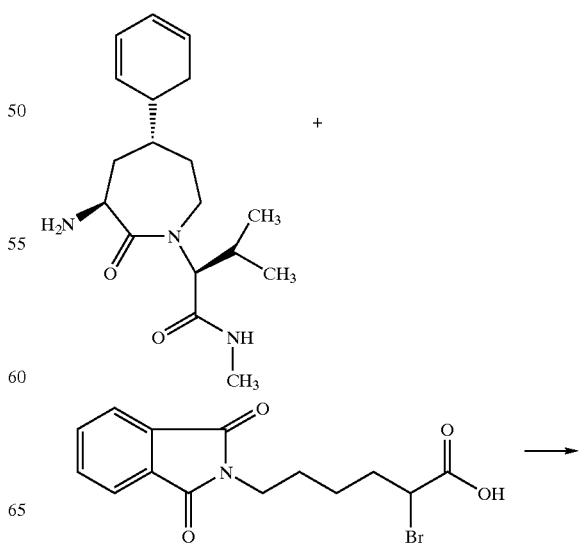

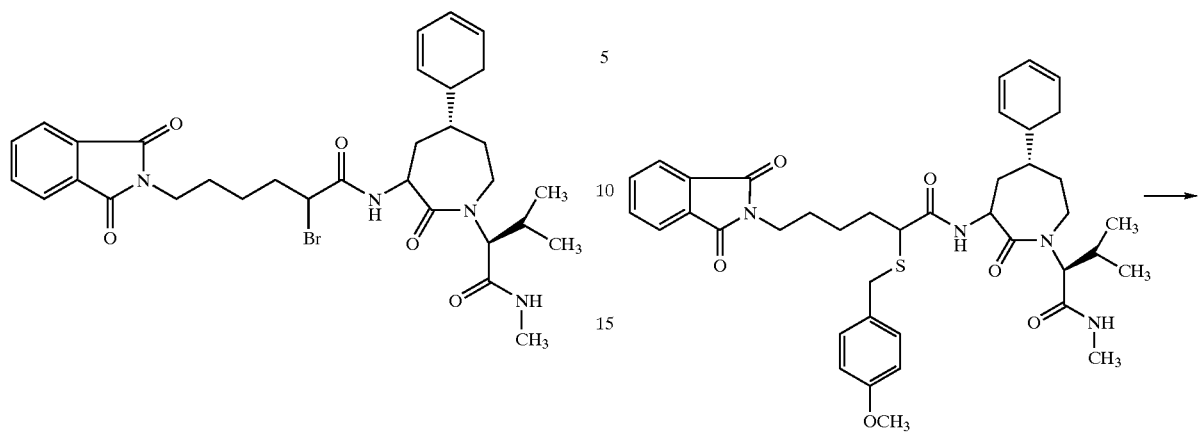

Scheme A, step i1; Prepare by the method of Example 1, step 1.3.8 using product of Example 5, step 5.4 to provide the title compound.

Step 5.6

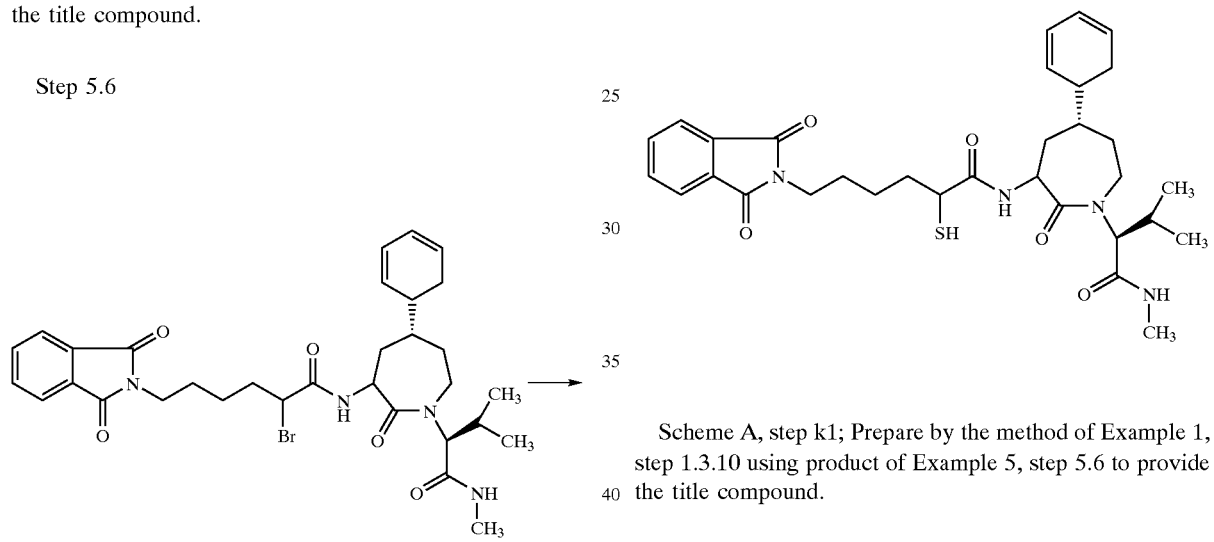

Scheme A, step j1; Prepare by the method of Example 1, step 1.3.9 using product of Example 4, step 4.5 to provide the title compound.

Step 5.7

Scheme A, step k1; Prepare by the method of Example 1, step 1.3.10 using product of Example 5, step 5.6 to provide the title compound.

EXAMPLE 6

Preparation of Compound IV-28

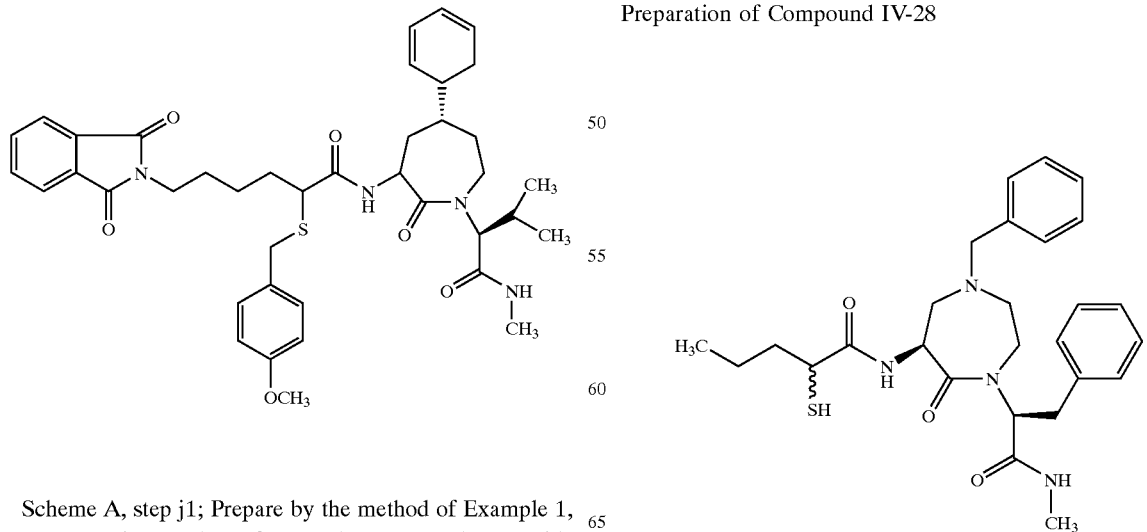

Step 6.1

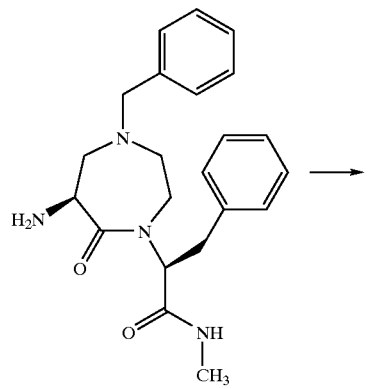

Scheme B, step k; Prepare by the method of Example 3, step 3.10 reacting the amine product of Example 3, step 3.9 with 2-bromopentanoic acid to provide the title compound.

Step 6.2

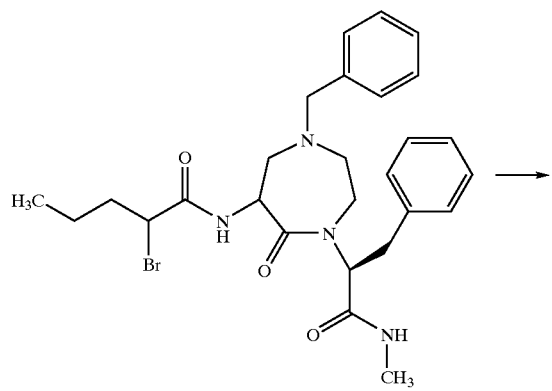

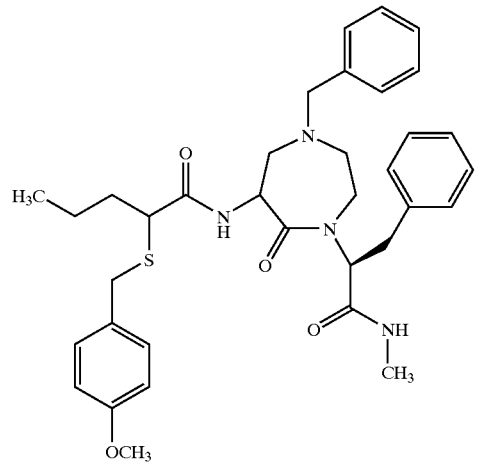

Scheme B, step 1; Prepare by the method of Example 3, step 3.11 using the product of Example 6, step 6.1 to provide the title compound.

Step 6.3

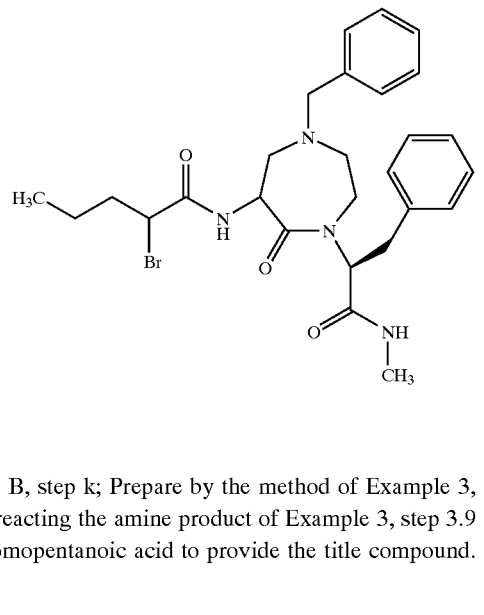

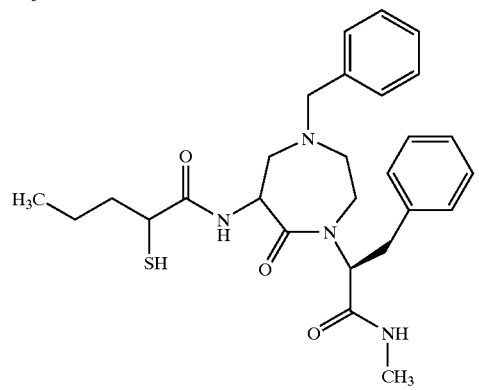

Scheme B, step m; Prepare by the method of Example 3, step 3.12 using the product of Example 6, step 6.2 to provide the title compound.

EXAMPLE 7
Preparation of Compound II-37

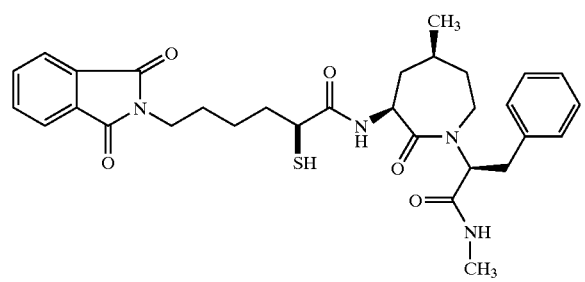

Step 7.1

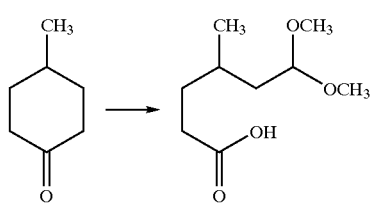

Scheme A, step a; Prepare by the method of Example 1, step 1.3 using 4-methylcyclohexanone to provide the title compound.

Step 7.2

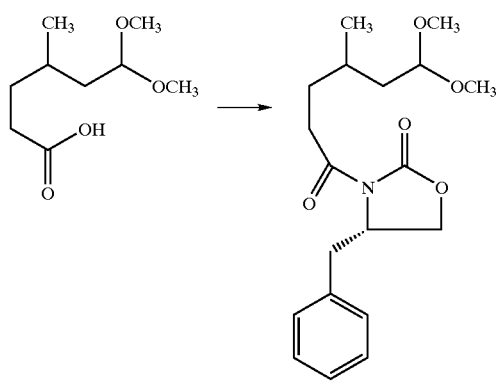

Scheme A, step b; Prepare by the method of Example 1, step 1.3.1 using the product of Example 7, step 7.1 to provide the title compound.

Step 7.3

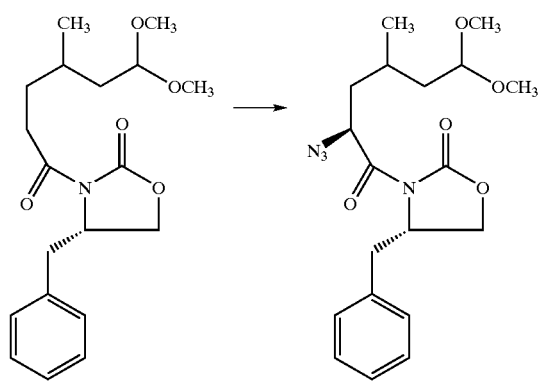

Scheme A, step c; Prepare by the method of Example 1, step 1.3.2 using the product of Example 7, step 7.2 to provide the title compound.

Step 7.4

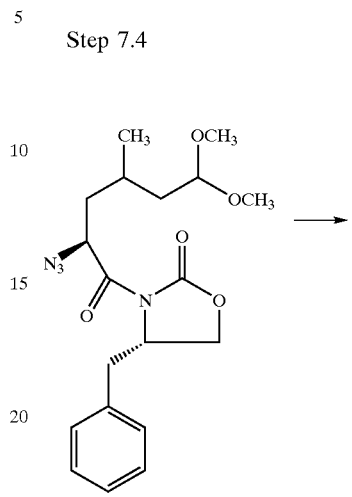

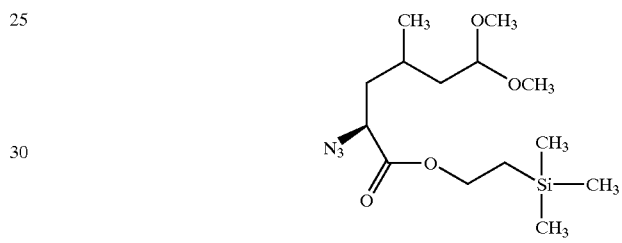

Scheme A, step d; Prepare by the method of Example 1, step 1.3.3 using the product of Example 7, step 7.3 to provide the title compound.

Step 7.5

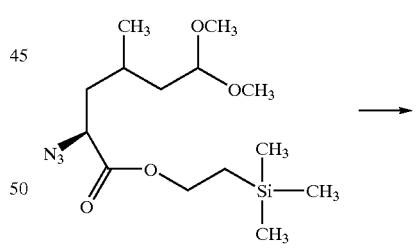

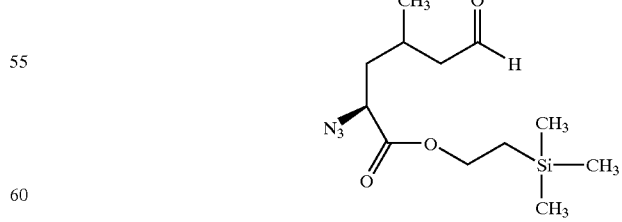

Scheme A, step e; Prepare by the method of Example 1, step 1.3.4 using the product of Example 7, step 7.4 to provide the title compound.

Step 7.6

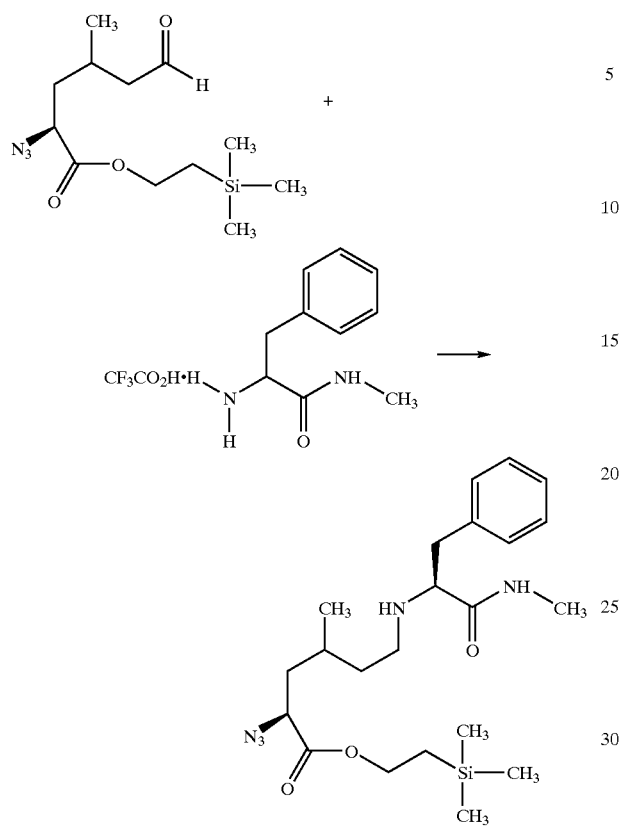

Scheme A, step f, Prepare by the method of Example 1, step 1.3.5 using the product of Example 7, step 7.5 and the amine salt product of Example 1.1.1 to provide the title compound.

Step 7.7

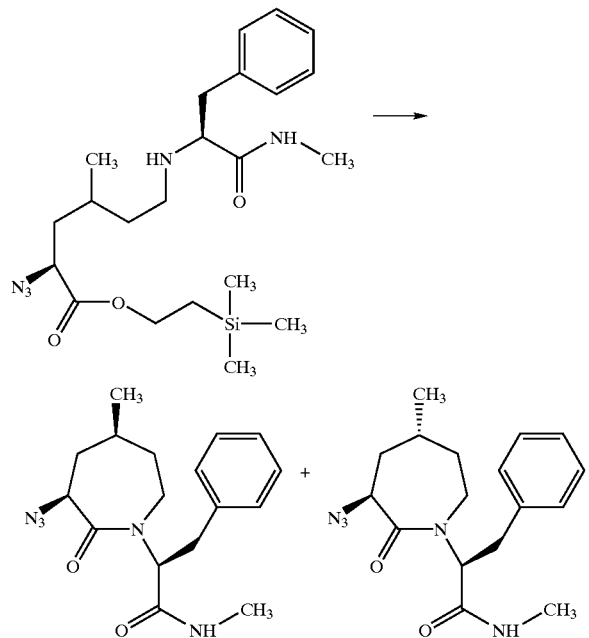

Scheme A, step g; Prepare by the method of Example 1, step 1.3.6 using the product of Example 7, step 7.6 to provide the cis- and trans-isomers of title compound.

Step 7.8

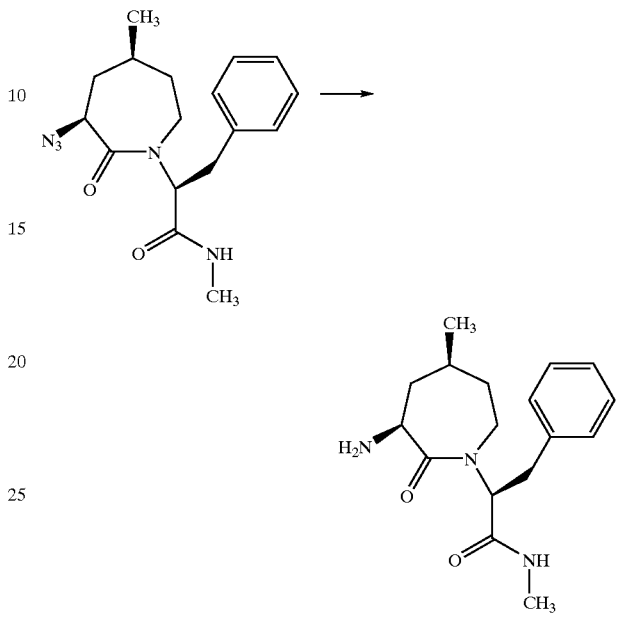

Scheme A, step h1; Prepare by the method of Example 1, step 1.3.7 using the product of Example 7, step 7.7 to provide the title compound.

Step 7.9

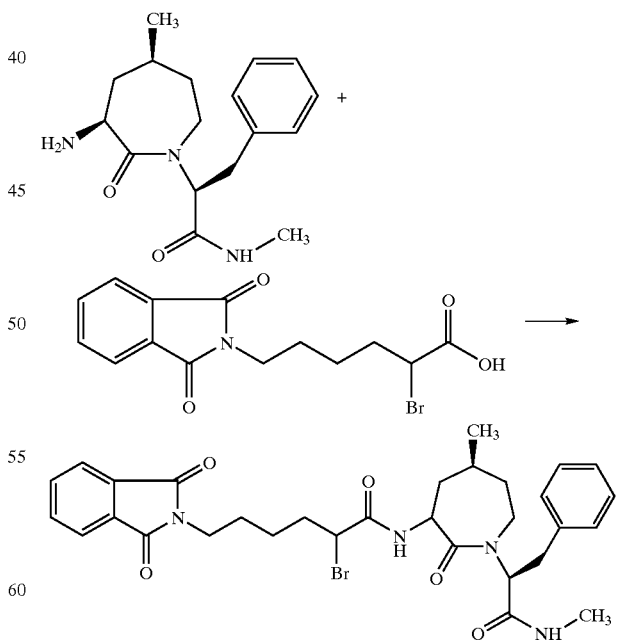

Scheme A, step i1; Prepare by the method of Example 1, step 1.3.8 using the product of Example 7, step 7.8 to provide the title compound.

Step 7.10
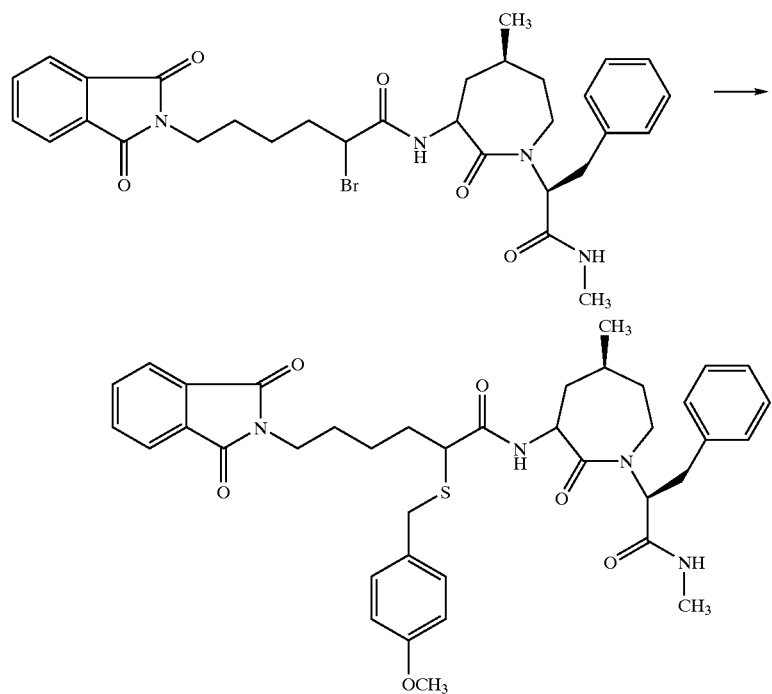
Scheme A, step j1; Prepare by the method of Example 1, step 1.3.9 using the product of Example 7, step 7.9 to provide the title compound.
Step 7.11
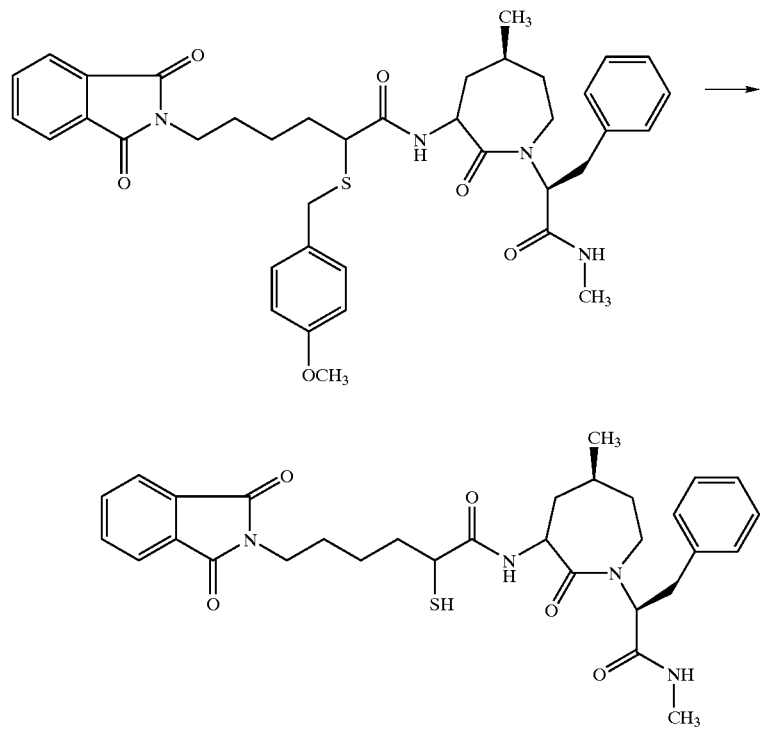

Scheme A, step k1; Prepare by the method of Example 1, step 1.3.10 using the product of Example 7, step 7.10 to provide the title compound.

In a further embodiment, the present invention provides a method of inhibiting matrix metalloproteinase (MMP) to a patient in need thereof comprising administering to the patient an effective matrix metalloproteinase inhibiting amount of a compound of formula (1).

As used herein, the term "patient" refers to warm-blooded animals or mammals, including guinea pigs, dogs, cats, rats, mice, hamsters, rabbits and primates, including humans. A patient is in need of treatment to inhibit MMP when it would be beneficial to the patient to reduce the physiological effect of active MMP. For example, a patient is in need of treatment to inhibit MMP when a patient is suffering from a disease state characterized by excessive tissue disruption or tissue degradation, such as, but not limited to, a neoplastic disease state or cancer, rheumatoid arthritis; osteoarthritis; chronic inflammatory disorders, such as emphysema or chronic bronchitis; cardiovascular disorders, such as atherosclerosis; corneal ulceration; dental diseases, such as gingivitis or periodontal disease; and neurological disorders, such as multiple sclerosis.

The identification of those patients who are in need of treatment to inhibit MMP is well within the ability and knowledge of one skilled in the art. A clinician skilled in the art can readily identify, by the use of clinical tests, physical examination and medical/family history, those patients who are suffering from disease states characterized by excessive tissue disruption or tissue degradation.

An "effective matrix metalloproteinase inhibiting amount" of a compound of formula (1) is an amount which is effective, upon single or multiple dose administration to the patient, in providing relief of symptoms associated with MMP and is thus effective in inhibiting MMP-induced tissue disruption and/or MMP-induced tissue degradation. As used herein, "relief of symptoms" of MMP-mediated conditions refers to decrease in severity over that expected in the absence of treatment and does not necessarily indicate a total elimination or cure of the disease. Relief of symptoms is also intended to include prophylaxis.

An effective matrix metalloproteinase inhibiting dose can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

An effective matrix metalloproteinase inhibiting amount of a compound of formula (1) will generally vary from about 0.1 milligram per kilogram of body weight per day (mg/kg/day) to about 300 milligrams per kilogram of body weight per day (mg/kg/day). A daily dose of from about 1 mg/kg to about 100 mg/kg is preferred.

The term "neoplastic disease state" as used herein refers to an abnormal state or condition characterized by rapidly proliferating cell growth or neoplasm. Neoplastic disease states for which treatment with a compound of formula (1) will be particularly useful include: Leukemias, such as, but not limited to, acute lymphoblastic, chronic lymphocytic, acute myeloblastic and chronic myelocytic; Carcinomas and adenocarcinomas, such as, but not limited to, those of the cervix, oesophagus, stomach, small intestines, colon, lungs (both small and large cell), breast and prostate; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, follicullar reticulum, cell sarcoma and Hodgkin's Disease. Neoplastic disease states for which treatment with a compound of formula (1) will be particularly preferred include carcinomas and adenocarcinomas, particularly of the breast, prostate and lung.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

The term "chronic inflammatory disease" refers to diseases or conditions characterized by persistent inflammation in the absence of an identifiable irritant or microbial pathogen.

Inflammatory diseases for which treatment with a compound of formula (1) will be particularly useful include: emphysema, chronic bronchitis, asthma, chronic obstructive pulmonary disorder and chronic inflammation.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, topically, intranasally, rectally, and the like. Oral administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, gels, ointments, aerosol or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as to colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (1): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

EXAMPLE 8

Method for Characterization of MMP Inhibitors

A. Source and Activation of proMMP-3

ProMMP-3 (EC 3.4.24.17; Stromelysin-1) was purified from culture medium of human rheumatoid synovial fibroblasts stimulated with macrophage-conditioned medium according to Okada, Y. et al., *J. Biol. Chem.* 261, 14245–14255 (1986). The active MMP-3 was obtained by treatment of proMMP-3 with trypsin (51 g/mL) at 37° C. for 30 min. followed by addition of soybean trypsin inhibitor (50 μg/mL). Aliquots of the activated MMP-3 were stored at −20° C.

B. Determination of Inhibition Constant ($K_i$) for MMP-3

The activated MMP-3 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in an assay buffer containing 50 mM Tris, pH 7.6, 0.2 M NaCL, 50 mM CaCl$_2$, and 0.02% Brij-35. The increase in fluorescence due to cleavage of Gly-Leu peptide bond by MMP-3 was monitored with Perkin-Elmer LS50B Fluorimeter ($\lambda_{ex}$328 nm, $\lambda_{em}$393 nm, excitation slit 2.5, emission slit 10). Substrate and inhibitor stock solutions were made in DMF and 0.1% HCl-DMF, respectively. For determination of $K_i$ values for MMP-3 inhibitors, a series of intermediate inhibitor solutions were prepared in 0.1% HCl-DMF and 1 or 2 μL of the diluted inhibitor solution was mixed with 1 μL of 2 mM substrate solution in DMF in a quartz cuvette containing 2 mL of assay buffer. The enzyme (10 μL of 0.2 μM MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 μM (<<Km) and [MMP-3]=1 nM. Under these conditions, the measured $K_{i,app}$ is close to true $K_i$.

C. Source and Activation of proMMP-2

Recombinant MMP-2 was purified from the fermentation broth of yeast *Pichia pastoris* that carries the integrated MMP-2 gene into its chromosome. In brief, the full-length cDNA for MMP-2 was obtained by reverse transcription of RNA from human melanoma A375M cell line by the reverse transcriptase polymerase chain reaction (RT-PCR) using sequence specific oligonucleotides. The nucleotide sequence was confirmed by Taq cycle sequencing. The cDNA was ligated into the *Pichia pastoris* expression vector pHIL-D2 in such a way that the expression of pro-MMP2 is under the control of the methano inducible alcohol oxidase promoter. The expression construct was digested with either SalI or NsiI and used to transform the *Pichia pastoris* strains KM71 and SMD1168. A large-scale culture of a selected clone designated 24S was performed in a high cell density fermentor and the recombinant MMP-2 was purified from the culture supernatant by gelatin-sepharose 4B (Pharmacia). The enzyme is sufficiently pure at this stage for routine measurement of inhibition. If desired, however, the enzyme may be further purified by AcA 44 gel filtration (Spectra).

D. Determination of Inhibition Constant ($K_i$) for MMP-2

The active MMP-2 was obtained by activation of proMMP-2 at 37° C. for 1 h with 4-aminophenylmercuric acetate which was then removed by a Sephadex G-50 spin column. The enzyme is assayed using a fluorogenic substrate, Mca-Pro-Leu-Gly-Leu-Dpa-Ala-Arg-NH$_2$, at 37° C. in 2.0 mL of assay buffer containing 50 mM Tris, pH 7.6, 0.2 M NaCl, 50 mM CaCl$_2$, 0.02% Brij-35, and 50 μM β-mercaptoethanol. The increase in fluorescence is monitored ($\lambda_{ex}$ 328 nm, $\lambda_{em}$ 393 nm). Substrate and inhibitor stock solutions are made in DMF. The enzyme is added at the last to start the reaction. For routine measurement of a $K_i$ value for a reversible, competitive inhibitor, the initial rates in the presence of at least four inhibitor concentrations (two inhibitor concentrations above $K_i$ and two below $K_i$) are measured using [S]=1 μM (<<Km) and [MMP-2]=0.4 nM. Under these conditions, the measured $K_i$, app is close to true $K_i$.

E. Source of MMP-12 (macrophage metalloelastase)

MMP-12 (EC 3.4.24.65) was cloned, expressed and purified according to Shapiro, S. D. et al., *J. Biol. Chem.* 268, 23824–23829 (1993). Autoactivation resulted in the fully processed active form of the enzyme. Aliquots of MMP-12 were stored at −70C.

F. Determination of the Inhibition Constant (Ki) for MMP-12.

The potency of inhibitors of MMP-12 was measured using either quartz cuvettes or microtiter plates. The activity of MMP-12 was measured using a fluorogenic substrate, Mca-Pro-Leu-Gly-Leu-Dpa-Ala-Arg-NH2, Knight, C. G. et al., *FEBS Lett.* 296,263–266 (1992), at 25C. in an assay buffer containing 50 mM Tris, pH 7.6, 0.2 M NaCl, 50 mM $CaCl_2$, and 0.02% Brij-35. The increase in fluorescence due to cleavage of Gly-Leu peptide bond by MMP-12 was monitored with a Perkin-Elmer LS50B Fluorimeter ($\lambda_{ex}$ 328 nm, $\lambda_{em}$ 393 nm, excitation slit 2.5, emission slit 10) for the cuvette assay and with a Molecular Devices Fmax fluorescence plate reader ($\lambda_{ex}$ 320 nm, $\lambda_{em}$ 405 nm) for the microtiter plate assay. Substrate and inhibitor stock solutions were made in N,N,dimethylformamide (DMF) and 0.1% HCl-DMF, respectively.

Ki values were determined using the cuvette method by preparing a series of intermediate inhibitors solutions in 0.1% HCl-DMF and mixing the inhibitor with substrate (final concentration 2 $\mu$M) in a quartz cuvette containing 2 ml of assay buffer. MMP-12 was added to start the reaction at a concentration of 2 nM and progress curves were generated. For routine measurement of a Ki value for a reversible competitive inhibitor, the initial rates in the presence of at least four inhibitor concentrations (two concentrations above and two concentrations below the Ki) were measured [S]=2 $\mu$M (<<Km) and [MMP-12]=2 $\mu$M.

Under these conditions, the measured Ki,app is close to the true Ki.

Ki values were determined using the microtiter plate method in a manner similar to that described for the cuvette method with some modifications. Four different inhibitor concentrations (50 $\mu$l in assay buffer)of each compound were added to separate wells of a microtiter plate and substrate was added (100 $\mu$l) to get a final concetration of 4 $\mu$M. MMP-12 was added to a final concentration of 2 nM (50 $\mu$l) to start the reaction. Cleavage of substrate was recorded every 30 seconds for 30 minutes and progress curves were generated.

G. Calculation of $K_i$ Values

The $K_i$ for a competitive inhibitor is calculated using: $v_0/v_i=(1+[I]/K_{i,app})$ and $K_i=K_{i,app}/(1+[S]/K_M)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

TABLE 4

| Compound | MMP-2 (Ki, nm) | MMP-3 (Ki, nm) | MMP-12 (Ki, nm) |
|---|---|---|---|
| II-1 | 1.2 | 39 | 18 |
| III-1 | N.T.* | 73 | 53 |
| IV-1 | N.T. | 210 | N.T. |

*N.T. = not tested

The compounds of formula (1) can be tested by any appropriate model for in vivo drug absorption. The in vivo absorption of a compound of formula (1) can be confirmed using an in situ rat intestinal technique as described by Blanchard, J. et al., *Journal of Pharmaceutical Sciences,* 79, 411–414 (1990). In this technique, the absorption of a compound of formula (1) is evaluated using this in situ rat intestinal perfusion technique in which the disappearance from the intestinal lumen, binding to the perfused jejunal segment, and appearance in the mesenteric (jejunal) vein are measured.

Likewise, the ability of compounds of formula (1) to inhibit matrix metalloproteinase in vivo can be tested by any appropriate model for in vivo inhibition of matrix metalloproteinase. The in vivo inhibition of matrix metalloproteinase, as well as the anti-tumoral effects of the compounds of formula (1), can be confirmed using a technique described by Davies, B. et al., *Cancer Research* 53, 2087–2091 (1993) where human ovarian xenografts are grown in nude mice. Inhibition of the enzyme is demonstrated by the transition of ascites to solid tumors, concomitantly slowing tumor cell growth and allowing development of tumor stroma.

Similarly, the in vivo inhibition of matrix metalloproteinase by the compounds of formula (1) can be determined by injecting activated matrix metalloproteinase along with proteoglycan monomer (Lark, M. W. et al., *Biochem Pharmacol.* 39, 2041–2049 (1990)) or $^3$H carboxymethyl transferrin (Chapman, K. T. et al, *Bioorg. Med. Chem. Lett.* 6, 803–806 (1996)) into the pleural cavity of mice or rats and measuring substrate degradation in the pleural fluid. The in vivo inhibition of cartilage degradation can be demonstrated using the adjuvant induced arthritis model (Conway, J. G. et al., *J. Exp. Med.* 182, 449–457) or any of a number of animal models of arthritis.

What is claimed is:
1. A compound of the formula

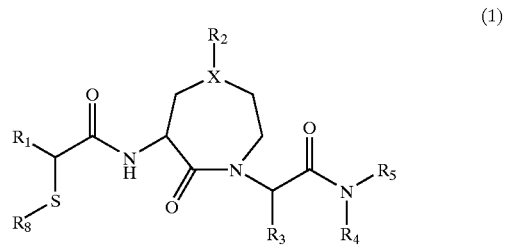

(1)

wherein $R_1$ is $C_1$–$C_6$ alkyl, a W—$(CH_2)_m$— group, or a Q—Z—$(CH_2)_m$— group wherein W is phthalimido; Z is a bond or is oxy, $NR_6$, $C(O)NR_6$, $NR_6C(O)$, $NHC(O)NR_6$, $OC(O)NR_6$, $HNC(O)O$, or $SO_2NR_6$; Q is hydrogen, or a Y—$(CH_2)_n$— group wherein Y is hydrogen, $C_6$–$C_{10}$ aryl, a cyclic or bicyclic, aromatic assemblage of three to nine carbon atoms and from 1 to 3 nitrogen, oxygen, or sulfur atoms, —$C(O)OR_6$, —$N(R_6)_2$, morpholino, piperidino, pyrrolidino, or isoindolyl;

$R_2$ is $C_1$–$C_4$ alkyl, a —$(CH_2)_p$—$(C_3$–$C_9)$heteroaryl group, or a —$(CH_2)_p$—$Ar_1$ group wherein $Ar_1$ is phenyl or naphthyl optionally substituted with a substituent selected from the group consisting of halogen, $C_1$–$C_4$ alkyl, —$OR_7$, —$N(R_6)_2$, $SO_2N(R_6)$ or —$NO_2$;

$R_3$ is hydrogen, $C_1$–$C_6$ alkyl, —$CH_2SCH_2NHCOCH_3$, a —$(CH_2)_p$—A group, a —$(CH_2)_m$—B group or a —$CH_2$—D—$R_7$ group wherein A is $C_6$–$C_{10}$ aryl, $C_3$–$C_9$ heteroaryl, or cyclohexyl; B is —$N(R_7)_2$, guanidino, nitroguanidino, —$C(O)OR_6$ or —$C(O)NR_6$; and D is oxy or thio;

$R_4$ is hydrogen or a —$(CH_2)_m$—$S(O)_pX'(R_6)_2$ group;

$R_5$ is hydrogen, $C_1$–$C_6$ alkyl or $R_4$ and $R_5$ taken together with the nitrogen atom to which they are attached form piperidino, pyrrolidino, or isoindolyl;

$R_6$ is hydrogen or $C_1$–$C_6$ alkyl;

$R_7$ is hydrogen, $C_1$–$C_4$ alkyl, or a —$(CH_2)_p$—$Ar_2$ group wherein $Ar_2$ is phenyl or naphthyl optionally substituted with a substituent selected from the group consisting of halogen, $C_1$–$C_4$ alkyl, —$OR_7$, —$N(R_6)_2$, $SO_2N(R_6)_2$ or —$NO_2$;

$R_8$ is hydrogen, —C(O)$R_7$, a —C(O)—(CH$_2$)$_q$—K group or a —S—G group, wherein K is selected from the group consisting of

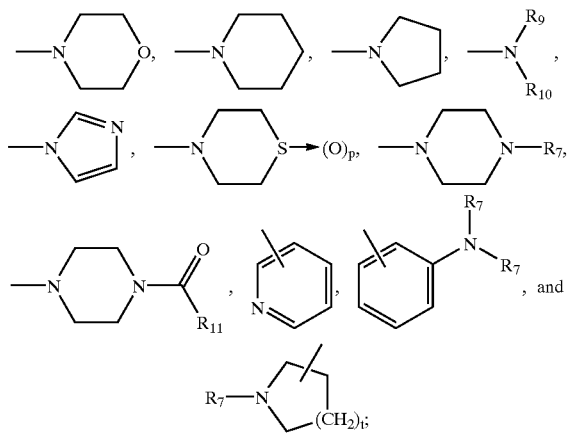

G is selected from the group consisting of

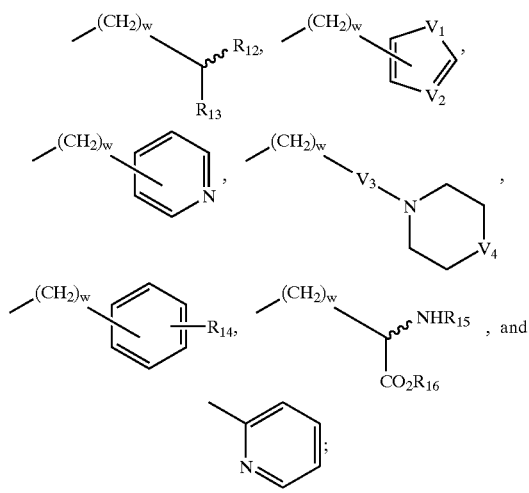

$R_9$ and $R_{10}$ are each independently C$_1$–C$_4$ alkyl or a —(CH$_2$)$_p$—Ar$_2$ group;

$R_{11}$ is —CF$_3$, C$_1$–C$_{10}$ alkyl or a —(CH$_2$)$_p$—Ar$_2$ group;

$R_{12}$ is hydrogen, C$_1$–C$_6$ alkyl, —CH$_2$CH$_2$S(O)$_n$CH$_3$, or arylalkyl;

$R_{13}$ is hydrogen, hydroxy, amino, C$_1$–C$_6$ alkyl, N-methylamino, N,N-dimethylamino,
 —CO$_2$R$_{17}$ or —OC(O)R$_{18}$ wherein R$_{17}$ is hydrogen, —CH$_2$O—C(O)C(CH$_3$)$_3$, C$_1$–C$_4$ alkyl, a —(CH$_2$)$_p$—Ar$_2$ group or diphenylmethyl and R$_{18}$ is hydrogen, C$_1$–C$_6$ alkyl or phenyl;

$R_{14}$ is 1 or 2 substituents independently chosen from the group consisting of hydrogen, C$_1$–C$_4$ alkyl, C$_1$–C$_4$ alkoxy, or halogen;

$R_{15}$ is hydrogen, C$_1$–C$_6$ alkyl or a —(CH$_2$)$_p$—Ar$_2$ group;

$R_{16}$ is hydrogen or C$_1$–C$_4$ alkyl;

$V_1$ is O, S, or NH;

$V_2$ is N or CH;

$V_3$ is a bond or —C(O)—;

$V_4$ is —(CH$_2$)$_{w'''}$, O, S, NR$_7$, or NC(O)R$_{11}$;

X and X' are each independently CH or N;

m is an integer 2–4;
n is zero or an integer 1–4;
p is zero or an integer 1–2;
q is zero or an integer 1–5;
t is an integer 1–2;
w is an integer 1–3; and
w' is zero or an integer 1; or
a pharmaceutically acceptable salt, stereoisomer or hydrate thereof.

2. A compound of claim 1 wherein X is CH.

3. A compound of claim 2 wherein $R_2$ is C$_1$–C$_4$ alkyl or a —(CH$_2$)$_p$—Ar group wherein Ar is phenyl optionally substituted with F, Cl, C$_1$–C$_4$ alkyl, —NO$_2$, —NHz or —OR$_7$; and $R_4$ is hydrogen.

4. A compound of claim 3 wherein $R_3$ is hydrogen, C$_1$–C$_6$ alky, phenyl, benzyl, 1-naphthyl, 2-naphthyl, cyclohexylmethyl, 2-hydroxyphenyl, 3-hydroxyphenyl, 4-hyroxyphenyl, 2,3-dihydroxyphenyl, 2,4-dihydroxyphenyl, 3,4-dihydroxyphenyl, 4-methoxyphenyl, 4-ethoxyphenyl, 2-chlorophenyl, 3-chlorophenyl, 4-chlorophenyl, 3,4-dichlorophenyl, 4-bromophenyl, 3,4-dibromophenyl, 4-fluorophenyl, 3,4-difluorophenyl, 3-tolyl, 4-tolyl, 4-ethylphenyl, 4-isopropylphenyl, 3-aminophenyl, 4-aminophenyl, 3,4-diaminophenyl, N-methyl-4-aminophenyl, 2-nitrophenyl, 4-nitrophenyl, 4-aminobenzyl, 4-hydroxybenzyl, 4-methoxybenzyl, 3-chlorobenzyl, 4-fluorobenzyl, 3,4-dichlorobenzyl, 4-bromobenzyl, 4-methylbenzyl, or is a compound of the formula

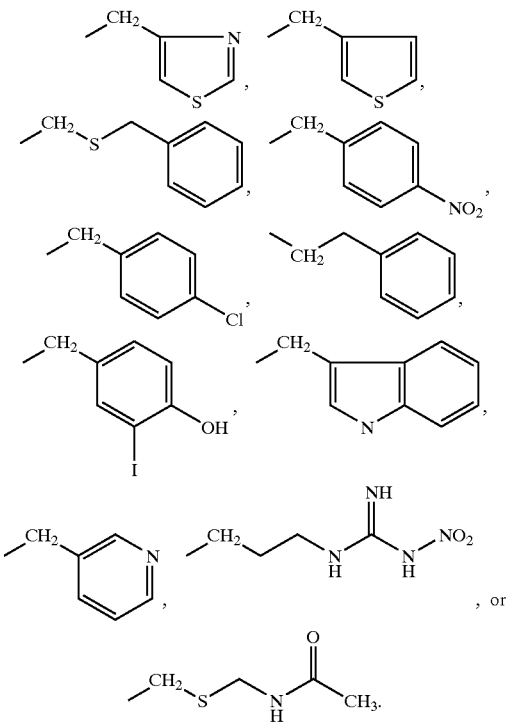

5. A compound of claim 4 wherein $R_5$ is hydrogen, methyl, ethyl, propyl, isopropyl, butyl or isobutyl and $R_8$ is hydrogen.

6. A compound of claim 2 wherein $R_1$ is a W—(CH$_2$)$_m$— group.

7. A compound of claim 3 wherein $R_1$ is a W—(CH$_2$)$_m$— group.

8. A compound of claim 5 wherein $R_1$ is a W—(CH$_2$)$_m$— group.

9. A compound of claim 2 wherein $R_1$ is $C_1$–$C_6$ alkyl.
10. A compound of claim 3 wherein $R_1$ is $C_1$–$C_6$ alkyl.
11. A compound of claim 5 wherein $R_1$ is a $C_1$–$C_6$ alkyl.
12. A compound of claim 2 wherein $R_1$ is a Q—Z—$(H_2)_m$— group.
13. A compound of claim 3 wherein $R_1$ is a Q—Z—$(H_2)_m$— group.
14. A compound of claim 5 wherein $R_1$ is a Q—Z—$(H_2)_m$— group.
15. A compound of claim 1 wherein X is N.
16. A compound of claim 15 wherein $R_2$ is $C_1$–$C_4$ alkyl or a —$(CH_2)_p$—Ar group wherein Ar is phenyl optionally substituted with F, Cl, $C_1$–$C_4$ alkyl, —$NO_2$, —$NH_2$ or —$OR_8$; and $R_4$ is hydrogen.
17. A compound of claim 16 wherein $R_3$ is hydrogen, $C_1$–$C_6$ alkyl, phenyl, benzyl, 1-naphthyl, 2-naphthyl, cyclohexylmethyl, 2-hydroxyphenyl, 3-hydroxyphenyl, 4-hyroxyphenyl, 2,3-dihydroxyphenyl, 2,4-dihydroxyphenyl, 3,4-dihydroxyphenyl, 4-methoxyphenyl, 4-ethoxyphenyl, 2-chlorophenyl, 3-chlorophenyl, 4-chlorophenyl, 3,4-dichlorophenyl, 4-bromophenyl, 3,4-dibromophenyl, 4-fluorophenyl, 3,4-difluorophenyl, 3-tolyl, 4-tolyl, 4-ethylphenyl, 4-isopropylphenyl, 3-aminophenyl, 4-aminophenyl, 3,4-diaminophenyl, N-methyl-4-aminophenyl, 2-nitrophenyl, 4-nitrophenyl, 4-aminobenzyl, 4-hydroxybenzyl, 4-methoxybenzyl, 3-chlorobenzyl, 4-fluorobenzyl, 3,4-dichlorobenzyl, 4-bromobenzyl, 4-methylbenzyl, or is a compound of the formula

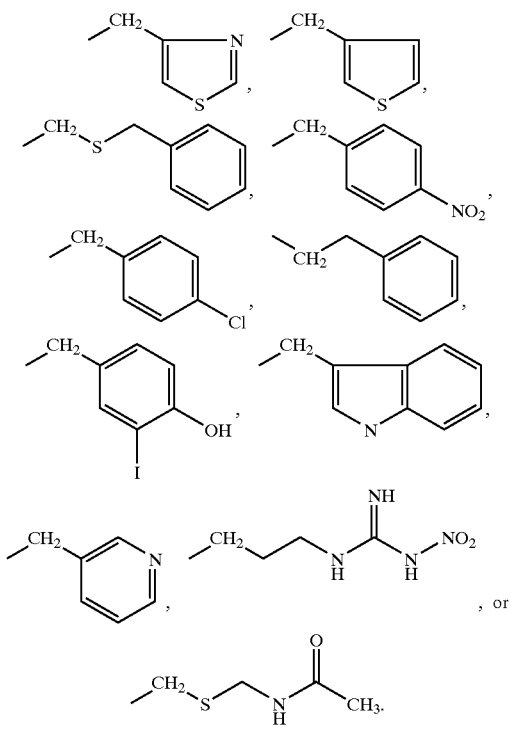

18. A compound of claim 17 wherein $R_5$ is hydrogen, methyl, ethyl, propyl, isopropyl, butyl or isobutyl and $R_8$ is hydrogen.
19. A compound of claim 16 wherein $R_1$ is a W—$(CH_2)_m$— group.
20. A compound of claim 17 wherein $R_1$ is a W—$(CH_2)_m$— group.
21. A compound of claim 19 wherein $R_1$ is a W—$(CH_2)_m$— group.
22. A compound of claim 16 wherein $R_1$ is $C_1$–$C_6$ alkyl.
23. A compound of claim 17 wherein $R_1$ is $C_1$–$C_6$ alkyl.
24. A compound of claim 19 wherein $R_1$ is a $C_1$–$C_6$ alkyl.

25. A compound of claim 16 wherein $R_1$ is a Q—Z—$(H_2)_m$— group.
26. A compound of claim 17 wherein $R_1$ is a Q—Z—$(H_2)_m$— group.
27. A compound of claim 19 wherein $R_1$ is a Q—Z—$(H_2)_m$— group.
28. A compound of claim 1 wherein X is CH; $R_2$ is phenyl, methyl or ethyl; $R_3$ is phenyl, benzyl, cyclohexylmethyl, isopropyl, isobutyl, 3-pyridylmethyl, 4-fluorobenzyl or 4-aminobenzyl; $R_4$ is hydrogen; $R_5$ is hydrogen, methyl, ethyl, propyl, isopropyl, butyl or isobutyl and $R_8$ is hydrogen.
29. A compound of claim 28 wherein $R_1$ is a W—$(CH_2)_m$— group.
30. A compound of claim 1 wherein X is N; $R_2$ is phenyl, methyl or ethyl; $R_3$ is phenyl, benzyl, cyclohexylmethyl, isopropyl, isobutyl, 3-pyridylmethyl, 4-fluorobenzyl or 4-aminobenzyl; $R_4$ is hydrogen; $R_5$ is hydrogen, methyl, ethyl, propyl, isopropyl, butyl or isobutyl and $R_8$ is hydrogen.
31. A compound of claim 30 wherein $R_1$ is a W—$(CH_2)_m$— group.
32. A compound of claim 1 wherein said compound is 2H-Isoindole-2-hexanamide, N-[hexahydro-1-[2-(methylamino)-2-oxo-1-(phenylmethyl)ethyl]-2-oxo-5-phenyl-1H-azepin-3-yl]-1,3-dihydro-α-mercapto-1,3-dioxo-, [3S-[1(R*), 3α, 5α]]-.
33. A compound of claim 1 wherein said compound is 2H-Isoindole-2-hexanamide, N-[hexahydro-1-[2-(methylamino)-2-oxo-1-(phenylmethyl)ethyl]-2-oxo-5-phenyl-1H-azepin-3-yl]-1,3-dihydro-α-mercapto-1,3-dioxo-, [3S-[1(R*), 3α, 5β]]-.
34. A compound of claim 1 wherein said compound is 2H-Isoindole-2-hexanamide, N-[hexahydro-4-[2-(methylamino)-2-oxo-1-(phenylmethyl)ethyl]-5-oxo-1-(phenylmethyl)-1H-1,4-diazepin-6-yl]-1,3-dihydro-α-mercapto-1,3-dioxo-, [6S-[4(R*), 6R*(R*)]]-.
35. A pharmaceutical composition comprising a compound of claim 1 and a pharmaceutically acceptable carrier.
36. A method of treating rheumatoid arthritis in a patient in need thereof which comprises administering to the patient an effective matrix metalloproteinase inhibiting amount of a compound of claim 1.
37. A method of treating osteoarthritis in a patient in need thereof which comprises administering to the patient an effective matrix metalloproteinase inhibiting amount of a compound of claim 1.
38. A method of treating a chronic inflammatory disorder in a patient in need thereof which comprises administering to the patient an effective matrix metalloproteinase inhibiting amount of a compound of claim 1.
39. A method of treating atherosclerosis in a patient in need thereof which comprises administering to the patient an effective matrix metalloproteinase inhibiting amount of a compound of claim 1.
40. A method of treating corneal ulceration in a patient in need thereof which comprises administering to the patient an effective matrix metalloproteinase inhibiting amount of a compound of claim 1.
41. A method of treating gingivitis or periodontal disease in a patient in need thereof which comprises administering to the patient an effective matrix metalloproteinase inhibiting amount of a compound of claim 1.
42. A method of treating chronic obstructive pulmonary disorder in a patient in need thereof which comprises administering to the patient an effective matrix metalloproteinase inhibiting amount of a compound of claim 1.

* * * * *

UNITED STATES PATENT AND TRADEMARK OFFICE
CERTIFICATE OF CORRECTION

PATENT NO. : 6,953,788 B1
DATED : October 11, 2005
INVENTOR(S) : Warshawsky et al.

It is certified that error appears in the above-identified patent and that said Letters Patent is hereby corrected as shown below:

Column 5,
Line 1, replace "$-O, S, NR_7$" with -- O, S, $NR_7$ --.

Column 7,
Line 43, replace "I-position" with -- 1-position --.

Column 25,
Line 59, replace "$W-OR_7$" with -- $-OR_7$ --.

Column 32,
Line 62, replace "$-C_3-C_9$)heteroaryl" with -- $-(C_3-C_9)$heteroaryl --.

Column 45,
Line 55, replace "2540" with -- 25-40 --.

Column 55,
Line 20, replace "40°C" with -- -40°C --.

Column 69,
Line 16, replace "Z 8" with -- $Z'^8$ --.
Line 26, replace "a'" with -- a --.

Column 74,
Line 25, replace "0" with -- O --.

Column 75,
Line 48, replace "$R_9$" with -- $R_8$ --.

Column 78,
Line 66, replace "$^0$°C" with -- 0°C --.

UNITED STATES PATENT AND TRADEMARK OFFICE
CERTIFICATE OF CORRECTION

PATENT NO. : 6,953,788 B1
DATED : October 11, 2005
INVENTOR(S) : Warshawsky et al.

It is certified that error appears in the above-identified patent and that said Letters Patent is hereby corrected as shown below:

Column 106,
Line 55, replace " 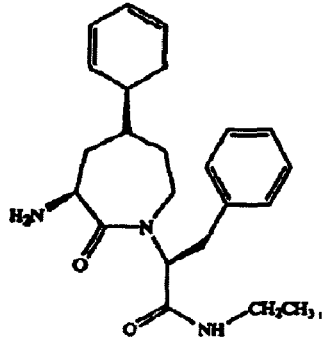 " with -- 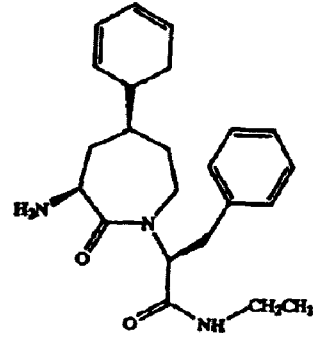 --.

Column 129,
Line 48, replace "$(O)_n$" with -- $(O)_p$ --.

Column 130,
Line 13, replace "-NHz" with -- $NH_2$ --.

Column 132,
Lines 2, 4 and 6, replace "$(H_2)_m$" with -- $(CH_2)_m$ --.

Signed and Sealed this

Twenty-third Day of May, 2006

JON W. DUDAS
*Director of the United States Patent and Trademark Office*